US008945540B2

(12) United States Patent
Becquerelle et al.

(10) Patent No.: US 8,945,540 B2
(45) Date of Patent: Feb. 3, 2015

(54) COMPOSITIONS FOR ENHANCING THE ANTIBACTERIAL ACTIVITY OF MYELOPEROXIDASE AND METHODS OF USE THEREOF

(75) Inventors: Sophie Becquerelle, Sebastopol, CA (US); William Haag, Berkeley, CA (US); Obsidiana Abril-Horpel, Brisbane, CA (US); Shri Valvani, Kalamazoo, MI (US)

(73) Assignee: Exoxemis, Inc., Little Rock, AR (US)

( * ) Notice: Subject to any disclaimer, the term of this patent is extended or adjusted under 35 U.S.C. 154(b) by 859 days.

(21) Appl. No.: 12/118,586

(22) Filed: May 9, 2008

(65) Prior Publication Data

US 2009/0280102 A1  Nov. 12, 2009

(51) Int. Cl.
*A61K 38/44* (2006.01)
*A61K 45/06* (2006.01)
*A61L 2/00* (2006.01)

(52) U.S. Cl.
CPC ......... *A61K 38/44* (2013.01); *C12Y 111/02002* (2013.01); *A61K 38/443* (2013.01); *C12Y 101/03004* (2013.01); *A61K 45/06* (2013.01); *A61L 2/0088* (2013.01)
USPC .......................................... 424/94.4; 514/2.4

(58) Field of Classification Search
CPC . A61K 2300/00; A61K 38/44; A61K 38/443; C12Y 101/03004; C12Y 111/02002; A61L 2/0088
USPC .......................................... 424/94.4; 514/2.4
See application file for complete search history.

(56) References Cited

U.S. PATENT DOCUMENTS

| | | | |
|---|---|---|---|
| 2,679,533 A | 5/1954 | Darragh | |
| 4,320,116 A | 3/1982 | Bjorck | |
| 4,473,550 A | 9/1984 | Rosenbaum | |
| 4,588,586 A | 5/1986 | Kessler | |
| 4,726,948 A | 2/1988 | Prieels | |
| 4,937,072 A | 6/1990 | Kessler | |
| 4,996,146 A | 2/1991 | Kessler | |
| 5,085,873 A | 2/1992 | Degre | |
| 5,206,156 A | 4/1993 | Samain | |
| 5,389,369 A | 2/1995 | Allen | |
| 5,451,402 A | 9/1995 | Allen | |
| 5,510,104 A | 4/1996 | Allen | |
| 5,565,197 A | 10/1996 | Allen | |
| 5,718,896 A | 2/1998 | Allen | |
| 5,756,090 A | 5/1998 | Allen | |
| 5,888,505 A | 3/1999 | Allen | |
| 6,033,662 A | 3/2000 | Allen | |
| 6,294,168 B1 | 9/2001 | Allen | |
| 6,503,507 B1 | 1/2003 | Allen | |
| 2008/0114054 A1* | 5/2008 | Microbes et al. | 514/428 |

FOREIGN PATENT DOCUMENTS

| | | |
|---|---|---|
| CN | 1128044 A | 7/1996 |
| EP | 0 098 073 A2 | 1/1984 |
| EP | 0 307 376 A1 | 3/1989 |
| EP | 0 361 908 A2 | 4/1990 |
| EP | 0 514 417 B1 | 11/1992 |
| GB | 2 108 387 A | 5/1983 |
| WO | 88/02600 A1 | 4/1988 |
| WO | 89/12457 A1 | 12/1989 |
| WO | 95/04135 A1 | 2/1995 |

OTHER PUBLICATIONS

Allen, R.C., "Chemiluminescence and the Study of Phagocyte Redox Metabolism," in F. Rossi and P. Patriarca (eds.), "Biochemistry and Function of Phagocytes (Advances in Experimental Medicine and Biology)," Plenum Publishing, New York, 1982, vol. 41, pp. 411-421.
Allen, R.C., "Biochemiexcitation: Chemiluminescence and the Study of Biological Oxygenation Reactions," in W. Adam and G. Cilento (eds.), "Chemical and Biological Generation of Excited States," Academic Press, New York, 1982, pp. 309-344.
Allen, R.C., "Chemiluminescence: An Approach to the Study of the Humoral-Phagocyte Axis in Host Defense Against Infection," in C.-T. Peng et al. (eds.), "Liquid Scintillation Counting: Recent Applicants and Development; vol. II. Sample Preparation and Applications," Academic Press, New York, 1980, pp. 377-393.
Allen, R.C., "Direct Quantification of Phagocyte Activity in Whole Blood: A Chemilumigenic Probe Approach," in E. Kaiser et al. (eds.), Proceedings of the 11th International Congress of Clinical Chemistry, Vienna, Aug. 30-Sep. 5, 1981, Walter de Gruyter & Co., Berlin, 1982, pp. 1043-1058.
Allen, R.C., "Evaluation of Serum Opsonic Capacity by Quantitating the Initial Chemiluminescent Response From Phagocytizing Polymorphonuclear Leukocytes," Infection and Immunity 15(3):828-833, Mar. 1977.
Allen, R.C., "Halide Dependence of the Myeloperoxidase-Mediated Antimicrobial System of the Polymorphonuclear Leukocyte in the Phenomenon of Electronic Excitation," Biochemical and Biophysical Research Communications 63(3):675-683, Apr. 1975.
Allen, R.C., "Oxygen-Dependent Microbe Killing by Phagocytic Leukocytes: Spin Conservation and Reaction Rate," in W. Ando and Y. Moro-oka (eds.), "The Role of Oxygen in Chemistry and Biochemistry," Proceedings of an International Symposium on Activation of Dioxygen and Homogeneous Catalytic Oxidations, Tsukuba, Japan, Jul. 12-16, 1987, published in Studies in Organic Chemistry 33:425-434, 1988.
Allen, R.C., "Phagocytic Leukocyte Oxygenation Activities and Chemiluminescence: A Kinetic Approach to Analysis," in M.A. DeLuca and W.D. McElroy (eds), "Methods in Enzymology," vol. 133, "Bioluminescence and Chemiluminescence, Part B," Academic Press, New York, 1986, pp. 449-493.

(Continued)

*Primary Examiner* — Taeyoon Kim
(74) *Attorney, Agent, or Firm* — Betts, Patterson & Mines, P.S.

(57) ABSTRACT

Methods and compositions are provided for inhibiting the growth of susceptible microorganisms by contacting the microorganisms, in the presence of a peroxide and chloride or bromide, with myeloperoxidase and at least two activity enhancing agent amino acids.

21 Claims, 6 Drawing Sheets

(56) References Cited

OTHER PUBLICATIONS

Allen, R.C., "Reduced, Radical, and Excited State Oxygen in Leukocyte Microbicidal Activity," in A. Neuberger and E.L. Tatum (eds), "Frontiers of Biology," North-Holland Publishing Company, Netherlands, 1979, vol. 48, pp. 198-233.

Allen, R.C., "Studies on the Generation of Electronic Excitation States in Human Polymorphonuclear Leukocytes and Their Participation in Microbicidal Activity," doctoral dissertation, Tulane University, New Orleans, Jul. 1973, 146 pages.

Allen, R.C., "The Role of pH in the Chemiluminescent Response of the Myeloperoxidase-Halide-HOOH Antimicrobial System," Biochemical and Biophysical Research Communications 63(3):684-691, Apr. 1975.

Allen, R.C., and B.A. Pruitt, Jr., "Humoral-Phagocyte Axis of Immune Defense in Burn Patients," Archives of Surgery 117:133-140, Feb. 1982.

Allen, R.C., and L.D. Loose, "Phagocytic Activation of a Luminol-Dependent Chemiluminescence in Rabbit Alveolar and Peritoneal Macrophages," Biochemical and Biophysical Research Communications 69(1):245-252, Mar. 1976.

Allen, R.C., and M.M. Lieberman, "Kinetic Analysis of Microbe Opsonification Based on Stimulated Polymorphonuclear Leukocyte Oxygenation Activity," Infection and Immunity 45(2):475-482, Aug. 1984.

Allen, R.C., et al., "Correlation of Metabolic and Chemiluminescent Responses of Granulocytes From Three Female Siblings With Chronic Granulomatous Disease," Journal of Infectious Diseases 136(4):510-518, Oct. 1977.

Allen, R.C., et al., "Evidence for the Generation of an Electronic Excitation State(s) in Human Polymorphonuclear Leukocytes and Its Participation in Bactericidal Activity," Biochemical and Biophysical Research Communications 47(4):679-684, May 1972.

Allen, R.C., et al., "Role of Myeloperoxidase and Bacterial Metabolism in Chemiluminescence of Granulocytes From Patients With Chronic Granulomatous Disease," Journal of Infectious Diseases 144(4):344-348, Oct. 1981.

Belding, M.E., and S.J. Klebanoff, "Peroxidase-Mediated Virucidal Systems," Science 167:195-196, Jan. 1970.

Chenoweth, D.E., "Complement Mediators of Inflammation," in G.D. Ross (ed.), "Immunobiology of the Complement System: An Introduction for Research and Clinical Medicine," Academic Press, New York, 1986, pp. 63-86.

Clark, R.A., et al., "Peroxidase-H2O2-Halide System: Cytotoxic Effect on Mammalian Tumor Cells," Blood: The Journal of Hematology 45(2):161-170, Feb. 1975.

Fearon, D.T., and L.A. Collins, "Increased Expression of C3b Receptors on Polymorphonuclear Leukocytes Induced by Chemotactic Factors and by Purification Procedures," Journal of Immunology 130(1):370-375, Jan. 1983.

Fearon, D.T., and W.W. Wong, "Complement Ligand-Receptor Interactions That Mediate Biological Responses," Annual Review of Immunology 1:243-271, Apr. 1983.

Hamon, C.B., and S.J. Klebanoff, "A Peroxidase-Mediated, *Streptococcus mitis*-Dependent Antimicrobial System in Saliva," Journal of Experimental Medicine 137:438-450, 1973.

Kanofsky, J.R., "Singlet Oxygen Production by Lactoperoxidase," Journal of Biological Chemistry 258(10):5991-5993, May 1983.

Kearns, D.R., and A.U. Khan, "Sensitized Photooxygenation Reactions and the Role of Singlet Oxygen," Photochemistry and Photobiology 10:193-210, Mar. 1969.

Klebanoff, S.J., "Myeloperoxidase-Halide-Hydrogen Peroxide Antibacterial System," Journal of Bacteriology 95(6):2131-2138, Jun. 1968.

Klebanoff, S.J., "Myeloperoxidase-Mediated Antimicrobial Systems and Their Role in Leukocyte Function" (presented at the Symposium on Membrane Function and Electron Transfer to Oxygen, Miami, Jan. 22-24, 1969), in J. Schultz (ed), "Biochemistry of the Phagocytic Process," North-Holland Publishing Company, Netherlands, 1970, pp. 89-110.

Klebanoff, S.J., and C.C. Shepard, "Toxic Effect of the Peroxidase-Hydrogen Peroxide-Halide Antimicrobial System on *Mycobacterium leprae*," Infection and Immunity 44(2):534-536, May 1984.

Klebanoff, S.J., and M.E. Belding, "Virucidal Activity of H2O2-Generating Bacteria: Requirement for Peroxidase and a Halide," Journal of Infectious Diseases 129(3):345-348, Mar. 1974.

Klebanoff, S.J., and R.W. Coombs, "Viricidal Effect of *Lactobacillus acidophilus* on Human Immunodeficiency Virus Type 1: Possible Role in Heterosexual Transmission," Journal of Experimental Medicine 174:289-292, Jul. 1991.

Klebanoff, S.J., et al., "Antimicrobial Activity of Myeloperoxidase," in L. Packer (ed.), "Methods in Enzymology," vol. 105, "Oxygen Radicals in Biological Systems," Academic Press, New York, 1984, pp. 399-403.

Klebanoff, S.J., et al., "The Peroxidase-Thiocyanate-Hydrogen Peroxide Antimicrobial System," Biochimica et Biophysica Acta 117(1):63-72, Mar. 1966.

Lehrer, R.I., "Antifungal Effects of Peroxidase Systems," Journal of Bacteriology 99(2):361-365, Aug. 1969.

Mickelson, M.N., "Effect of Lactoperoxidase and Thiocyanate on the Growth of *Streptococcus pyogenes* and *Streptococcus agalactiae* in a Chemically Defined Culture Medium," Journal of General Microbiology 43(1):31-43, Apr. 1966.

Moguilevsky, N., et al., "Lethal Oxidative Damage to Human Immunodeficiency Virus by Human Recombinant Myeloperoxidase," FEBS Letters 302(3):209-212, May 1992.

Olsson, I., and P. Venge, "The Role of the Human Neutrophil in the Inflammatory Reaction," Allergy 35(1):1-3, Jan. 1980.

Rosen, H., and S.J. Klebanoff, "Formation of Singlet Oxygen by the Myeloperoxidase-Mediated Antimicrobial System," Journal of Biological Chemistry 252(14):4803-4810, Jul. 1977.

Steele, W.F., and M. Morrison, "Antistreptococcal Activity of Lactoperoxidase," Journal of Bacteriology 97(2):635-639, Feb. 1969.

Steinbeck, M.J., and J.A. Roth, "Neutrophil Activation by Recombinant Cytokines," Reviews of Infectious Diseases 11(4):549-568, Jul.-Aug. 1989.

Thomas, E.L., and M. Fishman, "Oxidation of Chloride and Thiocyanate by Isolated Leukocytes," Journal of Biological Chemistry 261(21):9694-9702, Jul. 1986.

Anderson, M.M., et al., "The Myeloperoxidase System of Human Phagocytes Generates Nε-(carboxymethyl)lysine on Proteins: a Mechanism for Producing Advanced Glycation End Products at Sites of Inflammation," The Journal of Clinical Investigation 104(1):103-113, Jul. 1999.

International Search Report and Written Opinion of the International Searching Authority mailed Jun. 25, 2009, issued in corresponding International Application No. PCT/US2009/043172, filed May 7, 2009.

Notification of the First Office Action of the State Intellectual Property Office of the People's Republic of China, mailed Jul. 26, 2012, issued in corresponding Chinese Application No. 200980114532.5, filed May 7, 2009, 7 pages.

Official Action received on Jul. 8, 2013, issued in corresponding Russian Application No. 2010/150428/15(072788), filed May 7, 2009, 3 pages.

\* cited by examiner

COMPOSITIONS FOR ENHANCING THE ANTIBACTERIAL ACTIVITY OF MYELOPEROXIDASE AND METHODS OF USE THEREOF

The present invention relates to methods and compositions for the inhibition or treatment of microbial infections. More particularly, the present invention relates to methods and compositions using a combination of amino acids and myeloperoxidase to enhance microbicidal properties of the system.

BACKGROUND

As disclosed in U.S. Pat. Nos. 5,888,505 and 6,294,168, myeloperoxidase may be used to selectively bind to and, in the presence of peroxide and halide, inhibit the growth of target microorganisms without eliminating desirable microorganisms or significantly damaging other components of the medium, such as host cells and normal flora, in the target microorganism's environment. Myeloperoxidase has previously been known to exhibit microorganism killing activity in natural systems when presented with an appropriate halide cofactor ($X^-$) and hydrogen peroxide as substrate (Klebanoff, 1968, *J. Bacteriol.* 95:2131-2138). However, the selective nature of myeloperoxidase binding and the utility of these systems for therapeutic, research and industrial applications has only recently been recognized. Due to the newly discovered selective binding properties of myeloperoxidase, when a target microorganism, such as a pathogenic microorganism, has a binding capacity for myeloperoxidase greater than that of a desired microorganism, such as members of the normal flora, the target microorganism selectively binds the myeloperoxidase with little or no binding of the myeloperoxidase by the desired microorganism. In the presence of peroxide and halide, the target bound myeloperoxidase catalyzes halide oxidation and facilitates the disproportionation of peroxide to singlet molecular oxygen ($^1O_2$) at the surface of the target microorganism, resulting in selective killing of the target microorganism with a minimum of collateral damage to the desired microorganism or physiological medium. Thus, as disclosed in U.S. Pat. Nos. 5,888,505 and 6,294,168, myeloperoxidase can be employed as an antiseptic in the therapeutic or prophylactic treatment of human or animal subjects to selectively bind to and kill pathogenic microorganisms with a minimum of collateral damage to host cells and normal flora of the host.

The system may also be employed as disinfecting or sterilizing formulations for inhibiting the growth of target microorganisms in vitro, particularly in applications where biomedical devices, such as bandages, surgical instruments, suturing devices, catheters, dental appliances, contact lenses and the like, are antiseptically treated to inhibit the growth of target microorganisms without damage to host cells of a subject when the biomedical device is subsequently utilized in vivo.

As disclosed in U.S. Pat. Nos. 5,389,369 and 5,451,402, while the myeloperoxidase antiseptic system disclosed in U.S. Pat. Nos. 5,888,505 and 6,294,168 has been found to be highly effective in the treatment of pathogenic microbes, an antimicrobial activity enhancing agent may be required for the effective killing of yeast and spore forming microorganisms. The spore stage of the microbial life cycle is characterized by metabolic dormancy and resistance to environmental factors that would destroy the microbe in its vegetative stage. The earliest phase of spore germination is characterized by swelling and a shift from dormancy to active metabolism. Vegetative growth, e.g., sprouting, and ultimately reproduction follows.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine is reported to stimulate bacterial spore germination (Hills, 1950, *J Gen Microbiol* 4:38; Halvorson and Church, 1957, *Bacteriol Rev* 21:112). L-Alanine and L-proline have also been reported to initiate fungal spore germination (Yanagita, 1957, *Arch Mikrobiol* 26:329).

Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate which is the end product of glycolytic metabolism (Embden-Meyerhof-Parnas Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle) which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

Accordingly, U.S. Pat. Nos. 5,389,369 and 5,451,402 disclose that the microbicidal action of myeloperoxidase against yeast and sporular forms of microbes may be enhanced by treating the microorganisms with myeloperoxidase in combination with certain α-amino acids which provide a stimulating effect on yeast budding, germination of sporulated microbes, and possibly acceleration of metabolism of vegetative microbes. Representative α-amino acids disclosed for this purpose include glycine and the L- or D-enantiomers of alanine, valine, leucine, isoleucine, serine, threonine, lysine, phenylalanine, tyrosine, and the alkyl esters thereof. While U.S. Pat. Nos. 5,389,369 and 5,451,402 disclose the enhancement of microbicidal activity of myeloperoxidase against yeast and sporular forms of microbes with α-amino acids, these patents do not disclose enhancement of the myeloperoxidase microbicidal system against non-sporular bacterial or the further enhancement of antibacterial activity by the use of myeloperoxidase and at least two amino acids, as disclosed herein.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention is directed to compositions and methods for the killing or inhibition of microbial infections, such as bacterial infections, by contacting the site of infection with a composition comprising myeloperoxidase and at least two amino acids that work in combination to enhance myeloperoxidase microbicidal activity. In the practice of the invention, susceptible microorganisms are killed or inhibited by contacting the microorganisms with amounts of myeloperoxidase and at least two amino acids, which are effective in the presence of a peroxide and bromide or chloride, to inhibit the growth of or kill the microorganisms.

Thus, in one embodiment, the invention provides compositions for inhibiting the growth of susceptible microorganisms comprising myeloperoxidase and at least two amino acids that work in combination to enhance the microbicidal activity of the myeloperoxidase. In some embodiments, the at least two amino acids are selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta amino acids, such as beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, ethyl 3-aminobutyrate, sarcosine methyl ester hydrochloride and nipecotic acid, or an alkyl ester or pharmaceutically acceptable salt thereof. In other embodiments, the at least two amino acids are selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, and D-valine, or an alkyl ester or pharmaceutically acceptable salt thereof.

In other aspects, the invention provides compositions for inhibiting the growth of susceptible microorganisms comprising myeloperoxidase and at least three amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, 1-proline, L-hydroxyproline, L-serine, taurine, L-threonine, D-threonine, L-tyrosine, L-valine, D-valine, beta amino acids, such as beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, ethyl 3-aminobutyrate, sarcosine methyl ester hydrochloride and nipecotic acid, or an alkyl ester or pharmaceutically acceptable salt thereof. In other aspects, the at least three amino acids are selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, and D-valine, or an alkyl ester or pharmaceutically acceptable salt thereof.

In some embodiments, the compositions of the invention further comprise hydrogen peroxide or a source of hydrogen peroxide. In this aspect of the invention, the compositions may comprise a peroxide producing oxidase that produces hydrogen peroxide in the presence of a substrate for the oxidase. In some embodiments, the compositions comprise a peroxide producing oxidase effective to generate from 100 pmol to 50 µmol peroxide per ml per minute when in the presence of a substrate for the oxidase.

In one embodiment, the compositions of the invention comprise from 1 to 50,000 µg/ml of myeloperoxidase. In other embodiments, the compositions of the invention comprise 0.1 to about 500 mM of each of the at least two amino acids. In one representative embodiment, the compositions of the invention comprise from 10 to 5,000 µg/ml of myeloperoxidase, from 0.3 to 50 mM of glycine, from 0.3 to 50 mM of L-alanine, from 0.3 to 50 mM of L-proline, and from 1 to 500 U/ml of glucose oxidase.

In other aspects, the invention provides methods of treating a human or animal subject in need of such treatment comprising administering to a site of infection in the subject a composition comprising myeloperoxidase and at least two amino acids that work in combination, in the presence of hydrogen peroxide and chloride or bromide, to enhance the microbicidal activity of the myeloperoxidase. In some embodiments of this aspect of the invention, the at least two amino acids are selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta amino acids, such as beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, ethyl 3-aminobutyrate, sarcosine methyl ester hydrochloride and nipecotic acid, or an alkyl ester or pharmaceutically acceptable salt thereof. In other embodiments of this aspect of the invention, the at least two amino acids are selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, and D-valine, or an alkyl ester or pharmaceutically acceptable salt thereof.

In other embodiments, the invention provides methods of treating a human or animal subject in need of such treatment comprising administering to a site of infection in the subject a composition comprising myeloperoxidase and at least three amino acids that work in combination, in the presence of hydrogen peroxide and chloride or bromide, to enhance the microbicidal activity of the myeloperoxidase. In some embodiments, the at least three amino acids are selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta amino acids, such as beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, ethyl 3-aminobutyrate, sarcosine methyl ester hydrochloride and nipecotic acid, or an alkyl ester or pharmaceutically acceptable salt thereof. In other embodiments, the at least three amino acids are selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, and D-valine, or an alkyl ester or pharmaceutically acceptable salt thereof.

In other embodiments, the composition administered to the human or animal subject may additionally comprise hydrogen peroxide or a source of hydrogen peroxide. In some embodiments, the source of hydrogen peroxide comprises a peroxide producing oxidase that produces hydrogen peroxide in the presence of a substrate for the oxidase. For example, the composition administered to the human or animal subject may additionally comprise a peroxide producing oxidase effective to generate from 100 pmol to 50 µmol peroxide per ml per minute when in the presence of a substrate for the oxidase.

In some embodiments, the composition administered to the human or animal subject may comprise from 1 to 50,000 µg/ml of myeloperoxidase. In other embodiments, the composition administered to the human or animal subject may comprise from 0.1 to about 500 mM of each of the at least two amino acids. In one representative embodiment, the composition administered to the human or animal subject may comprise from 10 to 5,000 µg/ml of myeloperoxidase, from 0.3 to 50 mM of glycine, from 0.3 to 50 mM of L-alanine, from 0.3 to 50 mM of L-proline, and from 1 to 500 U/ml of glucose oxidase.

In some aspects of the invention, the human or animal subject to be treated is suffering from a microbial infection of the gums, eyes, ears, skin, soft tissue, wounds, vaginal areas, groin areas, bed sores or burn areas. In some embodiments, the infection is a polymicrobial infection. In other embodiments, the infection is caused, at least in part, by a multidrug resistant microorganism.

In other aspects, the invention provides methods for killing or inhibiting the growth of susceptible microorganisms comprising contacting the microorganisms, in the presence of hydrogen peroxide and chloride or bromide, with a composition comprising myeloperoxidase and at least two amino acids that work in combination to enhance the microbicidal activity of the myeloperoxidase.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
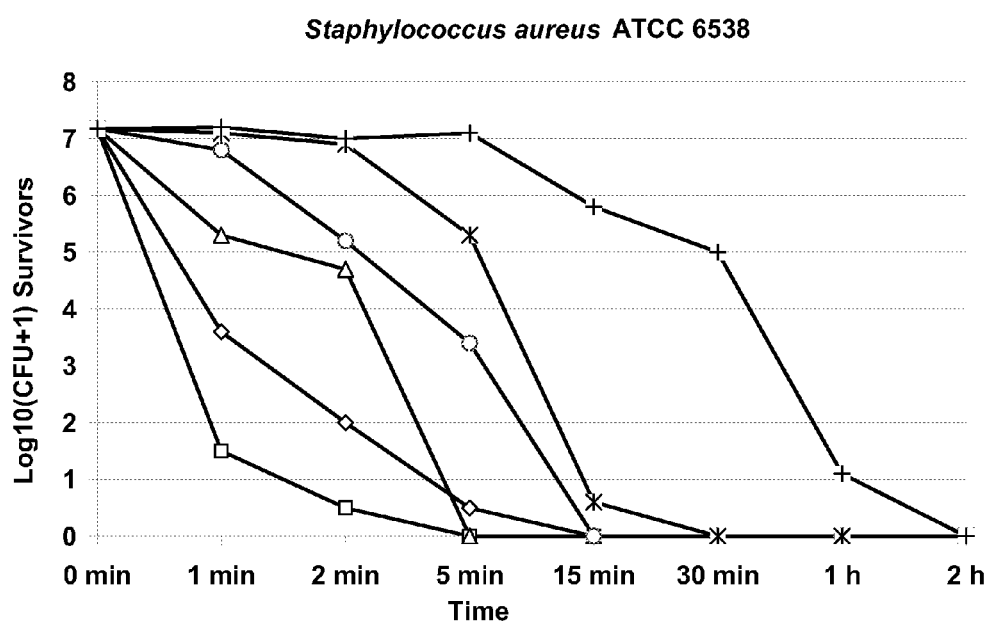
FIG. 1 is a time-kill analysis of S. aureus ATCC 6538 (FIG. 1A) and E. coli ATCC 25922 (FIG. 1B) treated with an Enhanced MPO Solution containing 9 (□), 6 (◇), 3 (Δ), 1 (○), 0.3 (*), and 0.1 (+) µg MPO/ml, as described in Example 11. Rapid bactericidal activity (>3 log reduction from the initial inoculum) was demonstrated using the suspension-neutralization method. The rate of kill was greater at higher MPO concentrations of the Enhanced MPO Solution and the extent of kill increased with longer exposure time. At concentrations of 3 µg MPO/ml and above, no detectable survivors were observed within 5 minutes of exposure.

The present invention is broadly directed to compositions and methods for the killing or inhibition of bacterial infections using myeloperoxidase and at least two amino acids that work in combination to enhance the microbicidal activity of myeloperoxidase. In the practice of the invention, susceptible microorganisms are killed or inhibited by contacting the microorganisms with amounts of myeloperoxidase and at least two amino acids, which are effective in the presence of a peroxide and bromide or chloride, to inhibit the growth of or kill the microorganisms.

In one particularly preferred embodiment, the compositions and methods of the invention are used as antiseptic agents exhibiting enhanced myeloperoxidase antimicrobial activity against a broad range of pathogenic microorganisms including bacteria and fungi. In one aspect, the compositions and methods of the invention are highly suitable for the topical treatment of susceptible infections in a human or non-human mammalian subject at sites permitting direct contact of the compositions of the invention with the microbial infection, such as, for example, infections of the skin, eyes, ears, mouth, nasal and sinus passages, traumatic injury sites, surgical sites and the like. For use in contact with host tissue, the antiseptic systems are based on the use of dioxygenating myeloperoxidase which exhibits selective affinity for pathogenic microorganisms. As such, high potency microbicidal action can be directed to the target microorganisms without associated host tissue destruction or disruption of normal flora; i.e., the antiseptic action is selective and confined to the target microorganism.

Thus, in one embodiment, the invention provides compositions for inhibiting the growth of susceptible microorganisms comprising myeloperoxidase and at least two amino acids that work in combination, in the presence of peroxide and chloride or bromide, to enhance the microbicidal activity of the myeloperoxidase. The compositions may additionally comprise hydrogen peroxide or a source of hydrogen peroxide, and chloride or bromide, when not otherwise available in sufficient amounts at the site of use of the compositions. In a related embodiment, the invention provides methods of treating a human or animal subject in need of such treatment comprising administering to a site of infection in the subject a composition comprising myeloperoxidase and at least two amino acids that work in combination to enhance the microbicidal activity of the myeloperoxidase. Again, the composition may additionally comprise hydrogen peroxide or a source of hydrogen peroxide, and chloride or bromide, to supplement naturally occurring amounts at the infection site.

In other embodiments, the invention provides compositions and methods for inhibiting the growth of susceptible microorganisms in vitro, particularly in applications where biomedical devices, such as bandages, surgical instruments, suturing devices, catheters, dental appliances, contact lenses and the like, require disinfection or sterilization and where the device is to be subsequently contacted with host tissue. Thus, high potency myeloperoxidase formulations of the invention can serve as in vitro disinfecting or sterilizing preparations. By limiting the time period of hydrogen peroxide availability, myeloperoxidase-enhanced formulations can be made sufficiently potent to insure disinfection and even sterilization of a material or device before contact with host tissue. Any potential toxicity to normal flora and host tissue associated with the use of these high potency formulations ceases when peroxide is depleted, and as such, the formulation-treated material or device can be brought in contact with host tissue without additional washing or detoxification.

Thus, in one embodiment, the invention provides methods for killing or inhibiting the growth of susceptible microorganisms in vitro comprising contacting the microorganisms, in the presence of hydrogen peroxide and chloride or bromide, with a composition comprising myeloperoxidase and at least two amino acids that work in combination to enhance the microbicidal activity of the myeloperoxidase.

Representative compositions of the invention comprise (1) myeloperoxidase (MPO), (2) at least two activity enhancing amino acids, and optionally (3) hydrogen peroxide ($H_2O_2$) or a source of $H_2O_2$, and (4) chloride or bromide.

Myeloperoxidase useful in the present invention is a halide:hydrogen peroxide oxidoreductase (e.g., EC No. 1.11.1.7 and EC No. 1.11.1.10 under the International Union of Biochemistry) for which halide, i.e., chloride or bromide, is the electron donor or reductant and peroxide is the electron receiver or oxidant. The enzymatic activity of a myeloperoxidase solution can be determined by reaction with guaiacol in the presence of hydrogen peroxide in sodium phosphate buffer. The reaction generates a product with strong absorbance at 470 nm. The activity is determined from the kinetics of the increase in absorbance compared to a reference standard. Myeloperoxidase activity is commonly expressed in Guaiacol units/mL (GU/mL), and is also expressed as micrograms of MPO per milliliter (μg/mL). The conversion of μg to GU of MPO is based on 0.375 GU per μg of MPO. The specific activity is calculated from its activity and the total protein concentration and expressed in GU/mg protein. Useful amounts of myeloperoxidase employed in the compositions of the invention will vary widely depending on conditions under which the compositions are employed, the environment of use and the desired result. For most purposes, the compositions of the invention will generally comprise at least about 0.05 μg/ml (0.01875 GU/ml) of myeloperoxidase. In some embodiments, the compositions of the invention will comprise from about 1 to about 50,000 μg/ml of myeloperoxidase (i.e., from about 0.375 to about 18,750 GU/ml), more preferably from about 5 to about 10,000 μg/ml of myeloperoxidase (i.e., from about 1.875 to about 3,750 GU/ml), and even more preferably from about 10 to about 5,000 μg/ml of myeloperoxidase (i.e., from about 3.75 to about 1,875 GU/ml).

Inclusion of at least two activity enhancing amino acids, as described in detail herein, greatly increases the microbicidal capacity of the oxidase-myeloperoxidase system against susceptible microorganisms. Amino acids useful in the practice of the invention are those amino acids that, when used in combination and in the presence of peroxide and chloride or bromide, enhance the antimicrobial activity of the myeloperoxidase antimicrobial system against susceptible microorganisms. At least two amino acids are used at concentrations that do not produce adverse effects on the myeloperoxidase activity of the system or undesirable effects in the environment of use of the compositions and methods.

In some embodiments, the compositions of the invention comprise at least two amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta amino acids, such as beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, and ethyl 3-aminobutyrate, as well as the alkyl esters thereof, such as, for example, L-alanine methyl ester, D-alanine methyl ester, L-lysine methyl ester dihydrochloride, glycine methyl ester hydrochloride, L-proline methyl ester hydrochloride, L-valine ethyl ester hydrochloride and ethyl 2-aminopropanoate, and N-substituted amino acids, such as sarcosine methyl ester hydrochloride and nipecotic acid.

In other embodiments, the compositions of the invention comprise at least two amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, and D-valine, as well as alkyl esters thereof.

In some embodiments, the compositions of the invention comprise myeloperoxidase and at least three amino acids that work in combination to enhance myeloperoxidase microbicidal activity. Accordingly, in some embodiments, the compositions of the invention comprise at least three amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta amino acids, such as beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, and ethyl 3-aminobutyrate, as well as esters thereof, such as, for example, L-alanine methyl ester, D-alanine methyl ester, L-lysine methyl ester dihydrochloride, glycine methyl ester hydrochloride, L-proline methyl ester hydrochloride, L-valine ethyl ester hydrochloride and ethyl 2-aminopropanoate, and N-substituted amino acids, such as sarcosine methyl ester hydrochloride and nipecotic acid.

In still other embodiments, the compositions of the invention comprise at least three amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, and D-valine, as well as esters thereof. In one presently preferred representative example of this aspect of the invention, the compositions of the invention comprise myeloperoxidase and the amino acids glycine, L-alanine and L-proline, in amounts effective to enhance the antimicrobial activity of myeloperoxidase.

Useful amounts of the amino acids employed in the compositions of the invention will vary depending on amount of myeloperoxidase in the compositions and conditions present in the environment of use. For most purposes, the compositions of the invention will generally comprise from about 0.1 to about 500 mM, more preferably from about 0.2 to about 100 mM, and even more preferably from about 0.3 to about 50 mM of each of the amino acids of the invention.

Since the antiseptic activity of the myeloperoxidase compositions of the invention involves the reaction of peroxide and chloride or bromide to form hypohalite, and the reaction of peroxide and hypohalite to form singlet molecular oxygen, the activity of the compositions of the invention is dependent upon the presence, at the site of antimicrobial activity, of a suitable peroxide and halide. In some situations, peroxide (e.g., hydrogen peroxide) may be present at the site of antimicrobial activity due, for example, to the activity of naturally occurring flora, and sufficient amounts of chloride may be present in the physiological milieu to act as a cofactor in the conversion reaction. In these situations, no additional peroxide or halide need be administered or included in the compositions of the invention. In other situations, it may be necessary or desirable to additionally provide hydrogen peroxide and/or halide at the site of microbial treatment. Accordingly, the compositions of the invention may additionally comprise, if desired, a peroxide or agent capable of producing peroxide in vivo or in vitro and chloride or bromide.

Peroxides useful in the compositions and methods of the invention include hydrogen peroxide, alkyl hydroperoxides of the formula:

wherein R is hydrogen or a short chain alkyl group having from 1 to 3 carbon atoms, and inorganic peroxides, such as boroperoxide or ureaperoxide. The oxidant activity of the organic peroxides generally decreases with increasing R chain length, as follows:

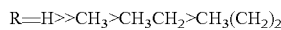

The presently preferred peroxide for use in the compositions of the invention is hydrogen peroxide. Hydrogen peroxide may also be made available at the site of the antimicrobial activity by including in the composition an agent capable of producing hydrogen peroxide in vivo or in vitro. Particularly useful agents for this purpose include, for example, oxidases, such as glucose oxidase, cholesterol oxidase and galactose oxidase.

When hydrogen peroxide is directly included in compositions of the invention for in vivo applications, the amounts employed are preferably designed to provide maximum disinfecting activity. Damage to host cells and tissue and to normal flora is avoided by avoiding direct contact during the period of high $H_2O_2$ exposure. Accordingly, the compositions of the invention may comprise from about 1 nmol to about 10 µmol of hydrogen peroxide per ml of composition, more preferably from about 5 nmol to about 5 µmol of hydrogen peroxide per ml of composition, and most preferably from about 10 nmol to about 1 µmol of hydrogen peroxide per ml of composition. Agents capable of producing hydrogen peroxide in vivo, e.g., peroxide producing oxidases, are particularly useful for dynamic control of the amounts of hydrogen peroxide present at the site of antimicrobial activity. Such agents maximize antimicrobial activity of the composition by providing and maintaining a steady, low level concentration of $H_2O_2$. Accordingly, the amount of such agents to be employed will be highly dependent on the nature of the agent and the effect desired, but will preferably be capable of producing a steady state level of from about 1 pmol to about 1 µmol of hydrogen peroxide per ml of liquid per minute, depending on the type and concentration of halide available at the site of antimicrobial activity. When the formulation is to be used as a disinfectant-sterilizing solution, the oxidase and its substrate can be adjusted to provide relatively high steady-state concentrations of $H_2O_2$ lasting for the required sterilization period. The disinfection-sterilizing action is terminated with exhaustion of the oxidase substrate or relative to the rate of oxidase degradation. As a representative example, when the oxidase is glucose oxidase and its substrate is glucose, the compositions of the invention may comprise from about 0.05 to about 3,000 U/ml, more preferably from about 0.1 to about 1,000 U/ml, and even more preferably from about 1 to about 500 U/ml of glucose oxidase, and from about 0.1 to about 1,000 mM, more preferably from about 0.5 to about 800 mM, and even more preferably from about 1 to about 500 mM glucose.

When bromide or chloride are included in the compositions of the invention, the use, selection and amount of bromide or chloride employed in a particular application will depend upon various factors, such as the desired therapeutic effect, the availability of peroxide and other factors. Since chloride is present in most physiological media at levels sufficient to be non-limiting as the halide cofactor, an external source of chloride is generally not required. When an external source of chloride is desired, the amount of chloride employed will preferably fall in the range of about 10 µmol chloride to about 150 µmol chloride per ml of solution to approximate physiological conditions. When included, the compositions of the invention may comprise from about 1 nmol bromide to about 20 µmol bromide per ml of liquid composition, more preferably from about 10 nmol bromide to about 10 µmol bromide per ml of liquid composition, and most preferably from about 100 nmol bromide to about 1 µmol bromide per ml of liquid composition.

The ratio of halide to peroxide is an important consideration in formulating an effective microbicidal environment. Accordingly, in addition to ensuring effective levels of halide and peroxide at the situs of microbial attack, as described above, it is preferable to practice the methods of the invention at halide:peroxide ratios that provide optimal microbicidal activity. For example, when the halide is $Cl^-$, the ratio of $Cl^-$ to peroxide is preferably maintained in the range of about 1 to about 40,000 in the environment of microbicidal activity, more preferably from about 50 to about 40,000 and most preferably from about 200 to about 40,000. When the halide is $Br^-$, the ratio of $Br^-$ to peroxide is preferably maintained in the range of about 0.1 to about 4,000 in the environment of microbicidal activity, more preferably from about 0.5 to about 2,000 and most preferably from about 1 to about 1,000.

The compositions and methods of the invention can be used to inhibit the growth of a broad spectrum of pathological microorganisms, preferably with a minimum of damage to normal flora. As demonstrated in the examples, compositions of the invention are highly efficient in the inhibition of both Gram-positive and Gram-negative organisms, such as, for example, *Enterococcus faecalis, Enterococcus faecium, Staphylococcus aureus, Staphylococcus epidermidis, Streptococcus agalactiae, Streptococcus* Group C, *Streptococcus* Group F, *Streptococcus* Group G, *Streptococcus pyogenes, Citrobacter freundii, Enterobacter cloacae, Escherichia coli, Klebsiella pneumoniae, Proteus mirabilis, Acintobacter* spp., *Pseudomonas aeruginosa, Aeromonas hydrophilia,* and *Pasteurella multocida*. In addition, the compositions of the invention are useful in the inhibition of spore forming microorganisms such as, for example, bacteria such as *Bacillus* sps. and *Clostridium* sps., and fungi such as *Aspergillis* sps., *Fusarium* sps., *Trichophyton* sps. and the like. Due to their wide spectrum of activity, in some embodiments the compositions of the invention may be advantageously used in the treatment of polymicrobial infections. Polymicrobial diseases involve multiple infectious agents and are referred to as complex, complicated, mixed, dual, secondary, synergistic, concurrent, polymicrobial, or coinfections. Polymicrobial diseases include, for example, infections associated with abscesses, AIDS-related opportunistic infections, conjunctivitis, gastroenteritis, hepatitis, multiple sclerosis, otitis media, periodontal diseases, respiratory diseases, and genital infections. In addition, since the compositions of the invention operate by an entire different mechanism of action than those involved in conventional antibiotic therapy, in some embodiments the compositions of the invention are also highly useful in the treatment of infections caused, at least in part, by multidrug resistant pathogens, such as MRSA (methicillin-resistant *Staphylococcus aureus*), VRSA (Vancomycin-resistant *S. aureus*), VRE (Vancomycin-Resistant *Enterococcus*), Penicillin-Resistant *Enterococcus*, PRSP (Penicillin-resistant *Streptococcus pneumoniae*), isoniazid/rifampin-resistant *Mycobacterium tuberculosis* and other antibiotic-resistant strains of *E. coli, Salmonella, Campylobacter*, and Streptococci. Such bacteria are herein referred to as "antibiotic-resistant" or "drug-resistant" or "multidrug-resistant", or by other similar terms that are well understood in the art.

As used herein, the term "normal flora" means bacteria, which normally reside in or on body surfaces of a healthy host at symbiotic levels. Normal flora include, for example, the lactic acid family of bacteria in the mouth, intestine, or vagina of human subjects, e.g. *Streptococcus* (viridans) in the mouth, and *Lactobacillus* sp. (e.g., Tissier's bacillus and Doderlein's bacillus) in the intestines of breast-fed infants, external genitalia, anterior urethra and vagina. Microorganisms which constitute normal flora of a host are well known (e.g., see *Principles and Practice of Infectious Diseases*, supra, New York, pp. 34-36 and 161). It has been found that the myeloperoxidase of the invention selectively bind to many pathogenic bacteria and fungi in preference over normal flora. In in vivo applications, the host is preferably treated with an amount of myeloperoxidase which is ineffective to eliminate normal flora from the host. In in vitro applications for disinfection-sterilization, sufficiently high concentrations of myeloperoxidase can be employed to ensure complete killing of all vegetative and yeast forms. Under such conditions, damage to host tissue and normal flora is avoided by consumption of $H_2O_2$ or the $H_2O_2$-generating system prior to contact with the host tissue.

The compositions of the invention generally comprise amounts of a myeloperoxidase and at least two amino acids which are effective, in the presence of a peroxide and a halide to kill or inhibit the growth of susceptible microorganisms. The compositions may additionally comprise a pharmaceutically acceptable carrier. In some embodiments, the compositions may be conveniently provided in a liquid carrier. Any liquid carrier may be generally used for this purpose, provided that the carrier does not significantly interfere with the selective binding capabilities of the myeloperoxidase or with enzyme activity. Alternatively, the compositions may be provided in solid form with activation on solubilization in liquid.

As set forth above, the compositions of the invention may additionally comprise peroxide or an agent capable of producing peroxide, such as an oxidase, as described in detail above. The oxidase-myeloperoxidase system lends itself to construction as a binary formulation in which the composition active agents are formulated in two separate parts for consolidation at the time of use. For example, one part of the binary formulation may comprise a solution containing the oxidase, the myeloperoxidase and at least two activity-enhancing amino acids, e.g., glycine, L-alanine and L-proline. The second part of the binary may comprise a substrate for the oxidase, e.g., glucose or dextrose in the case of glucose oxidase or molecular oxygen, $O_2$. The substrate may be provided, for example, in the form of a solid wafer. For sterilization of an article, e.g., a surgical instrument or a contact lens, the substrate wafer may be placed in a sterilization chamber along with the item to be sterilized. The myeloperoxidase, activity enhancing amino acids and oxidase is added to initiate sterilization. In some embodiments, the myeloperoxidase composition may additionally comprise alcohol in order to facilitate oxidase substrate solubilization and utilization by the oxidase. This system will produce sustained microbicidal action as long as sufficient substrate is present to drive the reaction.

The compositions of the invention may be administered alone or in combination with one or more other therapeutic agents. Representative additional therapeutic agents that may be used in combination with the compositions of the invention include, for example, antibiotic or antiseptic agents such as anti-bacterial agents, anti-fungicides, anti-viral agents and/or anti-parasitic agents. In some embodiments, the additional therapeutic agents may be one or more penicillins, cephalosporins, cephamycins, cephamycins, carbapenems, monobactams, aminoglycosides, glycopeptides, quinolones, tetracyclines, macrolides, and/or fluoroquinolones. In some embodiments, the additional therapeutic agents may be iodine, silver, copper, chlorhexidine, polyhexanide, biguanides, chitosan and/or acetic acid. The one or more additional therapeutic agents of the invention may be incorporated as part of the same composition or may be administered separately.

For in vivo applications, the antiseptic compositions can be administered in any effective pharmaceutically acceptable form to warm blooded animals, including human and animal subjects, e.g., in topical, lavage, oral, vaginal or suppository dosage forms, as a topical, buccal, nasal spray, aerosol for inhalation or in any other manner effective to deliver active myeloperoxidase to a site of microorganism infection. The route of administration will preferably be designed to obtain direct contact of the antiseptic compositions with the infecting microorganisms. In one aspect of the invention, the compositions of the invention are delivered or administered topically to areas of a human or animal subject that are susceptible to infection, such as, for example, to the gums, eyes, ears, skin, wounds, vaginal areas, groin areas, bed sores, burns, areas under medical dressings, diapers or other coverings which are likely to be moist, and the like.

For topical applications, the pharmaceutically acceptable carrier may take the form of liquids, creams, foams, lotions, ointments, suspensions, suppositories or gels, and may additionally comprise aqueous or organic solvents, buffering agents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration. In addition, the compositions of the invention may be impregnated in dressings or coverings for application to a subject.

In another embodiment of the invention, the compositions of the invention may be specifically designed for in vitro applications, such as disinfecting or sterilization of medical devices, contact lenses and the like, particularly where the devices or lenses are intended to be used in contact with a patient or wearer. For applications of this type, the compositions may be conveniently provided in the form of a liquid, cream, foam, lotion or gel, and may be provided with emulsifiers, surfactants, buffering agents, wetting agents, preservatives, and other components commonly found in compositions of this type. Compositions of the invention may be impregnated into absorptive materials, such as sutures, bandages, and gauze, or coated onto the surface of solid phase materials, such as staples, zippers and catheters to deliver the compositions to a site for the prevention of microbial infection. Other delivery systems of this type will be readily apparent to those skilled in the art.

Other components, such as an oxidase for peroxide generation, substrate for the oxidase and halide may be included, as desired, as described in detail above. In addition, the components may be formulated in a single formulation, or may be separated into binary formulations for later mixing during use, as may be desired for a particular application. For single formulations, one required system component which is available at the application site, such as halide, oxidase, prosthetic group for the oxidase, reducing substrate for the oxidase, or molecular oxygen is preferably left out of the formulation to preclude premature reaction and exhaustion of system components.

As an illustrative example, a composition suitable for use as an antimicrobial (or anti-infective) solution may comprise from about 1 to 50,000 µg/ml (i.e., from about 0.375 to about 18,750 GU/ml) of myeloperoxidase, from 0.1 to 500 µmol/mL (i.e., from 0.1 to 500 mM) of glycine, from 0.1 to 500 µmol/mL (i.e., from 0.1 to 500 mM) of D-isoleucine, from 0 to 100 µmol/mL (i.e., from 0 to 100 mM) of L-alanine, from 0.01 to 500 units of glucose oxidase, and from 50 to 500 mEq/L of chloride. The above composition is combined with from 1 to 500 µmol/mL (i.e., from 1 to 500 mM) of glucose or dextrose and used as a liquid disinfectant or sterilizing solution.

The foregoing may be better understood in connection with the following representative examples, which are presented for purposes of illustration and not by way of limitation.

EXAMPLES

Example 1

The Effect of L-Lysine on the Antimicrobial Activity of the Myeloperoxidase System Against *Staphylococcus aureus* in the Presence of Blood The effect of L-lysine on the activity of the myeloperoxidase system against *Staphylococcus aureus* was demonstrated as follows.

Materials

Bacterial suspensions, specifically *Staphylococcus aureus* in this example, were prepared by the shake flask method to achieve late log to early stationary phase growth. Bacteria were grown 24 hours in trypticase soy broth (TSB) at 35° C. The cultures were centrifuged at 4,000 rpm for 10 minutes and the supernatants removed. The pellet was collected and washed twice with sterile 0.9% normal saline (NS). The washed microorganisms were suspended and diluted with normal saline to a 3 McFarland standard, i.e., approximately $10^9$ bacteria colony forming units (CFU) per mL. Actual colony counts are confirmed by serial dilutions ($10^{-1}$ to $10^{-5}$ or $10^{-6}$) plated on TSA and incubated overnight at 35° C. To obtain an approximate final working target inoculum of $10^7$ CFU/mL, 15 microliters of organisms per mL of final reaction mixture are used.

Glucose oxidase (GO) from *Aspergillus Niger* was purchased from Biozyme, Inc., UK, Cat #GO3A, 270 U/mg). Porcine Myeloperoxidase (p-MPO) (Exoxemis, Inc., Little Rock, Ark. U.S.A., 375 U/mg). Sterile stock solutions of D-glucose and sodium chloride were prepared and used at a final concentration of 150 mM each. L-Lysine hydrochloride (Spectrum Chemical Cat #L1142) was prepared as a 100 mM stock solution. Catalase (Sigma, Cat #C-40) was prepared as a 1% stock solution in sterile 0.9% normal saline. Blood was collected by venipuncture and used as whole blood within the same day.

Methodology

Using sterile techniques, p-MPO and glucose oxidase solutions were prepared at concentrations indicated in Table 1 from 20 mM phosphate buffer at pH 6.5 containing 0.02% Tween-80, 150 mEq/L chloride and L-lysine at either 0, 1.25, 5, or 20 µmol/mL. *Staphylococcus aureus* were used to give a final target concentration of $2-3\times10^7$ CFU (7.4 log 10) per mL and venous whole blood was used to give a final concentration of 3%. Glucose was added to the reaction mixtures to a final concentration of 150 mM, which initiated the microbicidal reaction. The final volume of the reaction mixtures was 1 mL. The reactions were allowed to run from 30 minutes to 2 hours, as needed, at room temperature or at 37° C. in a dry bath. At the specified time points the reaction mixtures were treated with 100 microliters of a catalase solution, containing a minimum of 100 units/µL, to consume remaining peroxide and terminate the oxidative killing. Serial dilution plate counts were performed from the contents of each vial in sterile saline and inoculated onto trypticase soy agar (TSA) for quantitative culture. Plates were then incubated at 37° C. and counts taken at 24 hours. After incubation, the colony forming units (CFU) were counted as a measure of the viability of the organisms and results compared to an inoculum control. The results are shown in Table 1, as the average of 2 replicates.

TABLE 1

Effect of L-Lysine on the Microbicidal Activity of the Myeloperoxidase System Against *Staphylococcus aureus* in the Presence of Blood

| L-Lysine Conc mM | MPO U/ml | GO U/ml | Average Viability CFU/ml 30 min | Average Viability CFU/ml 60 min | Log Reduction 30 min | Log Reduction 60 min |
| --- | --- | --- | --- | --- | --- | --- |
| 0 | 38 | 3.3 | 6300000 | | 0.6 | |
| 0 | 38 | 3.3 | | 700000 | | 1.5 |
| 5 | 38 | 3.3 | 6050 | | 3.6 | |
| 5 | 38 | 3.3 | | 770 | | 4.5 |
| 20 | 38 | 3.3 | 6450 | | 3.6 | |
| 20 | 38 | 3.3 | | 620 | | 4.6 |

TABLE 1-continued

Effect of L-Lysine on the Microbicidal Activity of the Myeloperoxidase System Against *Staphylococcus aureus* in the Presence of Blood

| L-Lysine Conc mM | MPO U/ml | GO U/ml | Average Viability CFU/ml 30 min | Average Viability CFU/ml 60 min | Log Reduction 30 min | Log Reduction 60 min |
|---|---|---|---|---|---|---|
| 0 | 38 | 33.3 | 435000 | | 1.8 | |
| 0 | 38 | 33.3 | | 4650 | | 3.7 |
| 5 | 38 | 33.3 | 7 | | 6.5 | |
| 5 | 38 | 33.3 | | 3 | | 6.8 |
| 20 | 38 | 33.3 | 5 | | 6.6 | |
| 20 | 38 | 33.3 | | 5 | | 6.6 |
| 0 | 9 | 0.833 | 8550000 | | 0.5 | |
| 0 | 9 | 0.833 | | 6350000 | | 0.6 |
| 1.25 | 9 | 0.833 | 5050000 | | 0.7 | |
| 1.25 | 9 | 0.833 | | 620000 | | 1.6 |
| 5 | 9 | 0.833 | 775000 | | 1.5 | |
| 5 | 9 | 0.833 | | 53000 | | 2.7 |
| 0 | 9 | 8.33 | 6150000 | | 0.6 | |
| 0 | 9 | 8.33 | | 5050000 | | 0.7 |
| 1.25 | 9 | 8.33 | 6200000 | | 0.6 | |
| 1.25 | 9 | 8.33 | | 4950 | | 3.7 |
| 5 | 9 | 8.33 | 675000 | | 1.6 | |
| 5 | 9 | 8.33 | | 47 | | 5.7 |
| 0[1] | 0 | 0 | | 25050000 | | 0.0 |

[1]Control performed in the absence of blood, amino acid, glucose, MPO and glucose oxidase.

As shown in Table 1, MPO plus glucose oxidase exhibits potent microbicidal activity in the presence of the amino acid (AA) L-lysine. This combination killed 10 (7) *Staphylococcus aureus* in the presence of 3% blood, whereas the identical combination without L-lysine gave significantly less kill.

Example 2

The Effect of Amino Acids as Potential Enhancing Agents for the Antimicrobial Activity of the Myeloperoxidase System Against *Staphylococcus aureus* in the Presence of Blood The effect of various amino acids and amino acid homologues, as potential enhancing agents for MPO microbicidal action in the presence of blood, was demonstrated by following the general procedure of Example 1, except that each amino acid tested used a single concentration of p-MPO (714 pmol/mL, which is equivalent to 100 µg/mL or 38 U/mL) and a single concentration of glucose oxidase (33.3 U/mL). The individual amino acids, indicated in Tables 2-6 below, were tested at a single concentration of 5 µmol/mL and were compared to the MPO system without amino acids. The amino acids alone, in the absence of MPO were tested to rule out their microbicidal activity. The results are shown in Table 2 to Table 6, as the average of 2 replicates.

TABLE 2

Amino Acid Type: Effect on the Microbicidal Activity of the Myeloperoxidase System Against *Staphylococcus aureus* in the Presence of Blood

| Amino Acid name | Amino Acid Conc mM | MPO U/ml | GO U/ml | Average Viability CFU/ml 60 min | Log 10 (CFU + 1) Survivors 60 min | Log Reduction 60 min |
|---|---|---|---|---|---|---|
| L-Alanine | 5 | 38 | 33.3 | 7 | 0.9 | 6.5 |
| L-Arginine | 5 | 38 | 33.3 | 5450000 | 6.7 | 0.6 |
| L-Cysteine | 5 | 38 | 33.3 | 17400000 | 7.2 | 0.1 |
| L-Glutamic acid | 5 | 38 | 33.3 | 236 | 2.4 | 5.0 |
| L-Glutamine | 5 | 38 | 33.3 | 286 | 2.5 | 4.9 |
| Glycine | 5 | 38 | 33.3 | 0 | 0.0 | 7.4 |
| L-Histidine | 5 | 38 | 33.3 | 48000 | 4.7 | 2.7 |
| L-Lysine | 5 | 38 | 33.3 | 0 | 0.0 | 7.4 |
| L-Methionine | 5 | 38 | 33.3 | 6600000 | 6.8 | 0.6 |
| L-Phenylalanine | 5 | 38 | 33.3 | 0 | 0.0 | 7.4 |
| L-Proline | 5 | 38 | 33.3 | 4850 | 3.7 | 3.7 |
| L-Serine | 5 | 38 | 33.3 | 0 | 0.0 | 7.4 |
| L-Threonine | 5 | 38 | 33.3 | 630000 | 5.8 | 1.6 |
| L-Tryptophan | 5 | 38 | 33.3 | 21150000 | 7.3 | 0.1 |
| L-Valine | 5 | 38 | 33.3 | 0 | 0.0 | 7.4 |
| none | 0 | 38 | 33.3 | 5200000 | 6.7 | 0.7 |
| none[1] | 0 | 0 | 0 | 23950000 | 7.4 | 0.0 |

[1]Control performed in the absence of blood, amino acid, glucose, MPO and glucose oxidase.

TABLE 3

Amino Acid Type: Effect on the Microbicidal Activity of the Myeloperoxidase System Against *Staphylococcus aureus* in the Presence of Blood

| Amino Acid name | Amino Acid Concc mM | MPO U/ml | GO U/ml | Average Viability CFU/ml 60 min | Log 10 (CFU + 1) Survivors 60 min | Log Reduction 60 min |
|---|---|---|---|---|---|---|
| L-Leucine | 5 | 38 | 33.3 | 0 | 0.0 | 7.3 |
| L-Isoleucine | 5 | 38 | 33.3 | 0 | 0.0 | 7.3 |
| L-Aspartic acid | 5 | 38 | 33.3 | 620000 | 5.8 | 1.5 |
| L-Asparagine | 5 | 38 | 33.3 | 5950000 | 6.8 | 0.6 |

TABLE 3-continued

Amino Acid Type: Effect on the Microbicidal Activity of the Myeloperoxidase System Against *Staphylococcus aureus* in the Presence of Blood

| Amino Acid name | Amino Acid Concc mM | MPO U/ml | GO U/ml | Average Viability CFU/ml 60 min | Log 10 (CFU + 1) Survivors 60 min | Log Reduction 60 min |
|---|---|---|---|---|---|---|
| L-Hydroxyproline | 5 | 38 | 33.3 | 0 | 0.0 | 7.3 |
| L-Ornithine | 5 | 38 | 33.3 | 0 | 0.0 | 7.3 |
| L-Tyrosine | 5 | 38 | 33.3 | 630000 | 5.8 | 1.5 |
| D-Alanine | 5 | 38 | 33.3 | 0 | 0.0 | 7.3 |
| Alanine anhydride | 5 | 38 | 33.3 | 845000 | 5.9 | 1.4 |
| Glycine anhydride | 5 | 38 | 33.3 | 830000 | 5.9 | 1.4 |
| Taurine | 5 | 38 | 33.3 | 830000 | 5.9 | 1.4 |
| D-Threonine | 5 | 38 | 33.3 | 815000 | 5.9 | 1.4 |
| Pyruvic acid | 5 | 38 | 33.3 | 4900000 | 6.7 | 0.6 |
| Hippuric acid | 5 | 38 | 33.3 | 865000 | 5.9 | 1.4 |
| Nicotinic acid | 5 | 38 | 33.3 | 4150000 | 6.6 | 0.7 |
| none | 0 | 38 | 33.3 | 5550000 | 6.7 | 0.6 |
| none[1] | 0 | 0 | 0 | 22000000 | 7.3 | 0.0 |

[1]Control performed in the absence of blood, amino acid, glucose, MPO and glucose oxidase.

TABLE 4

Amino Acid Type: Effect on the Microbicidal Activity of the Myeloperoxidase System Against *Staphylococcus aureus* in the Presence of Blood

| Amino Acid name | Amino Acid Conc mM | MPO U/ml | GO U/ml | Average Viability CFU/ml 60 min | Log Reduction 60 min |
|---|---|---|---|---|---|
| Beta alanine | 5 | 38 | 33.3 | 0 | 7.4 |
| L-Ala methyl ester | 5 | 38 | 33.3 | 0 | 7.4 |
| L-Ala-L-ala | 5 | 38 | 33.3 | 238500 | 2.0 |
| Glyoxylic acid | 5 | 38 | 33.3 | 610000 | 1.6 |
| D-Proline | 5 | 38 | 33.3 | 830 | 4.5 |
| D-Leucine | 5 | 38 | 33.3 | 66550 | 2.6 |
| D-Lysine | 5 | 38 | 33.3 | 5050000 | 0.7 |
| D-Glutamic acid | 5 | 38 | 33.3 | 955000 | 1.4 |
| D-Tryptophan | 5 | 38 | 33.3 | 19700000 | 0.1 |
| none | 0 | 38 | 33.3 | 665000 | 1.6 |
| none[1] | 0 | 0 | 0 | 26150000 | 0.0 |

[1]Control performed in the absence of blood, amino acid, glucose, MPO and glucose oxidase.

TABLE 5

Amino Acid Type: Effect on the Microbicidal Activity of the Myeloperoxidase System Against *Staphylococcus aureus* in the Presence of Blood

| Amino Acid 1 name | AA 1 Conc mM | MPO U/ml | GO U/ml | Average Viability CFU/ml 60 min | Log Reduction 60 min |
|---|---|---|---|---|---|
| D-Glutamine | 5 | 38 | 33.3 | 18 | 6.1 |
| D-Isoleucine | 5 | 38 | 33.3 | 0 | 7.4 |
| D-Ornithine | 5 | 38 | 33.3 | 0 | 7.4 |
| D-Phenylalanine | 5 | 38 | 33.3 | 0 | 7.4 |
| D-Serine | 5 | 38 | 33.3 | 0 | 7.4 |
| D-Valine | 5 | 38 | 33.3 | 0 | 7.4 |
| D-Arginine | 5 | 38 | 33.3 | 0 | 7.4 |
| D-Aspartic acid | 5 | 38 | 33.3 | 570000 | 1.6 |
| D-Methionine | 5 | 38 | 33.3 | 9400000 | 0.4 |
| D-Histidine | 5 | 38 | 33.3 | 10900 | 3.4 |
| D-Tyrosine | 5 | 38 | 33.3 | 9400 | 3.4 |
| none | 0 | 38 | 33.3 | 400000 | 1.8 |
| none | 0 | 0 | 0 | 24700000 | 0.0 |

As a control to determine the microbicidal activity of the amino acids alone, the procedure of Example 2 was followed without replication, except in the absence of glucose, MPO, and glucose oxidase. The results are shown in Table 6.

TABLE 6

Amino Acid Type: Microbicidal Activity of the Amino Acid Alone Against *Staphylococcus aureus* in the Presence of Blood

| Amino Acid name | Amino Acid Conc mM | MPO U/ml | GO U/ml | Average Viability CFU/ml 60 min | Log Reduction 60 min |
|---|---|---|---|---|---|
| L-Alanine | 5 | 0 | 0 | 24100000 | 0.0 |
| L-Arginine | 5 | 0 | 0 | 23600000 | 0.0 |
| L-Cysteine | 5 | 0 | 0 | 22400000 | 0.0 |
| L-Glutamic acid | 5 | 0 | 0 | 23700000 | 0.0 |
| L-Glutamine | 5 | 0 | 0 | 24100000 | 0.0 |
| Glycine | 5 | 0 | 0 | 25300000 | 0.0 |
| L-Histidine | 5 | 0 | 0 | 22700000 | 0.0 |
| L-Lysine | 5 | 0 | 0 | 21400000 | 0.0 |
| L-Methionine | 5 | 0 | 0 | 19800000 | 0.1 |
| L-Phenylalanine | 5 | 0 | 0 | 22400000 | 0.0 |
| L-Proline | 5 | 0 | 0 | 21600000 | 0.0 |
| L-Serine | 5 | 0 | 0 | 24100000 | 0.0 |
| L-Threonine | 5 | 0 | 0 | 23300000 | 0.0 |
| L-Tryptophan | 5 | 0 | 0 | 21600000 | 0.0 |
| L-Valine | 5 | 0 | 0 | 23100000 | 0.0 |
| L-Leucine | 5 | 0 | 0 | 18700000 | 0.1 |
| L-Isoleucine | 5 | 0 | 0 | 20500000 | 0.0 |
| L-Aspartic acid | 5 | 0 | 0 | 18600000 | 0.1 |
| L-Asparagine | 5 | 0 | 0 | 21800000 | 0.0 |
| L-Hydroxyproline | 5 | 0 | 0 | 20400000 | 0.0 |
| L-Ornithine | 5 | 0 | 0 | 19200000 | 0.1 |
| L-Tyrosine | 5 | 0 | 0 | 21600000 | 0.0 |
| D-Alanine | 5 | 0 | 0 | 19600000 | 0.0 |
| Alanine anhydride | 5 | 0 | 0 | 21900000 | 0.0 |
| Glycine anhydride | 5 | 0 | 0 | 20100000 | 0.0 |
| Taurine | 5 | 0 | 0 | 21600000 | 0.0 |
| D-Threonine | 5 | 0 | 0 | 20700000 | 0.0 |
| Pyruvic acid | 5 | 0 | 0 | 22100000 | 0.0 |
| Hippuric acid | 5 | 0 | 0 | 19700000 | 0.0 |
| Nicotinic acid | 5 | 0 | 0 | 23200000 | 0.0 |
| Beta alanine | 5 | 0 | 0 | 25500000 | 0.0 |
| L-Ala methyl ester | 5 | 0 | 0 | 24300000 | 0.0 |
| L-Ala-L-ala | 5 | 0 | 0 | 26100000 | 0.0 |
| Glyoxylic acid | 5 | 0 | 0 | 22200000 | 0.1 |
| D-proline | 5 | 0 | 0 | 21400000 | 0.1 |
| D-Leucine | 5 | 0 | 0 | 24400000 | 0.0 |
| D-Lysine | 5 | 0 | 0 | 25100000 | 0.0 |
| D-Glutamic acid | 5 | 0 | 0 | 26200000 | 0.0 |
| D-Tryptophan | 5 | 0 | 0 | 22600000 | 0.1 |
| D-Glutamine | 5 | 0 | 0 | 20500000 | 0.1 |

TABLE 6-continued

Amino Acid Type: Microbicidal Activity of the Amino Acid Alone Against *Staphylococcus aureus* in the Presence of Blood

| Amino Acid name | Amino Acid Conc mM | MPO U/ml | GO U/ml | Average Viability CFU/ml 60 min | Log Reduction 60 min |
|---|---|---|---|---|---|
| D-Isoleucine | 5 | 0 | 0 | 21300000 | 0.1 |
| D-Ornithine | 5 | 0 | 0 | 20600000 | 0.1 |
| D-Phenylalanine | 5 | 0 | 0 | 24200000 | 0.0 |
| D-Serine | 5 | 0 | 0 | 23100000 | 0.0 |
| D-Valine | 5 | 0 | 0 | 20900000 | 0.1 |
| D-Arginine | 5 | 0 | 0 | 21500000 | 0.1 |
| D-Aspartic acid | 5 | 0 | 0 | 20900000 | 0.1 |
| D-Methionine | 5 | 0 | 0 | 21100000 | 0.1 |
| D-Histidine | 5 | 0 | 0 | 22300000 | 0.0 |
| D-Tyrosine | 5 | 0 | 0 | 23200000 | 0.0 |

Tables 2 through 5 show the performance of the MPO system with and without added amino acids. Table 6 shows that neither amino acids, nor homologues are microbicidal on their own in the absence of MPO.

The magnitude of the amino acid mediated improvement is dependent upon the amino acid used and ranges from zero to at least 6 logs improvement under the test conditions.

In Table 2, tests with representative L-amino acids demonstrate the increased activity of the MPO system when used with amino acids. The notable exceptions are cysteine, methionine, and tryptophan, which are amino acids that would be expected to chemically react with the oxidative intermediates produced by the MPO system, generating inactive compounds. The limited enhancing activity of histidine could be explained by the fact that it would be expected to be highly reactive to singlet oxygen and is consumed by the product of the MPO system.

Tables 3 and 4 have additional L-amino acids and show that esters and other close homologues of amino acids have demonstrable activity as well.

In Tables 3, 4 and 5, a number of D-amino acids were tested and as is the case for the L-amino acids, many are able to provide significant improvement to the microbicidal activity of the formulation. Note that D-arginine, shown in Table 5, is highly active in contrast to the essentially inactive L-arginine shown in Table 2.

In general, the aliphatic amino acids, especially those containing branched-chains are highly active.

In Table 6, all amino acids were tested alone, in the absence of MPO to rule out their microbicidal activity.

Example 3

The Effect of Amino Acid Analogues as Potential Enhancing Agents for the Antimicrobial Activity of the Myeloperoxidase System Against *Staphylococcus aureus* in the Presence of Blood The effect of various beta amino acids, ester derivatives, and N-substituted amino acids, as potential enhancing agents for p-MPO microbicidal action in the presence of blood, was demonstrated by following the general procedure of Example 2. The amino acid analogues alone, in the absence of MPO, were tested to rule out their microbicidal activity.

The results are shown in Table 7 and Table 8, below.

TABLE 7

Amino Acid Analogue Type: Effect on the Microbicidal Activity of the Myeloperoxidase System Against *Staphylococcus aureus* in the Presence of Blood

| Amino Acid name | Amino Acid Conc mM | MPO U/ml | GO U/ml | Average Viability CFU/ml 60 min | Log Reduction 60 min |
|---|---|---|---|---|---|
| Beta Amino Acids | | | | | |
| DL-Beta-homoleucine | 5 | 38 | 33.3 | 0 | 7.4 |
| 3-Aminobutanoic acid | 5 | 38 | 33.3 | 9 | 6.4 |
| DL-2,3-Diaminopropionic acid monohydrochloride | 5 | 38 | 33.3 | 0 | 7.4 |
| DL-3-Aminoisobutyric acid | 5 | 38 | 33.3 | 0 | 7.4 |
| Beta-Alanine ethyl ester hydrochloride | 5 | 38 | 33.3 | 1195000 | 1.3 |
| Ethyl 3-aminobutyrate | 5 | 38 | 33.3 | 0 | 7.4 |
| Ester Amino Acids | | | | | |
| L-Lysine methyl ester dihydrochloride | 5 | 38 | 33.3 | 0 | 7.4 |
| L-Tyrosine methyl ester hydrochloride | 5 | 38 | 33.3 | 87000 | 2.4 |
| Glycine methyl ester hydrochloride | 5 | 38 | 33.3 | 0 | 7.4 |
| L-Valine ethyl ester hydrochloride | 5 | 38 | 33.3 | 0 | 7.4 |
| Ethyl 2-aminopropanoate | 5 | 38 | 33.3 | 0 | 7.4 |
| N-Substituted Amino Acids | | | | | |
| Sarcosine methyl ester hydrochloride | 5 | 38 | 33.3 | 0 | 7.4 |
| L-Proline methyl ester hydrochloride | 5 | 38 | 33.3 | 0 | 7.4 |
| Nipecotic acid | 5 | 38 | 33.3 | 0 | 7.4 |
| none[1] | 0 | 0 | 0 | 23150000 | 0.0 |

[1]Control performed in the absence of blood, amino acid, glucose, MPO and glucose oxidase.

As a control to determine the microbicidal activity of the amino acids alone, the foregoing procedure was followed without replication, except in the absence of glucose, MPO, and glucose oxidase. The results are shown in Table 8.

TABLE 8

Amino Acid Analogue Type: Microbicidal Activity of the Amino Acid Analogue Alone Against *Staphylococcus aureus* in the Presence of Blood

| Amino Acid name | Amino Acid Conc mM | MPO U/ml | GO U/ml | Average Viability CFU/ml 60 min | Log Reduction 60 min |
|---|---|---|---|---|---|
| Beta Amino Acids | | | | | |
| DL-Beta-homoleucine | 5 | 0 | 0 | 20500000 | 0.0 |
| 3-Aminobutanoic acid | 5 | 0 | 0 | 21300000 | 0.0 |
| DL-2,3-Diaminopropionic acid monohydrochloride | 5 | 0 | 0 | 20600000 | 0.0 |
| DL-3-Aminoisobutyric acid | 5 | 0 | 0 | 24200000 | 0.0 |
| Beta-Alanine ethyl ester hydrochloride | 5 | 0 | 0 | 23100000 | 0.0 |
| Ethyl 3-aminobutyrate | 5 | 0 | 0 | 20900000 | 0.0 |
| Ester Amino Acids | | | | | |
| L-Lysine methyl ester dihydrochloride | 5 | 0 | 0 | 21500000 | 0.0 |
| L-Tyrosine methyl ester hydrochloride | 5 | 0 | 0 | 20900000 | 0.0 |
| Glycine methyl ester hydrochloride | 5 | 0 | 0 | 21100000 | 0.0 |
| L-Valine ethyl ester hydrochloride | 5 | 0 | 0 | 22300000 | 0.0 |
| Ethyl 2-aminopropanoate | 5 | 0 | 0 | 23200000 | 0.0 |
| N-Substituted Amino Acids | | | | | |
| Sarcosine methyl ester hydrochloride | 5 | 0 | 0 | 23200000 | 0.0 |
| L-Proline methyl ester hydrochloride | 5 | 0 | 0 | 23200000 | 0.0 |
| Nipecotic acid | 5 | 0 | 0 | 23200000 | 0.0 |

As shown in Table 7 and Table 8, the MPO system exhibits potent microbicidal activity in the presence of most of the amino acids homologues tested. Most of the compounds selected to represent beta amino acid, ester amino acid, and N-substituted amino acid homologues achieved $10^7$ CFU kill of *Staphylococcus aureus* in the presence of 3% blood, whereas identical test conditions without amino acids gave less than 1.5 log reduction, as shown in Table 2 through Table 5. Amino acids alone do not exhibit any microbicidal activity as shown in Table 8.

Example 4

The general procedure of Example 2 was followed for various amino acids using MPO at concentrations of 25 or 100 μg/mL and the amino acids at concentrations of 1.25, 5 or 20 μmol/mL (mM) for time periods of 30 or 60 minutes before reaction quenching with catalase. The Log 10 (CFU+1) of organism survivors for each of the amino acids and conditions is shown in the following Table 9 ranked in decreasing effectiveness order of the average results of the test conditions.

TABLE 9

Effect of Amino Acids on the Microbicidal Activity of the Myeloperoxidase System Against *Staphylococcus aureus* at Varying Concentration and Time Conditions

| Test Conditions: | | | | | | | | | |
|---|---|---|---|---|---|---|---|---|---|
| MPO (μg/mL) | 100 | 100 | 100 | 100 | 25 | 25 | 25 | 25 | |
| AA (mM) | 20 | 20 | 5 | 5 | 5 | 5 | 1.25 | 1.25 | |
| time (min) | 30 | 60 | 30 | 60 | 30 | 60 | 30 | 60 | |
| Amino Acid: | Log 10 (CFU + 1) Survivors | | | | | | | | Ave rank |
| Beta alanine | 0.0 | 0.0 | 0.0 | 0.0 | 0.0 | 0.0 | 0.0 | 0.0 | 1.000 |
| D-Alanine methyl ester | 0.0 | 0.0 | 0.0 | 0.0 | 0.0 | 0.0 | 0.0 | 0.0 | 1.000 |
| L-Isoleucine | 0.0 | 0.0 | 0.0 | 0.0 | 0.0 | 0.0 | 2.1 | 0.0 | 1.250 |
| L-Leucine | 0.0 | 0.0 | 0.0 | 0.0 | 4.1 | 0.0 | 3.9 | 0.0 | 2.000 |
| L-Valine | 0.0 | 0.0 | 0.0 | 0.0 | 4.7 | 0.0 | 4.8 | 0.0 | 2.375 |
| D-Valine | 0.0 | 0.0 | 0.0 | 0.0 | 4.1 | 0.0 | 6.7 | 0.0 | 2.625 |
| D-Isoleucine | 0.0 | 0.0 | 0.0 | 0.0 | 0.0 | 0.0 | 6.0 | 1.1 | 2.625 |
| D-Phenylalanine | 0.0 | 0.0 | 0.0 | 0.0 | 5.1 | 0.0 | 7.2 | 4.9 | 6.500 |
| L-Phenylalanine | 0.0 | 0.0 | 0.0 | 0.0 | 7.1 | 0.0 | 7.0 | 4.9 | 7.500 |
| L-Serine | 5.8 | 0.0 | 5.0 | 0.0 | 5.0 | 0.0 | 6.8 | 1.8 | 8.000 |
| L-Alanine methyl ester | 0.0 | 0.0 | 0.0 | 0.0 | 7.3 | 0.0 | 7.3 | 0.0 | 8.625 |
| L-Ornithine | 6.9 | 0.0 | 6.7 | 0.0 | 7.2 | 0.0 | 7.3 | 0.0 | 12.375 |
| L-Alanine | 6.1 | 0.0 | 5.1 | 0.0 | 6.9 | 4.1 | 7.0 | 4.7 | 12.875 |
| D-Leucine | 1.8 | 1.9 | 2.7 | 2.0 | 3.8 | 2.2 | 6.7 | 2.1 | 13.625 |
| L-Proline | 5.8 | 0.0 | 4.9 | 0.0 | 7.1 | 3.9 | 7.0 | 6.8 | 14.000 |
| L-Lysine 261 | 0.8 | 0.8 | 0.9 | 0.5 | 5.8 | 1.6 | 6.8 | 3.7 | 14.125 |
| D-Ornithine | 6.8 | 0.0 | 5.1 | 0.0 | 7.3 | 3.9 | 7.3 | 5.7 | 15.500 |
| D-Serine | 6.0 | 3.9 | 6.0 | 0.0 | 6.8 | 6.5 | 6.7 | 6.0 | 15.625 |
| D-Proline | 4.8 | 0.0 | 5.7 | 2.7 | 6.9 | 2.4 | 7.3 | 3.7 | 16.125 |
| D-Tyrosine | 5.8 | 0.0 | 6.7 | 5.0 | 6.8 | 5.9 | 6.7 | 7.0 | 18.125 |
| Glycine | 7.0 | 0.0 | 6.0 | 0.0 | 7.2 | 6.8 | 7.3 | 6.9 | 19.625 |

TABLE 9-continued

Effect of Amino Acids on the Microbicidal Activity of the Myeloperoxidase System
Against *Staphylococcus aureus* at Varying Concentration and Time Conditions

| | | | | | | | | | |
|---|---|---|---|---|---|---|---|---|---|
| D-Arginine | 7.0 | 6.8 | 6.9 | 0.0 | 6.9 | 6.7 | 7.0 | 5.9 | 20.000 |
| D-Histidine | 6.8 | 3.9 | 5.1 | 4.1 | 7.0 | 6.0 | 6.9 | 5.8 | 20.125 |
| D-Glutamine | 6.8 | 4.0 | 5.0 | 0.0 | 7.3 | 7.0 | 7.2 | 7.0 | 21.375 |
| D-Alanine | 7.3 | 0.0 | 6.8 | 0.6 | 7.3 | 3.7 | 7.3 | 6.7 | 22.500 |
| Hippuric acid | 6.8 | 5.0 | 7.3 | 5.9 | 7.3 | 5.9 | 6.7 | 5.8 | 24.875 |
| L-Glutamine | 7.0 | 5.2 | 7.2 | 0.0 | 7.3 | 7.1 | 6.8 | 7.0 | 25.000 |
| L-Aspartic acid | 7.0 | 6.8 | 7.0 | 5.8 | 7.1 | 7.0 | 7.0 | 6.9 | 26.375 |
| L-Glutamic acid | 7.3 | 6.0 | 6.9 | 2.8 | 7.1 | 7.0 | 7.3 | 6.7 | 26.875 |
| L-Threonine | 7.3 | 7.3 | 7.1 | 5.5 | 7.3 | 7.1 | 7.3 | 6.7 | 29.625 |
| D-Threonine | 7.4 | 5.0 | 7.1 | 5.1 | 7.3 | 6.8 | 7.3 | 6.7 | 29.750 |
| L-Alanine anhydride | 7.1 | 6.0 | 7.2 | 5.8 | 7.2 | 7.3 | 7.2 | 7.2 | 30.250 |
| L-Hydroxyproline | 7.2 | 7.3 | 7.2 | 0.9 | 7.3 | 7.3 | 7.4 | 6.1 | 30.625 |
| L-Histidine | 7.3 | 7.3 | 6.8 | 4.7 | 7.3 | 7.3 | 7.3 | 7.3 | 32.125 |
| Taurine | 7.3 | 5.1 | 7.3 | 5.0 | 7.3 | 7.0 | 7.3 | 7.1 | 32.625 |
| Glycine anhydride | 7.0 | 6.9 | 7.3 | 5.9 | 7.4 | 7.2 | 7.3 | 7.0 | 33.000 |
| L-Tyrosine | 7.3 | 7.2 | 7.3 | 5.8 | 7.3 | 7.1 | 7.3 | 7.0 | 33.250 |

Example 5

The Effect of Two-Way Combinations of Amino Acids on the Antimicrobial Activity of the Myeloperoxidase System Against *Staphylococcus aureus* in the Presence of Blood The effect of two-way combinations of amino acids, as potential enhancing agents for p-MPO microbicidal action in the presence of blood, was demonstrated by following the general procedure of Example 2, except that each test contained a single low concentration of MPO (12.5 µg/mL or 4.7 U/mL) and glucose oxidase (4.2 U/mL), and two amino acid activators, as indicated in Tables 9 through 13 below, each added to the mixtures at a final concentration of 1.25 µmol/mL. When the amino acid enhancers are tested individually for comparison, they are added to the mixtures at a final concentration of 2.5 µmol/mL.

The results are shown below.

TABLE 10

Effect of Two-Way Combinations of Amino Acids on the
Microbicidal Activity of the Myeloperoxidase System
Against *Staphylococcus aureus* in the Presence of Blood

| Amino Acid 1 name | AA 1 Conc mM | Amino Acid 2 name | AA 2 Conc mM | MPO U/ml | GO U/ml | Average Viability CFU/ml 50 min | Log Reduction 50 min |
|---|---|---|---|---|---|---|---|
| D-Tyrosine | 1.25 | L-Leucine | 1.25 | 4.7 | 4.2 | 5050000 | 0.7 |
| D-Tyrosine | 1.25 | D-Glutamine | 1.25 | 4.7 | 4.2 | 11050000 | 0.3 |
| D-Tyrosine | 1.25 | L-Serine | 1.25 | 4.7 | 4.2 | 11250000 | 0.3 |
| D-Valine | 1.25 | L-Proline | 1.25 | 4.7 | 4.2 | 10100000 | 0.4 |
| D-Valine | 1.25 | L-Histidine | 1.25 | 4.7 | 4.2 | 12600000 | 0.3 |
| Glycine | 1.25 | D-Phenylalanine | 1.25 | 4.7 | 4.2 | 4250000 | 0.8 |
| L-Ala methyl ester | 1.25 | D-Phenylalanine | 1.25 | 4.7 | 4.2 | 11900000 | 0.3 |
| L-Aspartic acid | 1.25 | L-Alanine | 1.25 | 4.7 | 4.2 | 11350000 | 0.3 |
| L-Aspartic acid | 1.25 | L-Glutamic acid | 1.25 | 4.7 | 4.2 | 13150000 | 0.3 |
| L-Glutamic acid | 1.25 | D-Arginine | 1.25 | 4.7 | 4.2 | 12500000 | 0.3 |
| L-Glutamine | 1.25 | L-Valine | 1.25 | 4.7 | 4.2 | 11800000 | 0.3 |
| L-Glutamine | 1.25 | L-Ala methyl ester | 1.25 | 4.7 | 4.2 | 12500000 | 0.3 |
| L-Glutamine | 1.25 | D-Valine | 1.25 | 4.7 | 4.2 | 14850000 | 0.2 |
| Glycine | 1.25 | L-Valine | 1.25 | 4.7 | 4.2 | 910 | 4.4 |
| L-Histidine | 1.25 | L-Ornithine | 1.25 | 4.7 | 4.2 | 12250000 | 0.3 |
| L-Hydroxyproline | 1.25 | D-Glutamine | 1.25 | 4.7 | 4.2 | 13750000 | 0.3 |
| L-Isoleucine | 1.25 | D-Phenylalanine | 1.25 | 4.7 | 4.2 | 4850000 | 0.7 |
| L-Leucine | 1.25 | L-Glutamic acid | 1.25 | 4.7 | 4.2 | 8200000 | 0.5 |
| L-Lysine | 1.25 | L-Glutamic acid | 1.25 | 4.7 | 4.2 | 12050000 | 0.3 |
| L-Ornithine | 1.25 | L-Phenylalanine | 1.25 | 4.7 | 4.2 | 5950000 | 0.6 |
| none | 0 | D-Tyrosine | 2.5 | 4.7 | 4.2 | 1320000 | 1.3 |
| none | 0 | L-Leucine | 2.5 | 4.7 | 4.2 | 214500 | 2.1 |
| none | 0 | D-Glutamine | 2.5 | 4.7 | 4.2 | 14750000 | 0.2 |
| none | 0 | L-Serine | 2.5 | 4.7 | 4.2 | 1175000 | 1.3 |
| none | 0 | D-Valine | 2.5 | 4.7 | 4.2 | 630000 | 1.6 |
| none | 0 | L-Proline | 2.5 | 4.7 | 4.2 | 1235000 | 1.3 |

TABLE 10-continued

Effect of Two-Way Combinations of Amino Acids on the Microbicidal Activity of the Myeloperoxidase System Against *Staphylococcus aureus* in the Presence of Blood

| Amino Acid 1 name | AA 1 Conc mM | Amino Acid 2 name | AA 2 Conc mM | MPO U/ml | GO U/ml | Average Viability CFU/ml 50 min | Log Reduction 50 min |
|---|---|---|---|---|---|---|---|
| none | 0 | L-Histidine | 2.5 | 4.7 | 4.2 | 7000000 | 0.5 |
| none | 0 | Glycine | 2.5 | 4.7 | 4.2 | 9100 | 3.4 |
| none | 0 | D-Phenylalanine | 2.5 | 4.7 | 4.2 | 7950000 | 0.5 |
| none | 0 | L-Ala methyl ester | 2.5 | 4.7 | 4.2 | 7250000 | 0.5 |
| none | 0 | L-Aspartic acid | 2.5 | 4.7 | 4.2 | 6900000 | 0.6 |
| none | 0 | L-Alanine | 2.5 | 4.7 | 4.2 | 9750000 | 0.4 |
| none | 0 | L-Glutamic acid | 2.5 | 4.7 | 4.2 | 10850000 | 0.4 |
| none | 0 | D-Arginine | 2.5 | 4.7 | 4.2 | 14200000 | 0.2 |
| none | 0 | L-Glutamine | 2.5 | 4.7 | 4.2 | 14350000 | 0.2 |
| none | 0 | L-Valine | 2.5 | 4.7 | 4.2 | 104500 | 2.4 |
| none | 0 | L-Ornithine | 2.5 | 4.7 | 4.2 | 18250000 | 0.1 |
| none | 0 | L-Hydroxyproline | 2.5 | 4.7 | 4.2 | 13100000 | 0.3 |
| none | 0 | L-Isoleucine | 2.5 | 4.7 | 4.2 | 159500 | 2.2 |
| none | 0 | L-Lysine | 2.5 | 4.7 | 4.2 | 16200000 | 0.2 |
| none | 0 | L-Phenylalanine | 2.5 | 4.7 | 4.2 | 10550000 | 0.4 |
| none[1] | 0 | none | 0 | 0 | 0 | 25050000 | 0.0 |

[1] Control performed in the absence of blood, amino acid, glucose, MPO and glucose oxidase.

TABLE 11

Effect of Two-Way Combinations of Amino Acids on the Microbicidal Activity of the Myeloperoxidase System Against *Staphylococcus aureus* in the Presence of Blood

| Amino Acid 1 name | AA 1 Conc mM | Amino Acid 2 name | AA 2 Conc mM | MPO U/ml | GO U/ml | Average Viability CFU/ml 50 min | Log Reduction 50 min |
|---|---|---|---|---|---|---|---|
| D-Arginine | 1.25 | L-Phenylalanine | 1.25 | 4.7 | 4.2 | 6650000 | 0.6 |
| D-Arginine | 1.25 | D-Glutamine | 1.25 | 4.7 | 4.2 | 10850000 | 0.4 |
| D-Arginine | 1.25 | D-Histidine | 1.25 | 4.7 | 4.2 | 6050000 | 0.6 |
| D-Glutamine | 1.25 | D-Isoleucine | 1.25 | 4.7 | 4.2 | 8950000 | 0.5 |
| D-Histidine | 1.25 | D-Proline | 1.25 | 4.7 | 4.2 | 5100000 | 0.7 |
| D-Histidine | 1.25 | L-Histidine | 1.25 | 4.7 | 4.2 | 11250000 | 0.4 |
| D-Isoleucine | 1.25 | L-Leucine | 1.25 | 4.7 | 4.2 | 7750000 | 0.5 |
| D-Isoleucine | 1.25 | D-Phenylalanine | 1.25 | 4.7 | 4.2 | 4100000 | 0.8 |
| D-Leucine | 1.25 | L-Histidine | 1.25 | 4.7 | 4.2 | 10200000 | 0.4 |
| D-Leucine | 1.25 | D-Ala methyl ester | 1.25 | 4.7 | 4.2 | 7100000 | 0.6 |
| D-Ornithine | 1.25 | L-Isoleucine | 1.25 | 4.7 | 4.2 | 11850000 | 0.4 |
| D-Ornithine | 1.25 | L-Ornithine | 1.25 | 4.7 | 4.2 | 12850000 | 0.3 |
| D-Phenylalanine | 1.25 | L-Lysine | 1.25 | 4.7 | 4.2 | 8300000 | 0.5 |
| D-Proline | 1.25 | L-Lysine | 1.25 | 4.7 | 4.2 | 12350000 | 0.3 |
| D-Proline | 1.25 | D-Isoleucine | 1.25 | 4.7 | 4.2 | 10500000 | 0.4 |
| D-Proline | 1.25 | D-Leucine | 1.25 | 4.7 | 4.2 | 11600000 | 0.4 |
| D-Serine | 1.25 | D-Threonine | 1.25 | 4.7 | 4.2 | 12300000 | 0.3 |
| D-Serine | 1.25 | D-Glutamine | 1.25 | 4.7 | 4.2 | 12000000 | 0.4 |
| D-Threonine | 1.25 | L-Lysine | 1.25 | 4.7 | 4.2 | 11900000 | 0.4 |
| none | 0 | D-Arginine | 2.5 | 4.7 | 4.2 | 14650000 | 0.3 |
| none | 0 | L-Phenylalanine | 2.5 | 4.7 | 4.2 | 11100000 | 0.4 |
| none | 0 | D-Glutamine | 2.5 | 4.7 | 4.2 | 15500000 | 0.2 |
| none | 0 | D-Histidine | 2.5 | 4.7 | 4.2 | 8000000 | 0.5 |
| none | 0 | D-Isoleucine | 2.5 | 4.7 | 4.2 | 196000 | 2.1 |
| none | 0 | D-Proline | 2.5 | 4.7 | 4.2 | 1890000 | 1.2 |
| none | 0 | L-Histidine | 2.5 | 4.7 | 4.2 | 7000000 | 0.6 |
| none | 0 | L-Leucine | 2.5 | 4.7 | 4.2 | 200500 | 2.1 |
| none | 0 | D-Phenylalanine | 2.5 | 4.7 | 4.2 | 9300000 | 0.5 |
| none | 0 | D-Leucine | 2.5 | 4.7 | 4.2 | 313000 | 1.9 |
| none | 0 | D-Ala methyl ester | 2.5 | 4.7 | 4.2 | 9500000 | 0.5 |
| none | 0 | D-Ornithine | 2.5 | 4.7 | 4.2 | 17950000 | 0.2 |
| none | 0 | L-Isoleucine | 2.5 | 4.7 | 4.2 | 155500 | 2.2 |
| none | 0 | L-Ornithine | 2.5 | 4.7 | 4.2 | 17400000 | 0.2 |
| none | 0 | L-Lysine | 2.5 | 4.7 | 4.2 | 18900000 | 0.2 |

TABLE 11-continued

Effect of Two-Way Combinations of Amino Acids on the Microbicidal Activity of the Myeloperoxidase System Against *Staphylococcus aureus* in the Presence of Blood

| Amino Acid 1 name | AA 1 Conc mM | Amino Acid 2 name | AA 2 Conc mM | MPO U/ml | GO U/ml | Average Viability CFU/ml 50 min | Log Reduction 50 min |
|---|---|---|---|---|---|---|---|
| none | 0 | D-Serine | 2.5 | 4.7 | 4.2 | 945000 | 1.5 |
| none | 0 | D-Threonine | 2.5 | 4.7 | 4.2 | 2020000 | 1.1 |
| none | 0 | none | 0 | 0 | 0 | 26850000 | 0.0 |

Example 6

The Effect of Two Way Amino Acid Combinations Containing Glycine on the Antimicrobial Activity of the Myeloperoxidase System Against *Staphylococcus aureus* in the Presence of Blood Using the general procedure of Example 5, in which one of the two amino acids is glycine, yielded the results shown in Tables 12 and 13.

TABLE 12

Effect of Two-Way Combinations of Amino Acids with Glycine on the Microbicidal Activity of the Myeloperoxidase System Against *Staphylococcus aureus* in the Presence of Blood

| Amino Acid 1 name | AA 1 Conc mM | Amino Acid 2 name | AA 2 Conc mM | MPO U/ml | GO U/ml | Average Viability CFU/ml 50 min | Log Reduction 50 min |
|---|---|---|---|---|---|---|---|
| Glycine | 1.25 | Beta-alanine | 1.25 | 4.7 | 4.2 | 6800 | 3.5 |
| Glycine | 1.25 | L-Valine | 1.25 | 4.7 | 4.2 | 910 | 4.4 |
| Glycine | 1.25 | L-Leucine | 1.25 | 4.7 | 4.2 | 6900 | 3.5 |
| Glycine | 1.25 | L-Isoleucine | 1.25 | 4.7 | 4.2 | 975 | 4.4 |
| Glycine | 1.25 | D-Valine | 1.25 | 4.7 | 4.2 | 3330 | 3.8 |
| Glycine | 1.25 | D-Isoleucine | 1.25 | 4.7 | 4.2 | 0 | 7.4 |
| Glycine | 1.25 | D-Ala-methyl ester | 1.25 | 4.7 | 4.2 | 125500 | 2.3 |
| Glycine | 2.5 | none | 0 | 4.7 | 4.2 | 7050 | 3.5 |
| none | 0 | Beta-alanine | 2.5 | 4.7 | 4.2 | 505000 | 1.7 |
| none | 0 | L-Valine | 2.5 | 4.7 | 4.2 | 104500 | 2.4 |
| none | 0 | L-Leucine | 2.5 | 4.7 | 4.2 | 200500 | 2.1 |
| none | 0 | L-Isoleucine | 2.5 | 4.7 | 4.2 | 73000 | 2.5 |
| none | 0 | D-Valine | 2.5 | 4.7 | 4.2 | 630000 | 1.6 |
| none | 0 | D-Isoleucine | 2.5 | 4.7 | 4.2 | 196000 | 2.1 |
| none | 0 | D-Ala-methyl ester | 2.5 | 4.7 | 4.2 | 5450000 | 0.6 |
| none | 0 | none | 0 | 0 | 0 |  | 0.0 |

TABLE 13

Effect of Two-Way Combinations of Amino Acids with Glycine on the Microbicidal Activity of the Myeloperoxidase System Against *Staphylococcus aureus* in the Presence of Blood

| Amino Acid 1 name | AA 1 Conc mM | Amino Acid 2 name | AA 2 Conc mM | MPO U/ml | GO U/ml | Average Viability CFU/ml 50 min | Log Reduction 50 min |
|---|---|---|---|---|---|---|---|
| Glycine | 1.25 | L-Alanine | 1.25 | 4.7 | 4.2 | 209500 | 2.1 |
| Glycine | 1.25 | D-Alanine | 1.25 | 4.7 | 4.2 | 162500 | 2.2 |
| Glycine | 1.25 | L-Aspartic acid | 1.25 | 4.7 | 4.2 | 51000 | 2.7 |
| Glycine | 1.25 | L-Glutamic acid | 1.25 | 4.7 | 4.2 | 1100000 | 1.3 |
| Glycine | 1.25 | L-Glutamine | 1.25 | 4.7 | 4.2 | 765000 | 1.5 |
| Glycine | 1.25 | L-Histidine | 1.25 | 4.7 | 4.2 | 495000 | 1.7 |
| Glycine | 1.25 | L-Hydroxyproline | 1.25 | 4.7 | 4.2 | 4900000 | 0.7 |
| Glycine | 1.25 | D-Leucine | 1.25 | 4.7 | 4.2 | 90000 | 2.4 |
| Glycine | 1.25 | L-Lysine | 1.25 | 4.7 | 4.2 | 680000 | 1.6 |
| Glycine | 1.25 | L-Ornithine | 1.25 | 4.7 | 4.2 | 4600000 | 0.7 |
| Glycine | 1.25 | L-Proline | 1.25 | 4.7 | 4.2 | 162500 | 2.2 |
| Glycine | 1.25 | L-Serine | 1.25 | 4.7 | 4.2 | 99500 | 2.4 |

TABLE 13-continued

Effect of Two-Way Combinations of Amino Acids with Glycine
on the Microbicidal Activity of the Myeloperoxidase System Against
*Staphylococcus aureus* in the Presence of Blood

| Amino Acid 1 name | AA 1 Conc mM | Amino Acid 2 | AA 2 Conc mM | MPO U/ml | GO U/ml | Average Viability CFU/ml 50 min | Log Reduction 50 min |
|---|---|---|---|---|---|---|---|
| Glycine | 1.25 | L-Threonine | 1.25 | 4.7 | 4.2 | 515000 | 1.7 |
| Glycine | 1.25 | L-Tyrosine | 1.25 | 4.7 | 4.2 | 565 | 4.6 |
| Glycine | 1.25 | D-Phenylalanine | 1.25 | 4.7 | 4.2 | 4250000 | 0.8 |
| Glycine | 2.5 | none | 0 | 4.7 | 4.2 | 10050 | 3.4 |
| none | 0 | L-Alanine | 2.5 | 4.7 | 4.2 | 2230000 | 1.0 |
| none | 0 | D-Alanine | 2.5 | 4.7 | 4.2 | 1900000 | 1.1 |
| none | 0 | L-Aspartic acid | 2.5 | 4.7 | 4.2 | 4700000 | 0.7 |
| none | 0 | L-Glutamic acid | 2.5 | 4.7 | 4.2 | 11800000 | 0.3 |
| none | 0 | L-Glutamine | 2.5 | 4.7 | 4.2 | 12550000 | 0.3 |
| none | 0 | L-Histidine | 2.5 | 4.7 | 4.2 | 4750000 | 0.7 |
| none | 0 | L-Hydroxyproline | 2.5 | 4.7 | 4.2 | 11450000 | 0.3 |
| none | 0 | D-Leucine | 2.5 | 4.7 | 4.2 | 119000 | 2.3 |
| none | 0 | L-Lysine | 2.5 | 4.7 | 4.2 | 11400000 | 0.3 |
| none | 0 | L-Ornithine | 2.5 | 4.7 | 4.2 | 12650000 | 0.3 |
| none | 0 | L-Proline | 2.5 | 4.7 | 4.2 | 1500000 | 1.2 |
| none | 0 | L-Serine | 2.5 | 4.7 | 4.2 | 835000 | 1.5 |
| none | 0 | L-Threonine | 2.5 | 4.7 | 4.2 | 1415000 | 1.2 |
| none | 0 | L-Tyrosine | 2.5 | 4.7 | 4.2 | 890000 | 1.4 |
| none | 0 | D-Phenylalanine | 2.5 | 4.7 | 4.2 | 8850000 | 0.4 |
| none | 0 | none | 0 | 0 | 0 | 25000000 | 0.0 |

Example 7

The Effect of Two Way Amino Acid Combinations Containing L-Isoleucine on the Antimicrobial Activity of the Myeloperoxidase System Against *Staphylococcus aureus* in the Presence of Blood The amino acid L-isoleucine was identified in Example 2 as a strong enhancer of the activity of the MPO system against *Staphylococcus aureus*. The effect of two-way combinations of individual amino acids with L-isoleucine, as potential enhancing agents, for MPO microbicidal action in the presence of blood, was therefore examined by following the procedure of Example 5. The results are shown in the following Table 14, below.

TABLE 14

Effect of Two-Way Combinations of Amino Acids with L-Isoleucine
on the Microbicidal Activity of the Myeloperoxidase System
Against *Staphylococcus aureus* in the Presence of Blood

| Amino Acid 1 name | AA 1 Conc mM | Amino Acid 2 name | AA 2 Conc mM | MPO U/ml | GO U/ml | Average Viability CFU/ml 50 min | Log Reduction 50 min |
|---|---|---|---|---|---|---|---|
| L-Isoleucine | 1.25 | Beta-alanine | 1.25 | 4.7 | 4.2 | 13850000 | 0.3 |
| L-Isoleucine | 1.25 | D-Ala methyl ester | 1.25 | 4.7 | 4.2 | 14700000 | 0.3 |
| L-Isoleucine | 1.25 | L-Phenylalanine | 1.25 | 4.7 | 4.2 | 7900000 | 0.5 |
| L-Isoleucine | 1.25 | L-Glutamic acid | 1.25 | 4.7 | 4.2 | 13950000 | 0.3 |
| L-Isoleucine | 1.25 | D-Glutamine | 1.25 | 4.7 | 4.2 | 13700000 | 0.3 |
| L-Isoleucine | 1.25 | L-Alanine | 1.25 | 4.7 | 4.2 | 16400000 | 0.2 |
| L-Isoleucine | 1.25 | L-Hydroxyproline | 1.25 | 4.7 | 4.2 | 12850000 | 0.3 |
| L-Isoleucine | 1.25 | D-Leucine | 1.25 | 4.7 | 4.2 | 12600000 | 0.3 |
| L-Isoleucine | 1.25 | L-Lysine | 1.25 | 4.7 | 4.2 | 13350000 | 0.3 |
| L-Isoleucine | 1.25 | D-Ornithine | 1.25 | 4.7 | 4.2 | 11850000 | 0.4 |
| L-Isoleucine | 1.25 | L-Ornithine | 1.25 | 4.7 | 4.2 | 14700000 | 0.3 |
| L-Isoleucine | 1.25 | D-Phenylalanine | 1.25 | 4.7 | 4.2 | 4850000 | 0.7 |
| L-Isoleucine | 1.25 | L-Proline | 1.25 | 4.7 | 4.2 | 15950000 | 0.3 |
| L-Isoleucine | 1.25 | L-Serine | 1.25 | 4.7 | 4.2 | 13250000 | 0.3 |
| L-Isoleucine | 1.25 | D-Arginine | 1.25 | 4.7 | 4.2 | 12400000 | 0.3 |
| L-Isoleucine | 1.25 | L-Tyrosine | 1.25 | 4.7 | 4.2 | 8450000 | 0.5 |
| L-Isoleucine | 2.5 | none | 0 | 4.7 | 4.2 | 117000 | 2.4 |
| none | 0 | Beta-Alanine | 2.5 | 4.7 | 4.2 | 6000000 | 0.7 |

TABLE 14-continued

Effect of Two-Way Combinations of Amino Acids with L-Isoleucine on the Microbicidal Activity of the Myeloperoxidase System Against *Staphylococcus aureus* in the Presence of Blood

| Amino Acid 1 name | AA 1 Conc mM | Amino Acid 2 name | AA 2 Conc mM | MPO U/ml | GO U/ml | Average Viability CFU/ml 50 min | Log Reduction 50 min |
|---|---|---|---|---|---|---|---|
| none | 0 | D-Ala methyl ester | 2.5 | 4.7 | 4.2 | 8850000 | 0.5 |
| none | 0 | L-Phenylalanine | 2.5 | 4.7 | 4.2 | 12050000 | 0.3 |
| none | 0 | L-Glutamic acid | 2.5 | 4.7 | 4.2 | 13700000 | 0.3 |
| none | 0 | D-Glutamine | 2.5 | 4.7 | 4.2 | 15050000 | 0.3 |
| none | 0 | L-Alanine | 2.5 | 4.7 | 4.2 | 2215000 | 1.1 |
| none | 0 | L-Hydroxyproline | 2.5 | 4.7 | 4.2 | 11550000 | 0.4 |
| none | 0 | D-Leucine | 2.5 | 4.7 | 4.2 | 163500 | 2.2 |
| none | 0 | L-Lysine | 2.5 | 4.7 | 4.2 | 16950000 | 0.2 |
| none | 0 | L-Ornithine | 2.5 | 4.7 | 4.2 | 19200000 | 0.1 |
| none | 0 | L-Proline | 2.5 | 4.7 | 4.2 | 1835000 | 1.2 |
| none | 0 | L-Serine | 2.5 | 4.7 | 4.2 | 940000 | 1.5 |
| none | 0 | D-Arginine | 2.5 | 4.7 | 4.2 | 15000000 | 0.3 |
| none | 0 | L-Tyrosine | 2.5 | 4.7 | 4.2 | 1450000 | 1.3 |
| none | 0 | D-Phenylalanine | 2.5 | 4.7 | 4.2 | 7950000 | 0.5 |
| none | 0 | D-Ornithine | 2.5 | 4.7 | 4.2 | 17950000 | 0.2 |
| none | 0 | none | 0 | 0 | 0 | 27400000 | 0.0 |

An analysis of data, contained in Table 10 through Table 14, comparing the effect on the performance of all the formulations of two combined amino acids to the effect of each single amino acid was conducted to identify possible synergy or antagonism.

Thirty-seven amino acids or derivatives thereof were examined singly. Seventy-four pairs of amino acids were tested under the standard conditions described above.

Synergy Determination Method

Calculations for synergism or antagonism were made as follows:

For each tested pair of amino acids, the predicted CFU was calculated as the average of the CFU survivors found for the two outcomes of individual amino acids acting alone under the standard conditions. Consider for example the first synergistic combination with D-isoleucine and glycine shown in Table 11. The CFU for each amino acids acting separately, taken from Table 11, above, is 196000 and 9300, respectively. The average of these two numbers is 102650, shown as the predicted CFU survivors in line one of Table 16 below. The Actual CFU observed for the pair is then divided by the Predicted CFU and multiplied by 100 to calculate the % of Predicted value. This value is then to be compared to the threshold value, discussed in the next section, to determine whether the pair are synergistic, antagonistic, or additive.

Threshold Value Calculation

Calculation of appropriate threshold values for determination of synergism and antagonism was based upon the variability of replicated CFU survivor measures. Most measurements were made in duplicate. The pooled sum of squares for all duplicate data, after the log 10(CFU+1) transform, divided by the number of degrees of freedom gives the error variance of the log-transformed data. From this the Coefficient of Variation (CV) is calculated and shown in Table 15.

TABLE 15

Calculation of a Pooled Estimate of CFU Coefficient of Variation

| df | pooled SS | variance | std dev | ~CV |
|---|---|---|---|---|
| 709 | 5.6859 | 0.0080 | 0.0896 | 23% |

This CV is calculated over the entire range of CFU responses. For the response, therefore, normal variation is within two standard deviations or approximately 50% to 200%. A conservative factor of an additional two-fold was used here to ensure that actual synergism and antagonism is identified. Therefore the cutoff was set at 25% for synergism and 400% for antagonism. Applying this threshold to the above example gives the obvious conclusion that, there is a synergistic action of D-isoleucine and glycine, since the actual CFU for this pair was 0 CFU, or 0% of the predicted value.

Results Tables

The outcomes of each combination tested are divided into three tables: Table 16 shows the synergistic combinations with responses less than 25% of the predicted value, Table 17 shows the antagonists combinations with responses greater than 400% of the predicted value, and Table 18 shows the additive combinations, with responses between 25% and 400% of the predicted value.

TABLE 16

Synergistic Combinations

| Amino Acid 1 | Amino Acid 2 | Actual CFU | Predicted Average of Amino Acids | Predicted vs. Actual |
|---|---|---|---|---|
| D-Isoleucine | Glycine | 0 | 102650 | 0.0% |
| L-Tyrosine | Glycine | 565 | 589650 | 0.1% |
| Beta-Alanine | Glycine | 6800 | 1630900 | 0.4% |
| D-Valine | Glycine | 3330 | 319650 | 1.0% |
| L-Isoleucine | Glycine | 975 | 69317 | 1.4% |
| L-Valine | Glycine | 910 | 56900 | 1.6% |
| L-Aspartic acid | Glycine | 51000 | 3121317 | 1.6% |
| D-Ala methyl ester | Glycine | 125500 | 3834650 | 3.3% |
| L-Leucine | Glycine | 6900 | 106650 | 6.5% |
| L-Alanine | Glycine | 209500 | 2370483 | 8.8% |
| L-Glutamine | Glycine | 765000 | 6704650 | 11.4% |
| L-Lysine | Glycine | 680000 | 5704650 | 11.9% |
| L-Histidine | Glycine | 495000 | 2942150 | 16.8% |
| D-Alanine | Glycine | 162500 | 954650 | 17.0% |
| L-Glutamic acid | Glycine | 1100000 | 6124650 | 18.0% |
| L-Serine | Glycine | 99500 | 492650 | 20.2% |
| L-Proline | Glycine | 162500 | 739650 | 22.0% |

TABLE 17

Antagonistic Combinations

| Amino Acid 1 | Amino Acid 2 | Actual CFU | Predicted Average of Amino Acids | Predicted vs. Actual |
|---|---|---|---|---|
| L-Leucine | D-Tyrosine | 5050000 | 762000 | 662.7% |
| L-Isoleucine | L-Alanine | 16400000 | 2430500 | 674.8% |
| L-Isoleucine | D-Alanine | 13850000 | 1690917 | 819.1% |
| D-Threonine | D-Serine | 12300000 | 1482500 | 829.7% |
| L-Proline | D-Valine | 10100000 | 1050000 | 961.9% |
| L-Serine | D-Tyrosine | 11250000 | 1148000 | 980.0% |
| D-Proline | D-Isoleucine | 10500000 | 1043000 | 1006.7% |
| D-Proline | D-Leucine | 11600000 | 1052500 | 1102.1% |
| L-Tyrosine | L-Isoleucine | 8450000 | 649667 | 1300.7% |
| L-Proline | L-Isoleucine | 15950000 | 799667 | 1994.6% |
| L-Serine | L-Isoleucine | 13250000 | 552667 | 2397.5% |
| L-Leucine | D-Isoleucine | 7750000 | 200000 | 3875.0% |
| L-Isoleucine | D-Leucine | 12600000 | 172167 | 7318.5% |

TABLE 18

Additive Combinations

| Amino Acid 1 | Amino Acid 2 | Actual CFU | Predicted Average of Amino Acids | Predicted vs. Actual |
|---|---|---|---|---|
| L-Phenylalanine | L-Ornithine | 5950000 | 13800000 | 43.1% |
| L-Phenylalanine | D-Arginine | 6650000 | 12900000 | 51.6% |
| D-Histidine | D-Arginine | 6050000 | 11300000 | 53.5% |
| L-Ornithine | Glycine | 4600000 | 8204650 | 56.1% |
| L-Lysine | D-Phenylalanine | 8300000 | 13087500 | 63.4% |
| L-Threonine | Glycine | 515000 | 712150 | 72.3% |
| D-Glutamine | D-Arginine | 10850000 | 14700000 | 73.8% |
| L-Ornithine | D-Ornithine | 12850000 | 17175000 | 74.8% |
| Glycine | D-Leucine | 90000 | 112150 | 80.2% |
| L-Lysine | L-Glutamic acid | 12050000 | 14857500 | 81.1% |
| L-Hydroxyproline | Glycine | 4900000 | 5934650 | 82.6% |
| D-Phenylalanine | D-Isoleucine | 4100000 | 4448000 | 92.2% |
| L-Glutamic acid | D-Arginine | 12500000 | 13420000 | 93.1% |
| Glycine | D-Phenylalanine | 4250000 | 4354650 | 97.6% |
| L-Hydroxyproline | D-Glutamine | 13750000 | 13330000 | 103.2% |
| L-Isoleucine | D-Phenylalanine | 4850000 | 4414667 | 109.9% |
| L-Ornithine | L-Histidine | 12250000 | 11137500 | 110.0% |
| D-Isoleucine | D-Glutamine | 8950000 | 7498000 | 119.4% |
| L-Glutamine | L-Ala methyl ester | 12500000 | 10325000 | 121.1% |
| L-Lysine | D-Threonine | 11900000 | 9747500 | 122.1% |
| L-Lysine | D-Proline | 12350000 | 9682500 | 127.5% |
| L-Isoleucine | D-Ornithine | 11850000 | 9039667 | 131.1% |
| L-Leucine | L-Glutamic acid | 8200000 | 6222000 | 131.8% |
| D-Tyrosine | D-Glutamine | 11050000 | 8060000 | 137.1% |
| L-Phenylalanine | L-Isoleucine | 7900000 | 5664667 | 139.5% |
| L-Glutamic acid | L-Aspartic acid | 13150000 | 9236667 | 142.4% |
| L-Ala methyl ester | D-Phenylalanine | 11900000 | 7975000 | 149.2% |
| L-Lysine | L-Isoleucine | 13350000 | 8802167 | 151.7% |
| D-Serine | D-Glutamine | 12000000 | 7872500 | 152.4% |
| L-Histidine | D-Histidine | 11250000 | 6937500 | 162.2% |
| L-Isoleucine | D-Arginine | 12400000 | 7364667 | 168.4% |
| L-Valine | L-Glutamine | 11800000 | 6752250 | 174.8% |
| L-Ornithine | L-Isoleucine | 14700000 | 8264667 | 177.9% |
| D-Leucine | D-Ala methyl ester | 7100000 | 3937500 | 180.3% |
| L-Isoleucine | D-Glutamine | 13700000 | 7464667 | 183.5% |
| L-Aspartic acid | L-Alanine | 11350000 | 5482500 | 207.0% |
| L-Glutamine | D-Valine | 14850000 | 7015000 | 211.7% |
| L-Isoleucine | L-Hydroxyproline | 12850000 | 5994667 | 214.4% |
| L-Isoleucine | L-Glutamic acid | 13950000 | 6184667 | 225.6% |
| r-Isoleucine | Glycine | 94500 | 36650 | 257.8% |
| L-Histidine | D-Leucine | 10200000 | 3045000 | 335.0% |
| L-Isoleucine | D-Ala methyl ester | 14700000 | 3894667 | 377.4% |
| L-Histidine | D-Valine | 12600000 | 3252500 | 387.4% |

Racemic Combinations of Amino Acids

Racemic amino acids can be considered as a 1:1 mixture of the D- and L-isomers. Hence, some racemic mixtures were tested as combinations to identify antagonistic, additive, or synergistic mixtures based upon the performance of the individual D-, and L-enantiomers. The results for D-, L-, and racemic forms of four amino acids are shown in Table 19.

TABLE 19

Racemic Mixtures

| Amino Acid 1 name | AA 1 Conc mM | MPO U/ml | GO U/ml | Average Viability CFU/ml 50 min | Log Reduction 50 min |
|---|---|---|---|---|---|
| D,L-Isoleucine | 2.5 | 4.7 | 4.2 | 64000 | 2.7 |
| D,L-Leucine | 2.5 | 4.7 | 4.2 | 650000 | 1.6 |
| D,L-Phenylalanine | 2.5 | 4.7 | 4.2 | 900000 | 1.4 |
| D,L-Valine | 2.5 | 4.7 | 4.2 | 685000 | 1.5 |

TABLE 19-continued

Racemic Mixtures

| Amino Acid 1 name | AA 1 Conc mM | MPO U/ml | GO U/ml | Average Viability CFU/ml 50 min | Log Reduction 50 min |
|---|---|---|---|---|---|
| L-Isoleucine | 3.5 | 4.7 | 4.2 | 129333 | 2.3 |
| L-Leucine | 3.5 | 4.7 | 4.2 | 204000 | 2.1 |
| L-Phenylalanine | 3.5 | 4.7 | 4.2 | 11200000 | 0.4 |
| L-Valine | 2.5 | 4.7 | 4.2 | 104500 | 2.4 |
| D-Isoleucine | 2.5 | 4.7 | 4.2 | 196000 | 2.1 |
| D-Leucine | 2.5 | 4.7 | 4.2 | 215000 | 2.1 |

TABLE 19-continued

Racemic Mixtures

| Amino Acid 1 name | AA 1 Conc mM | MPO U/ml | GO U/ml | Average Viability CFU/ml 50 min | Log Reduction 50 min |
|---|---|---|---|---|---|
| D-Phenylalanine | 2.5 | 4.7 | 4.2 | 8700000 | 0.5 |
| D-Valine | 2.5 | 4.7 | 4.2 | 630000 | 1.6 |

Based upon the predicted values in the table below, racemic mixtures appear to be additive except for r-phenylalanine which appears to be synergistic.

TABLE 20

Racemic Mixtures Results

| Amino Acid | Actual CFU | Predicted Average of Amino Acids | Predicted vs Actual |
|---|---|---|---|
| d,l-Isoleucine | 64000 | 162667 | 39% |
| d,l-Leucine | 650000 | 209500 | 310% |
| d,l-Phenylalanine | 900000 | 9950000 | 9% |
| d,l-Valine | 685000 | 367250 | 187% |

Example 8

The Effect of Beta Alanine and L-Alanine Combination on the Antimicrobial Activity of the Myeloperoxidase System Against *Bacillus subtilis* Spores in the Presence of Blood The effect of a two-way combination of beta alanine and L-alanine, as potential enhancing agents, for MPO microbicidal action against *Bacillus subtilis* spores in the presence of blood, was determined following the procedure of Example 2. However, in this case each test contained a single low concentration of MPO (25 µg/mL or 9.4 U/mL) and glucose oxidase (8.3 U/mL). Suspensions of *Bacillus subtilis* containing 100% spores, as confirmed by microscopy, were obtained by washing with 50% ethanol to eliminate the vegetative forms of *Bacillus subtilis*. The effect of both L-alanine and beta alanine alone on the myeloperoxidase antimicrobial activity against *Bacillus subtilis* spores was tested for comparison. The results are shown in the following Table 21, below.

TABLE 21

The Effect of Beta Alanine and L-Alanine Combination on the Antimicrobial Activity of the Myeloperoxidase System Against *Bacillus subtilis* Spores in the presence of Blood

| Amino Acid 1 name | AA 1 Conc mM | Amino Acid 2 name | AA 2 Conc | MPO U/ml | GO U/ml | Average Viability CFU/ml 1 hr | Average Viability CFU/ml 2 hr | Log Reduction 1 hr | Log Reduction 2 hr |
|---|---|---|---|---|---|---|---|---|---|
| Beta alanine | 5 | L-Alanine | 0.2 | 9.4 | 8.3 | 80000 | | 2.3 | |
| Beta alanine | 5 | L-Alanine | 0.2 | 9.4 | 8.3 | | 70000 | | 2.4 |
| Beta alanine | 5 | L-Alanine | 0 | 9.4 | 8.3 | | 3100000 | | 0.7 |
| none | 0 | L-Alanine | 0.2 | 9.4 | 8.3 | 1200000 | | 1.1 | |
| none | 0 | L-Alanine | 0.2 | 9.4 | 8.3 | | 520000 | | 1.5 |
| none | 0 | none | 0 | 9.4 | 8.3 | | 3700000 | | 0.6 |

As can be seen in Table 21, the two way interaction of the amino acids beta alanine and L-alanine significantly enhanced the myeloperoxidase killing of *Bacillus subtilis* spores compared to the performance of the MPO system with L-alanine alone or in the absence of amino acids. In 2 hours, the beta alanine/L-alanine containing formulation demonstrated 2.4 log reduction where as the L-alanine only formulation provided 1.5 log reduction.

The nature of the relationship between beta alanine and L-alanine was examined following the synergy determination method described above. In 2 hours beta alanine alone exhibits 3100000 CFU survivors and L-alanine acting alone shows 520000 CFU. The average of these numbers is 1810000 CFU, which is the predicted value for the combination of the two amino acids. The actual CFU observed for the beta alanine/L-alanine pair is 70000 CFU, which represents only 3.9% of the predicted value indicating a synergistic combination.

Example 9

The Effect of Two Way Combinations and Individual Amino Acids on the Antimicrobial Activity of the Myeloperoxidase System Against Gram Negative, Gram Positive, and Yeast Organisms in the Presence of Blood The effect of two way combinations of amino acids glycine and valine, and individually beta alanine, as potential enhancing agents for MPO microbicidal action against *Pseudomonas aeruginosa, Staphylococcus aureus* and *Candida albicans*, in the presence of blood, was determined following the procedure of Example 2. Each organism was tested against a single low concentration of MPO (25 µg/mL or 9.4 U/mL) and glucose oxidase (8.3 U/mL). The two amino acid activators were each added at a final concentration of 2.5 μmol/mL and the individual amino acid, beta alanine, was tested at a single concentration of 5 μmol/mL. The effect of no amino acid containing formulations on the myeloperoxidase antimicrobial activity against these organisms was tested for comparison. The results are shown in Table 22, below.

TABLE 22

The Effect of Two Way Combinations and Individual Amino Acids on the Antimicrobial Activity of the Myeloperoxidase System Against Gram Negative, Gram Positive, and Yeast Organisms in the presence of Blood

| Organism name | Amino Acid 1 name | AA 1 Conc mM | Amino Acid 2 name | AA 2 Conc | Amino Acid 3 name | AA 3 Conc mM | MPO U/ml | GO U/ml | Starting Inoculum log 10 | Average Viability CFU/ml 30 min | Average Viability CFU/ml 60 min | Log Reduction 30 min | Log Reduction 60 min |
|---|---|---|---|---|---|---|---|---|---|---|---|---|---|
| P. aeruginosa | Glycine | 2.5 | L-Valine | 2.5 | Beta alanine | 0 | 9.4 | 8.3 | 7.5 | 885000 | | 1.5 | |
| P. aeruginosa | Glycine | 2.5 | L-Valine | 2.5 | Beta alanine | 0 | 9.4 | 8.3 | 7.5 | | 2070 | | 4.1 |
| P. aeruginosa | Glycine | 0 | L-Valine | 0 | Beta alanine | 5 | 9.4 | 8.3 | 7.5 | 52 | | 5.7 | |
| P. aeruginosa | Glycine | 0 | L-Valine | 0 | Beta alanine | 5 | 9.4 | 8.3 | 7.5 | | 6 | | 6.6 |
| P. aeruginosa | Glycine | 0 | L-Valine | 0 | Beta alanine | 0 | 9.4 | 8.3 | 7.5 | 210000 | | 2.1 | |
| P. aeruginosa | Glycine | 0 | L-Valine | 0 | Beta alanine | 0 | 9.4 | 8.3 | 7.5 | | 301500 | | 2.0 |
| C. albicans | Glycine | 2.5 | L-Valine | 2.5 | Beta alanine | 0 | 9.4 | 8.3 | 6.2 | 68500 | | 1.3 | |
| C. albicans | Glycine | 2.5 | L-Valine | 2.5 | Beta alanine | 0 | 9.4 | 8.3 | 6.2 | | 5000 | | 2.5 |
| C. albicans | Glycine | 0 | L-Valine | 0 | Beta alanine | 5 | 9.4 | 8.3 | 6.2 | 8500 | | 2.2 | |
| C. albicans | Glycine | 0 | L-Valine | 0 | Beta alanine | 5 | 9.4 | 8.3 | 6.2 | | 965 | | 3.2 |
| C. albicans | Glycine | 0 | L-Valine | 0 | Beta alanine | 0 | 9.4 | 8.3 | 6.2 | 151000 | | 1.0 | |
| C. albicans | Glycine | 0 | L-Valine | 0 | Beta alanine | 0 | 9.4 | 8.3 | 6.2 | | 73500 | | 1.3 |
| S. aureus | Glycine | 0 | L-Valine | 0 | Beta alanine | 5 | 9.4 | 8.3 | 7.4 | 0 | | 7.4 | |
| S. aureus | Glycine | 0 | L-Valine | 0 | Beta alanine | 5 | 9.4 | 8.3 | 7.4 | | 0 | | 7.4 |
| S. aureus | Glycine | 0 | L-Valine | 0 | Beta alanine | 0 | 9.4 | 8.3 | 7.4 | 6150000 | | 0.6 | |
| S. aureus | Glycine | 0 | L-Valine | 0 | Beta alanine | 0 | 9.4 | 8.3 | 7.4 | | 5050000 | | 0.7 |
| S. aureus | Glycine | 0 | L-Valine | 0 | Beta alanine | 2.5 | 4.7 | 4.2 | 7.4 | 8100000 | | 0.5 | |
| S. aureus | Glycine | 0 | L-Valine | 0 | Beta alanine | 2.5 | 4.7 | 4.2 | 7.4 | | 0 | | 7.4 |
| S. aureus | Glycine | 1.25 | L-Valine | 1.25 | Beta alanine | 0 | 4.7 | 4.2 | 7.4 | | 0 | | 7.4 |
| P. aeruginosa | none | 0 | none | 0 | none | 0 | 0 | 0 | 7.5 | 28650000 | 28650000 | 0 | 0 |
| C. albicans | none | 0 | none | 0 | none | 0 | 0 | 0 | 6.2 | 1400000 | 1455000 | 0 | 0 |
| S. aureus | none | 0 | none | 0 | none | 0 | 0 | 0 | 7.4 | 23800000 | 23800000 | 0 | 0 |

As shown in Table 22, both the two way combination of L-valine and glycine and the individual amino acid beta alanine significantly enhanced the microbicidal activity of the MPO system in the presence of blood against all the organisms tested compared to the performance of the MPO system in the absence of amino acids. In the case of P. aeruginosa, the enhancing effect of the L-valine/glycine combination was 2.1 logs within 60 minutes and the addition of 5 mM beta alanine alone to the MPO system increased the antibacterial activity by 4.6 logs in 60 minutes. Against C. albicans, the improvement in microbicidal activity provided by L-valine/glycine was 1.2 logs and 1.9 logs for beta alanine. The most dramatic improvement can be seen against S. aureus from the effect of beta alanine on the MPO system, with an increased performance of 6.8 logs within 30 minutes. Additionally, as can be seen in Table 21, the single amino acid beta alanine and the two amino acid combination of L-valine and glycine at both lower concentrations of amino acid and MPO, yielded complete kill of S. aureus within 60 minutes.

Example 10

In Vivo Testing Data for MPO Formulations Containing Various Combinations of Amino Acids and Additives An in vivo model was used to test the effectiveness of various combinations of amino acids in enhancing the effectiveness of the MPO antimicrobial system, as follows:

Adult male Sprague-Dawley rats were used in all studies. The rats were anesthetized and the hair on the back of each animal was removed with electric clippers and the skin was prepared. Two wound sites were prepared on the back of each rat. The hair on the back of each animal was removed with electric clippers and the animals anesthetized before the skin was prepared. Full thickness skin wounds were created by lifting loose skin and excising an elliptical area with scissors using sterile technique, exposing the fascia.

An open polystyrene cylinder (2.5 cm in diameter) was glued to each treatment site with QuickTite® (Loctite Corp.) cement. Each cylinder formed a liquid-tight test chamber, the base of which was the wound. The exposed fascia was then inoculated with 200 μl containing about $10^7$ CFU of S. aureus. Fifteen minutes later the inoculated fascia was treated. Where increased biological challenge was desired, 30 μl of whole fresh rat blood was added at this time. Next, 800 μl of a test formulation was added to the site resulting in a total volume of 1.0 mL per test site. The test formulations contained myeloperoxidase, various amino acids, glucose oxidase and glucose in the amounts set forth in the following tables. Control sites had no p-MPO administered and were treated with 800 μl of 0.9% sterile saline or buffer. Both sites on a single rat received the same treatment.

Following a predetermined treatment time with p-MPO formulation, a large excess of catalase was added to each treatment site to stop further microbicidal activity. This destroyed any remaining and/or subsequently generated hydrogen peroxide by the formulation.

The fluids remaining in the cylinder were recovered separately and the underlying fascia was aseptically excised, weighed, and homogenized. Surviving bacterial counts of liquid samples and excised tissues were assessed by quantitative culture. Results are reported as log reduction from the initial inoculum.

Using the foregoing procedures, the in vivo effectiveness in inhibiting S. aureus (inoculum containing $2 \times 10^7$ CFU of S. aureus) of a 5 minute exposure to an enhanced myeloperoxidase test formulation of the invention comprising the amino acids L-alanine, L-proline, and glycine was determined in the presence of 3% blood and without blood as an average of 8 replicates. The results are shown in the following Table 23.

TABLE 23

| blood % | Ala mM | Pro mM | Gly mM | Glu mM | MPO µg/ml | GO U/ml | MPO/GO ratio | Average Viability CFU/ml | Log 10 (CFU + 1) survivors | Log Reduction |
|---|---|---|---|---|---|---|---|---|---|---|
| 0 | 1.4 | 1.5 | 1.5 | 150 | 200 | 13.3 | 15 | 11620 | 3.9 | 3.4 |
| 3 | 1.4 | 1.5 | 1.5 | 150 | 200 | 13.3 | 15 | 10290 | 4.0 | 3.3 |

As shown in Table 23, the amino acid enhanced myeloperoxidase test formulation performs in a similar fashion with and without the presence of added blood at 5 minutes exposure.

Using the foregoing procedure, the in vivo effect of glucose concentration on test formulations containing varied concentrations of L-alanine, L-proline, and glycine was determined with an inoculum containing $2 \times 10^7$ CFU of *S. aureus*, as shown in the following Table 24 as an average of 6 replicates.

TABLE 24

| blood % | Ala mM | Pro mM | Gly mM | Glu mM | MPO µg/ml | GO U/ml | MPO/GO ratio | Average Viability CFU/ml | Log 10 (CFU + 1) survivors | Log Reduction |
|---|---|---|---|---|---|---|---|---|---|---|
| 0% | 4 | 5 | 5 | 150 | 200 | 13.3 | 15 | 1261 | 2.9 | 3.4 |
| 0% | 4 | 5 | 5 | 60 | 200 | 13.3 | 15 | 3952 | 3.2 | 3.0 |
| 0% | 0.4 | 0.5 | 0.5 | 150 | 200 | 13.3 | 15 | 4872 | 3.6 | 2.7 |
| 0% | 0.4 | 0.5 | 0.5 | 60 | 200 | 13.3 | 15 | 1313 | 3.0 | 3.2 |

As shown, the differences observed between averages of performance are not statistically different for the conditions tested.

Following the foregoing procedures, the in vivo effect of varying L-alanine, L-proline, and glycine concentrations on the microbicidal activity of test formulations containing myeloperoxidase at 200 or 400 µg/ml in the presence of 6% blood or without blood was determined. The results are shown in Table 25.

TABLE 25

| Organism | blood | Pro mM | Gly mM | Glu mM | MPO ug/ml | GO U/ml | MPO to GO ratio | Log Starting Inoculum | Org Exp Time min | N | Average Viability CFU/ml 5 min | Log 10 (CFU + 1) survivors 5 min | Log Reduction 5 min |
|---|---|---|---|---|---|---|---|---|---|---|---|---|---|
| S. aureus | 0% | 5 | 5 | 150 | 200 | 13.3 | 15 | 6.3 | 15 | 4 | 3373 | 2.7 | 3.7 |
| S. aureus | 0% | 10 | 10 | 150 | 200 | 13.3 | 15 | 6.3 | 15 | 8 | 3053 | 3.1 | 3.4 |
| S. aureus | 0% | 5 | 5 | 150 | 400 | 26.7 | 15 | 6.3 | 15 | 4 | 3390 | 3.4 | 2.9 |
| S. aureus | 0% | 20 | 20 | 150 | 400 | 26.7 | 15 | 6.3 | 15 | 8 | 416 | 2.4 | 3.9 |
| S. aureus | 6% | 5 | 5 | 150 | 200 | 13.3 | 15 | 6.3 | 15 | 8 | 41309 | 4.0 | 2.7 |
| S. aureus | 6% | 10 | 10 | 150 | 200 | 13.3 | 15 | 6.3 | 15 | 8 | 131082 | 4.5 | 1.9 |
| S. aureus | 6% | 5 | 5 | 150 | 400 | 26.7 | 15 | 6.3 | 15 | 8 | 89595 | 5.0 | 1.3 |
| S. aureus | 6% | 20 | 20 | 150 | 400 | 26.7 | 15 | 6.3 | 15 | 8 | 49079 | 4.6 | 1.9 |

Following the foregoing procedures, the in vivo effect of scaling versus not scaling L-alanine, L-proline, and glycine concentrations on the microbicidal activity of test formulations containing myeloperoxidase at 200 or 400 µg/ml was determined. In this context, scaling refers to proportional change of the amino acid concentration in concert with MPO concentration. The results are shown in Table 26.

TABLE 26

| Organisms | blood | Ala mM | Pro mM | Gly mM | Glu mM | MPO ug/ml | MPO to GO ratio | Log Starting inoculum | Org Exp Time min | N | Average Viability CFU/ml 5 min | Log 10 (CFU + 1) Survivors 5 min | Log Reduction 5 min |
|---|---|---|---|---|---|---|---|---|---|---|---|---|---|
| S. aureus | 0 | 8.0 | 10.0 | 10.0 | 150 | 200 | 15 | 6.3 | 15 | 6 | 120167 | 5.1 | 1.2 |
| S. aureus | 0 | 4.0 | 5.0 | 5.0 | 150 | 200 | 15 | 6.3 | 15 | 6 | 11700 | 4.1 | 2.3 |
| S. aureus | 0 | 16.0 | 20.0 | 20.0 | 150 | 400 | 15 | 6.3 | 15 | 6 | 49162 | 4.7 | 1.7 |
| S. aureus | 0 | 4.0 | 5.0 | 5.0 | 150 | 400 | 15 | 6.3 | 15 | 6 | 4810 | 3.7 | 2.6 |

As shown in Table 26, the formulation containing the lowest total concentration of amino acids (4 mM L-alanine, 4 mM L-proline and 5 mM glycine) performs best at myeloperoxidase concentrations of both 200 and 400 µg/ml.

Following the foregoing procedures, the in vivo effect of test formulations containing L-proline, L-lysine and glycine, or L-proline and glycine, were determined and found to be highly effective in the inhibition of *S. aureus*, as shown in Table 27.

TABLE 27

| Organisms | blood | Lys mM | Pro mM | Gly mM | Glu mM | MPO ug/ml | MPO to GO ratio | Log Starting inoculum | Org Exp Time min | N | Average Viability CFU/ml 30 min | Log 10 (CFU + 1) Survivors 30 min | Log Reduction 30 min |
|---|---|---|---|---|---|---|---|---|---|---|---|---|---|
| S. aureus | 0 | 8.2 | 11.4 | 24.0 | 150 | 200 | 15 | 6.2 | 15 | 6 | 8 | 0.6 | 5.6 |
| S. aureus | 0 | 0.0 | 9.6 | 10.0 | 150 | 200 | 15 | 6.2 | 15 | 6 | 0 | 0 | 6.2 |

As shown in Table 27, test formulations containing either L-proline, L-lysine and glycine or L-proline and glycine enhance the performance of the myeloperoxidase antimicrobial system. These two formulations at 200 µg/ml MPO and a 15:1 MPO:GO ratio gave complete kill within 30 minutes. They outperform formulations having twice the MPO and 20 times the GO in the presence of the then best performing additive, 2% Triton X-200. See Table 28 below.

Following the foregoing procedures, the in vivo effect of a test formulation containing the single amino acid L-alanine and 2% Triton X-200 at a 1.5:1 MPO:GO ratio was determined. The results are shown in Table 28.

TABLE 28

| Organisms | blood | Additive Triton | Glu mM | Ala mM | MPO ug/ml | MPO to GO ratio | Log Starting inoculum | Org exp Time min | N | Average Viability CFU/ml 30 min | Log 10 (CFU + 1) Survivors 30 min | Log Reduction 30 min |
|---|---|---|---|---|---|---|---|---|---|---|---|---|
| S. aureus | 0 | 2% | 90 | 0.2 | 400 | 1.5 | 5.9 | 15 | 6 | 313 | 2.2 | 3.7 |
| S. aureus | 3% | 2% | 90 | 0.2 | 400 | 1.5 | 5.9 | 15 | 6 | 356 | 2.5 | 3.4 |

The formulation containing 2% of Triton X-200 performs comparably with and without 3% added blood, but with the single amino acid L-alanine, the test formulation was significantly less effective in the inhibition of *S. aureus* than the formulations containing two or more amino acids, as shown above. This result is confirmed in Tables 28 and 29, below.

Following the foregoing procedures, the in vivo effect of a test formulation containing the single amino acid L-alanine, 1% Triton X-200, a 3:1 MPO:GO ratio and a glucose concentration of 90 mM was determined. The results, shown as the average of 6 replicates, are shown in Table 29.

TABLE 29

| Additive Triton | Ala mM | MPO µg/ml | Log Starting Inoculum log 10 | Average Viability CFU/ml 30 min | Log 10 (CFU + 1) Survivors 30 min | Log Reduction 30 min |
|---|---|---|---|---|---|---|
| 1% | 0.2 | 400 | 5.9 | 513 | 2.15 | 3.65 |

Following the foregoing procedures, the in vivo effect of a test formulation containing the single amino acid L-alanine at a 3:1 MPO:GO ratio was determined for three concentrations of MPO. The results, shown as the average of 4 replicates, are shown in Table 30.

TABLE 30

| Alanine Conc mM | Glu mM | MPO μg/ml | GO U/ml | MPO to GO ratio | Log Starting Inoculum log 10 | Average Viability CFU/ml 30 min | Log 10 (CFU + 1) Survivors 30 min | Log Reduction 30 min |
|---|---|---|---|---|---|---|---|---|
| 0.2 | 90 | 400 | 133 | 3 | 5.8 | 90 | 2.0 | 3.8 |
| 0.2 | 90 | 200 | 67 | 3 | 5.8 | 1112 | 3.0 | 2.8 |
| 0.2 | 90 | 100 | 33 | 3 | 5.8 | 13440 | 4.1 | 1.7 |
| 0 | 0 | 0 | 0 | 0 | 5.8 | 670000 | 5.8 | 0 |

This formulation yielded a maximum of 3.8 log reduction in 30 minutes at 400 μg/ml. Without any additives, the performance of this test formulation containing the single amino acid L-alanine is clearly limited in the presence of biological interferences.

The in vivo time course effect of a test formulation containing L-proline, glycine, and L-alanine at a 15:1 MPO:GO ratio was determined for three concentrations of MPO. The results of time-kill studies are presented in FIG. 4. The data are presented as $\log_{10}$ reduction in CFU/ml at designated time points. The Enhanced MPO Solution demonstrated bactericidal activity against S. aureus at all concentrations tested. In this test the inoculum was increased to $10^7$ CFU. The results, shown as an average of 6 replicates, are shown in Table 31.

TABLE 31

| Pro mM | Gly mM | Ala mM | MPO ug/ml | GO U/ml | MPO/ GO ratio | Average Viability CFU/ml | | | Log 10 (CFU + 1) Survivors | | | Log Reduction | | |
|---|---|---|---|---|---|---|---|---|---|---|---|---|---|---|
| | | | | | | 5 min | 15 min | 30 min | 5 min | 15 min | 30 min | 5 min | 15 min | 30 min |
| 3.6 | 3.6 | 2.8 | 400 | 27 | 15 | 548 | 68 | 12 | 2.7 | 1.8 | 1.1 | 4.6 | 5.5 | 6.2 |
| 1.8 | 1.8 | 1.4 | 200 | 13 | 15 | 647 | 179 | 91 | 2.8 | 2.3 | 2.0 | 4.6 | 5.1 | 5.4 |
| 0.5 | 0.5 | 0.4 | 50 | 3 | 15 | 18286 | 3713 | 1284 | 4.3 | 3.6 | 3.1 | 3.1 | 3.7 | 4.2 |
| | | | 0 | 0 | 0 | | | 22100000 | | | 7.3 | | | |
| | | | 0 | 0 | 0 | | | 23350000 | | | 7.4 | | | |
| | | | 0 | 0 | 0 | | | 20000000 | | | 7.3 | | | |

As shown in Table 31, the amino acid enhanced formulation resulted in 3.1 log reduction within 5 minutes using 8 times less MPO (50 μg/ml) than the single amino acid formulation containing L-alanine at 400 ug/ml from Table 30. The amino acid enhanced formulation yields faster and greater microbicidal activity in vivo.

Example 11

In Vitro Testing Data for MPO Formulations Containing Various Combinations of Amino Acids and Additives Bacterial Strains.

The organisms (530 strains) selected to determine the spectrum of activity of an illustrative embodiment of a composition of the invention having enhanced activity ("the Enhanced MPO Solution") for MIC and MBC testing included 140 staphylococci (of which 70 oxacillin-resistant, 5 vancomycin-intermediate/resistant, 4 Panton Valentine Leukocidin [PVL] positive), 95 β-hemolytic streptococci strains, 55 enterococci (33 vancomycin-susceptible, 22 vancomycin-resistant), 148 Enterobacteriaceae strains (of which 51 ceftazidime-resistant), and 92 non-Enterobacteriaceae species (of which 54 ceftazidime-resistant). All clinical isolates were obtained from the culture collection of Eurofins Medinet Anti-Infective Services (Herndon, Va.), and represent diverse geographical regions. They were originally derived from clinical specimens and identified using standard microbiological methods (see Table 33 below for details). *Escherichia coli* ATCC 25922, *Staphylococcus aureus* ATCC 25923, *S. aureus* ATCC 29213, *Pseudomonas aeruginosa* ATCC 27853, and *Enterococcus faecalis* ATCC 29212 were used as quality control strains for the Enhanced MPO Solution and comparator agents to validate the modified Clinical and Laboratory Standards Institute (CLSI, formally NCCLS) broth microdilution method.

Antimicrobial Agents.

The Enhanced MPO Solution is supplied as two separate aqueous solutions, packaged in different vials, named Concentrate and Diluent. The Concentrate contains p-MPO, glucose oxidase (GO), and amino acids in an aqueous formulation vehicle, consisting of sodium chloride, polysorbate-80 (Tween-80) in sodium phosphate buffer in Water-for-Injection. The Diluent contains dextrose (glucose) in the same aqueous formulation vehicle as the Concentrate. Concentrate and Diluent are mixed together to produce the drug product, the Enhanced MPO Solution.

The quantitative composition of the Enhanced MPO Solution is shown in Table 32 at three concentrations of MPO. As can be seen in this table, the glucose oxidase activity and the concentrations of amino acids are directly proportional to the MPO concentration. The dextrose concentration is maintained between 280 and 336 mM. The remaining ingredients are held at constant concentrations.

TABLE 32

Quantitative Composition of the Enhanced MPO Solution At Three Concentrations

| MPO (GU/mL) | GO (U/mL) | L-Alanine (mM) | L-Proline (mM) | Glycine (mM) | Dextrose (mM) | Sodium Chloride (mM) | Polysorbate 80 (% w/v) | Sodium Phosphate Buffer (mM) | pH |
|---|---|---|---|---|---|---|---|---|---|
| 150 | 26.67 | 2.8 | 3.6 | 3.6 | 300 | 150 | 0.02 | 20 | 6.5 |
| 75 | 13.33 | 1.4 | 1.8 | 1.8 | 280 | 150 | 0.02 | 20 | 6.5 |
| 37.5 | 6.67 | 0.7 | 0.9 | 0.9 | 308 | 150 | 0.02 | 20 | 6.5 |

Note:
MPO concentration is expressed as guaiacol units (GU) per mL

The Enhanced MPO Solution is comprised of two aqueous solutions designated as Concentrate solution and Diluent solution that are mixed prior to use. The Concentrate solution contains MPO, GO, sodium chloride, and specific antimicrobial activity enhancing agents in an aqueous formulation vehicle. The Diluent solution contains glucose (dextrose) in the same aqueous formulation vehicle as the Concentrate solution. The Concentrate and Diluent solutions are mixed together in varying proportions just prior to use to produce the drug product, the Enhanced MPO Solution, at a desired concentration. The Enhanced MPO Solution concentration is expressed as micrograms of MPO per milliliter (µg/ml) and is also expressed as Guaiacol Units of MPO activity per milliliter (GU/ml). The conversion of µg to GU of MPO is based on 0.375 GU/µg of MPO. Quality control agents included cefazolin and gentamicin obtained from Sigma Chemical (St. Louis, Mo.) and selected comparators used were gentamicin (Sigma Chemical) and mupirocin lithium from GlaxoSmithKline, Inc. (Philadelphia, Pa.). All stock solutions were prepared immediately prior to testing. The concentration ranges were 0.004 to 8 µg/ml for the Enhanced MPO Solution, 0.06 to 64 µg/ml for cefazolin, 0.25 to 16 µg/ml for gentamicin, and 0.12 to 16 µg/ml for mupirocin. Antimicrobials used for drug interaction studies were as follows: cefazolin, ceftriaxone, ceftazidime, ciprofloxacin, doxycycline, gentamicin, imipenem, and vancomycin from GlaxoSmithKline, Inc. (Philadelphia, Pa.).

Antimicrobial Susceptibility Testing.

Broth microdilution and methods for determining bactericidal activity were performed using the CLSI recommended procedures (Clinical and Laboratory Standards Institute. Methods for determining bactericidal activity of antimicrobial agents; approved guideline. CLSI document M26-A. CLSI, Wayne, Pa. September 1999, Clinical and Laboratory Standards Institute. Methods for dilution antimicrobial susceptibility tests for bacteria that grow aerobically; approved standard—7$^{th}$ ed. CLSI document M7-A7. CLSI, Wayne, Pa. January 2006). Modifications were made to the standard broth microdilution method to accommodate the rapid in vitro activity of the Enhanced MPO Solution as described below. Each antimicrobial agent and Concentrate solution was diluted in double strength cation-adjusted Mueller-Hinton Broth (CAMHB) and dispensed in mircrodilution trays. All β-hemolytic streptococci were tested in double strength CAMHB supplemented with 5% lysed horse blood. Isolates were prepared by suspending several colonies (four to six) from an overnight culture on Trypticase Soy Agar (TSA) with 5% sheep blood into sterile saline and the density adjusted to a 0.5 McFarland standard (~$10^8$ CFU/ml). Standardized bacterial suspensions were further diluted in double strength Diluent solution so that approximately $5\times10^5$ CFU/ml was mixed with serial drug dilutions. The addition of Diluent solution to the Concentrate solution activates the enzyme system, which in turn exerts its rapid mode of action. The microdilution trays were incubated in ambient air at 35° C. for 18 to 24 h. The MIC was determined by observing the lowest concentration of antimicrobial agent that completely inhibited the growth of the organism.

Minimum bactericidal concentrations (MBCs) were determined by first performing the modified broth microdilution method described above for the Enhanced MPO Solution MIC. From the microdilution tray, the last drug containing well with visible growth and each clear well thereafter were sampled. A 10 µl sample per well was plated onto TSA with 5% sheep blood and incubated in ambient air for 24 h and examined for growth and colony counts. The MBC was determined as the lowest antimicrobial concentration that demonstrated a ≥99.9% reduction in colony forming units relative to the starting inoculum size.

Quality Control Parameters.

MIC ranges were established for the Enhanced MPO Solution by testing over 20 replicates of one lot of the Enhanced MPO Solution against S. aureus ATCC 29213 and E. coli ATCC 25922. Quality control parameters were then determined for the Enhanced MPO Solution by testing three lots of the Concentrate solution used for preparation of the final Enhanced MPO Solution formulation. Testing was performed in duplicate against S. aureus ATCC 29213 and E. coli ATCC 25922. The effects of modifying the standard broth microdilution test were also assessed with antibiotics with known quality control limits to validate the CLSI broth microdilution method.

The results are show in the following Table 33, where the Enhanced MPO Solution formulation is designated "E-MPO".

TABLE 33

In vitro activity of the Enhanced MPO Solution and other comparator antimicrobials against a panel of clinical isolates consisting of 530 enterococci, staphylococci, streptococci, Enterobacteriaceae, and non-Enterobacteriaceae species

| | | MIC µg/ml | | |
|---|---|---|---|---|
| Organism(no. of isolates tested) | Compound | 50% | 90% | Range[a] |
| Enterococcus faecalis(33) | E-MPO | 0.5 | 0.5 | 0.12-0.5 |
| | Mupirocin | 32 | >32 | 8->32 |

TABLE 33-continued

In vitro activity of the Enhanced MPO Solution and other comparator antimicrobials against a panel of clinical isolates consisting of 530 enterococci, staphylococci, streptococci, Enterobacteriaceae, and non-Enterobacteriaceae species

| Organism(no. of isolates tested) | Compound | MIC µg/ml 50% | 90% | Range[a] |
|---|---|---|---|---|
| Enterococcus faecium(22) | E-MPO | 0.12 | 0.12 | 0.06-0.12 |
|  | Mupirocin | 0.25 | 0.25 | 0.06-0.5 |
| Staphylococcus aureus(109) | E-MPO | 0.015 | 0.03 | 0.008-0.06 |
|  | Mupirocin | 0.06 | 0.12 | ≤0.03->32 |
| Staphylococcus epidermidis(31) | E-MPO | 0.03 | 0.03 | 0.015-0.06 |
|  | Mupirocin | 0.12 | >32 | ≤0.03->32 |
| Streptococcus agalactiae(34) | E-MPO | 0.5 | 0.5 | 0.12-1 |
|  | Mupirocin | 0.5 | 0.5 | 0.12-2 |
| Streptococcus GroupC(8) | E-MPO | n/a[b] | n/a | 0.5-1 |
|  | Mupirocin | n/a | n/a | 0.06-0.5 |
| Streptococcus GroupF(2) | E-MPO | n/a | n/a | 1-1 |
|  | Mupirocin | n/a | n/a | 0.25-0.25 |
| Streptococcus GroupG(18) | E-MPO | 0.5 | 0.5 | 0.25-1 |
|  | Mupirocin | 0.12 | 0.12 | 0.06-0.5 |
| Streptococcus pyogenes(33) | E-MPO | 0.5 | 0.5 | 0.12-0.5 |
|  | Mupirocin | 0.12 | 0.25 | 0.06-0.5 |
| Citrobacter freundii(20) | E-MPO | 0.6 | 0.12 | 0.03-0.12 |
|  | Gentamicin | 2 | 4 | 2->32 |
| Enterobacter cloacae(21) | E-MPO | 0.12 | 0.12 | 0.06-0.12 |
|  | Gentamicin | 2 | 8 | 1->32 |
| Escherichia coli(52) | E-MPO | 0.25 | 0.25 | 0.12-0.5 |
|  | Gentamicin | 4 | >32 | 2->32 |
| Klebsiella pneumoniae(31) | E-MPO | 0.25 | 0.25 | 0.06-0.25 |
|  | Gentamicin | 4 | >32 | 2->32 |
| Proteus mirabilis(24) | E-MPO | 0.06 | 0.06 | 0.03-0.06 |
|  | Gentamicin | 8 | 8 | 2->32 |
| Acintobacter spp.(29) | E-MPO | 0.12 | 0.12 | 0.06-0.12 |
|  | Gentamicin | 8 | >32 | 0.5->32 |
| Pseudomonas aeruginosa(53) | E-MPO | 0.06 | 0.06 | 0.03-0.12 |
|  | Gentamicin | 4 | 16 | 1->32 |
| Aeromonas hydrophilia(5) | E-MPO | n/a | n/a | 0.015-0.03 |
|  | Gentamicin | n/a | n/a | 1-4 |
| Pasteurella multocida(5) | E-MPO | n/a | n/a | ≤0.004 |
|  | Gentamicin | n/a | n/a | 2-16 |

[a]Range of MIC values for all strains tested
[b]n/a, not applicable, total number of isolates less than 10

The modification of the CLSI broth microdilution method for testing the Enhanced MPO Solution provides an efficient procedure for product characterization and determination of the spectrum of activity. The results of testing the Enhanced MPO Solution and selected topical comparator drugs against 530 bacterial clinical isolates shown in Table 33 demonstrate that the Enhanced MPO Solution exhibits potent broad-spectrum activity against both Gram-positive and Gram-negative species tested. Among the enterococci, the MICs of the Enhanced MPO Solution at which 50% and 90% of isolates were inhibited ($MIC_{50}$ and $MIC_{90}$ values) were 0.5 µg/ml for E. faecalis and 0.12 µg/ml for E. faecium. No difference was noted in the activity of the Enhanced MPO Solution against vancomycin-susceptible or vancomycin-resistant enterococci (VRE). Based on the $MIC_{90}$s, the Enhanced MPO Solution was >64 fold more active against E. faecalis than was mupirocin. Among the Gram-positive cocci, the Enhanced MPO Solution was most active against the staphylococci. All MICs for S. aureus and S. epidermidis, including MRSA and MRSE, were ≤0.06 µg/ml, with a $MIC_{90}$ of 0.03 µg/ml. The potency of the Enhanced MPO Solution was comparable for both oxacillin-resistant and oxacillin-susceptible strains. The Enhanced MPO Solution was highly active against PVL positive and VISA/VRSA strains demonstrating equivalent activity compared to wild types. The MIC values for PVL positive isolates were within the range of all S. aureus strains tested. Among the streptococci, the Enhanced MPO Solution was highly active even in the presence of CAMHB supplemented with 5% lysed horse blood. The $MIC_{90}$ for S. agalactiae and S. pyogenes were both 0.5 µg/ml. For the streptococci groups C, F, and G, the MICs were ≤1 µg/ml with an MIC range of 0.25 to 1 µg/ml. With the exception of S. agalactiae and S. pyogenes, the Enhanced MPO Solution demonstrated greater potency in vitro than mupirocin by $MIC_{90}$. The MIC ranges for mupirocin against E. faecalis, S. aureus, and S. epidermidis extended to >32 µg/ml.

Overall, the Enhanced MPO Solution was highly active against the Enterobacteriaceae species (Table 33) with a $MIC_{90}$ of 0.25 µg/ml and a MIC range from 0.03 to 0.25 µg/ml. Among the Gram-negative non-fermentative organisms, the MICs were ≤0.12 µg/ml and displayed a narrow range of activity (≤0.004 to 0.12 µg/ml). The Enhanced MPO Solution displayed excellent activity against P. aeruginosa ($MIC_{90}$, 0.06 µg/ml) and Acinetobacter species ($MIC_{90}$ 0.12 µg/ml) which are often difficult organisms to treat. No difference was noted in the activity of the Enhanced MPO Solution against ceftazidime-susceptible and ceftazidime-resistant strains. Based on the $MIC_{90}$, the Enhanced MPO Solution was 32 to >256-fold more active than gentamicin for all gram negative organisms tested.

The results of MIC and MBC testing of clinical isolates of pathogens commonly associated with skin and skin structure infections are summarized in Table 34.

TABLE 34

Minimum inhibitory and bactericidal concentrations of the
Enhanced MPO Solution against clinical isolates associated
with skin and skin structure infections

| Isolate | MIC µg/ml[a] | | | MBC µg/ml | | |
|---|---|---|---|---|---|---|
| (no. tested) | $MIC_{50}$ | $MIC_{90}$ | Range[a] | $MBC_{50}$ | $MBC_{90}$ | Range |
| E. faecalis (7) | n/a[b] | n/a | 0.12-0.5 | n/a | n/a | 0.5-2 |
| S. aureus (16) | 0.015 | 0.03 | 0.015-0.03 | 0.015 | 0.03 | 0.015-0.03 |
| S. agalactiae (13) | 0.5 | 0.5 | 0.12-0.5 | 0.5 | 0.5 | 0.12-1 |
| S. pyogenes (20) | 0.5 | | 0.5 0.12-0.5 | 0.5 | 1 | 0.12-1 |
| E. coli (5) | n/a | n/a | 0.12-0.25 | n/a | n/a | 0.12-1 |
| P. aeruginosa (5) | n/a | n/a | 0.03-0.06 | n/a | n/a | 0.06-0.5 |

[a]Range of MIC values for all strains tested
[b]n/a, not applicable, total number of isolates less than 10

The potent bactericidal activity of the Enhanced MPO Solution was confirmed by the range of MBCs (0.015 to 2 µg/ml). The Enhanced MPO Solution was most active against all isolates of S. aureus with identical MIC and MBC values (MIC50 and MBC50=0.015 µg/ml; MIC90 and MBC90=0.03 µg/ml).

Agar-based methods were not applicable for comparison because of the potential interfering properties of the medium. However, the effect of changing standardized broth susceptibility test conditions on cefazolin, gentamicin, and mupirocin MICs were assessed and validated by comparing the results to that of the CLSI reference broth microdilution method. The in vitro test parameters of both modified and reference MIC methods were similar in respect to media (CAMHB), pH (7.2), final inoculum ($5 \times 10^5$ CFU/ml), and incubation environment (35° C., ambient air). Changing to an inoculum preparation in Diluent solution showed no significant effect on the expected MIC results for comparator antibiotics (Clinical Laboratory Standards Institute. Performance standards for antimicrobial susceptibility testing; seventeenth informational supplement. CLSI document M100-S17. Wayne, Pa. January 2007). Cefazolin and mupirocin MICs for S. aureus ATCC 29213 and cefazolin and gentamicin MICs for E. coli ATCC 25922 were within previously published quality control ranges (CLSI document M100-S17, supra). The quality control range determined for the Enhanced MPO Solution for S. aureus ATCC 29212 and E. coli ATCC 25922 was 0.010 to 0.03 µg/ml and 0.15 to 0.5 µg/ml, respectively. Over 20 replicates were performed with these organisms and the results were all within the established quality control range. The results of testing three lots of Concentrate solution in duplicate demonstrated all MIC values to be within the established quality control range.

As shown above, the comparative in vitro activity for the Enhanced MPO Solution was equivalent to or greater than that of mupirocin against Gram-positive organisms and was several fold greater than that of gentamicin for Gram-negative organisms. No differences were observed in susceptibility to the Enhanced MPO Solution among resistant and susceptible strains studied. Of importance, MBC studies showed that the Enhanced MPO Solution exhibits bactericidal activity against S. aureus and S. pyogenes, two of the most common pathogens associated with serious skin infections.

Time-Kill Studies.

The bactericidal effect of the Enhanced MPO Solution was assessed by two methods: a suspension-neutralization method (Tortorano, A. M., M. A. Viviani, E. Biraghi, A. L. Rigoni, A. Prigitano, R. Grillot, and the EBGA Network. 2005. In vitro testing of fungicidal activity of biocides against Aspergillus fumigatus. J. Med. Microbiol. 54:955-957) and by an adaptation of the CLSI microdilution time-kill assay (Clinical and Laboratory Standards Institute. Methods for determining bactericidal activity of antimicrobial agents; approved guideline. CLSI document M26-A. CLSI, Wayne, Pa. September 1999). The suspension-neutralization method was used to assess the rapid rate of bactericidal activity of the Enhanced MPO Solution and the effect on its biological activity by blood as an example of interfering material. The CLSI method was also used to assess the microbicidal activity of the Enhanced MPO Solution by an adaptation of standardized testing.

Figure 1B:
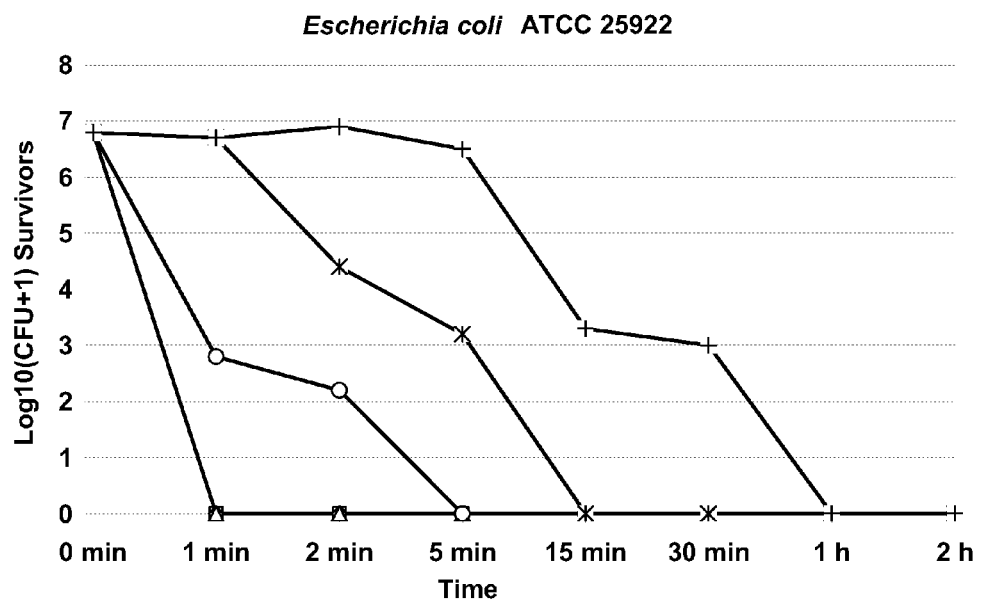

The test organisms used for the suspension-neutralization time-kill studies were S. aureus ATCC 6538 and E. coli ATCC 25922. Bacterial suspensions were prepared by the shake flask method to achieve late log to early stationary phase growth. A 1.0 ml volume of culture was pelleted and resuspended in sterile saline to ~$10^9$ CFU/ml. The in vitro assay was conducted in sterile 20 ml glass scintillation vials. The time-kill reaction vials were prepared to contain 1.0 ml of the appropriate amount of Diluent solution plus fifteen microliters of inoculum followed by the addition of Concentrate solution. The final suspension contained ~$10^7$ CFU/ml and the actual colony counts were confirmed by serial dilutions. Low concentrations of the Enhanced MPO Solution, plus organism suspension, at a final concentration of 0.1, 0.3, 1, 3, 6, and 9 µg/ml were tested (see FIGS. 1A and 1B). Treatment vials were incubated at room temperature. The enzyme reaction was then stopped immediately prior to bacterial quantitation by the addition of 100 µl of a sterile 1% solution of catalase at 1, 2, 5, 15, 30, 60, and 120 minutes. A control culture with no Concentrate solution added was incubated for 30 minutes at room temperature and quantitative cultures performed. A 100 µl sample was removed from each reaction vial at each specified time point and serial dilutions prepared in sterile saline. A 100 µl volume of each dilution was applied to duplicate TSA with 5% sheep blood plates and spread over the surface with a sterile inoculating loop. After overnight incubation at 35° C., the colonies were counted and viable counts were calculated. The bactericidal effect of the Enhanced MPO Solution was defined as a reduction of viable counts relative to the growth control of greater than 99.9% or 3 $\log_{10}$ CFU/ml.

Figure 2A:
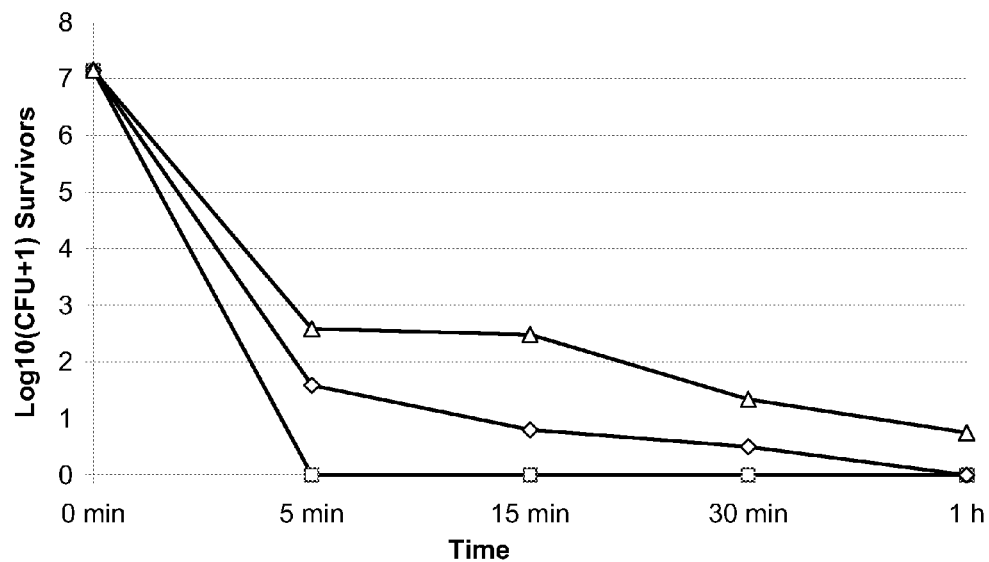
FIG. 2 is a time-kill analysis of S. aureus ATCC 6538 (FIG. 2A) and P. aeruginosa ATCC 27317 (FIG. 2B) treated with the Enhanced MPO Solution containing 200 (□), 100 (◇), and 50 (Δ) µg MPO/ml, as described in Example 11. Isolates were tested in the presence of 3% whole human blood by the suspension-neutralization method. The interference effect of blood on the antimicrobial activity of the Enhanced MPO Solution was overcome at higher MPO concentrations.
Figure 2B:
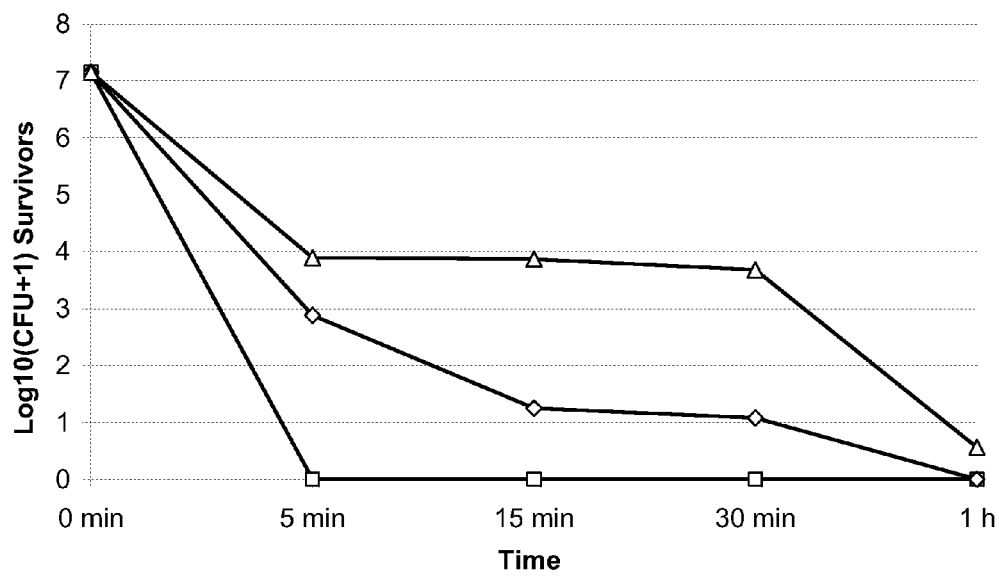
Figure 3A:
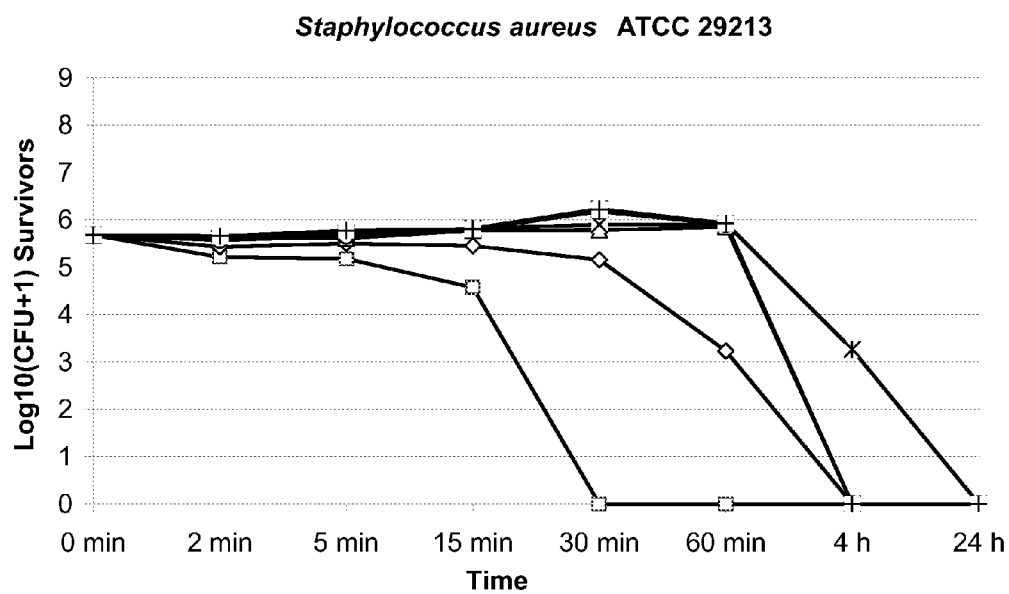
FIG. 3 is a time-kill analysis of S. aureus ATCC 29213 (FIG. 3A), E. coli ATCC 25922 (FIG. 3B), E. faecalis ATCC 29212 (FIG. 3C), and P. aeruginosa ATCC 27853 (FIG. 3D) treated with the Enhanced MPO Solution containing 256 (□), 64 (◇), 16 (Δ), 4 (X), 1 (*), 0.025 (○), and 0.06 (+) µg MPO/ml, as described in Example 11. Bactericidal activity (>3 log reduction from the initial inoculum) was demonstrated using a modified CLSI broth microdilution method. Comparable patterns of kill were observed with all organisms with the rate of kill greater at higher MPO concentrations of the Enhanced MPO Solution and the extent of kill increased with longer exposure and time. At concentrations of 256 and 16 µg MPO/ml, no detectable survivors were observed for all organisms tested within 30 min and 4 hrs, respectively.
Figure 3B:
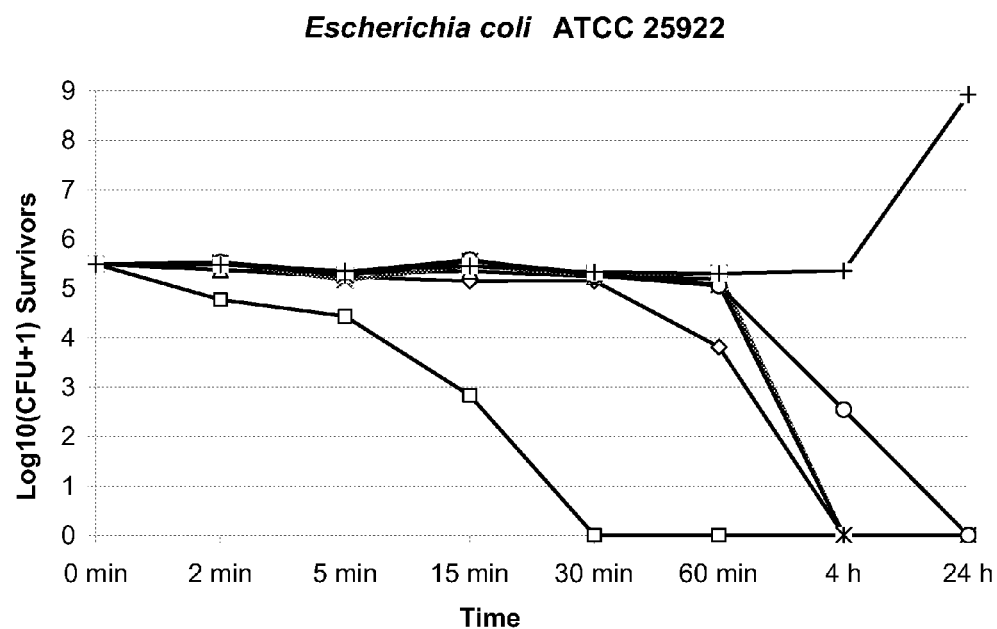
Figure 3C:
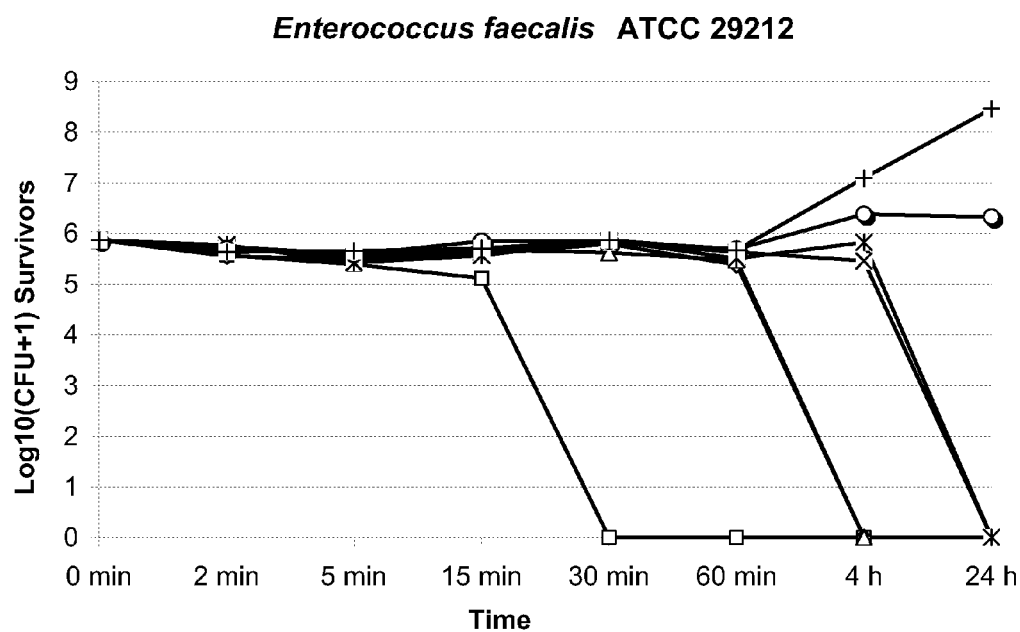
Figure 3D:
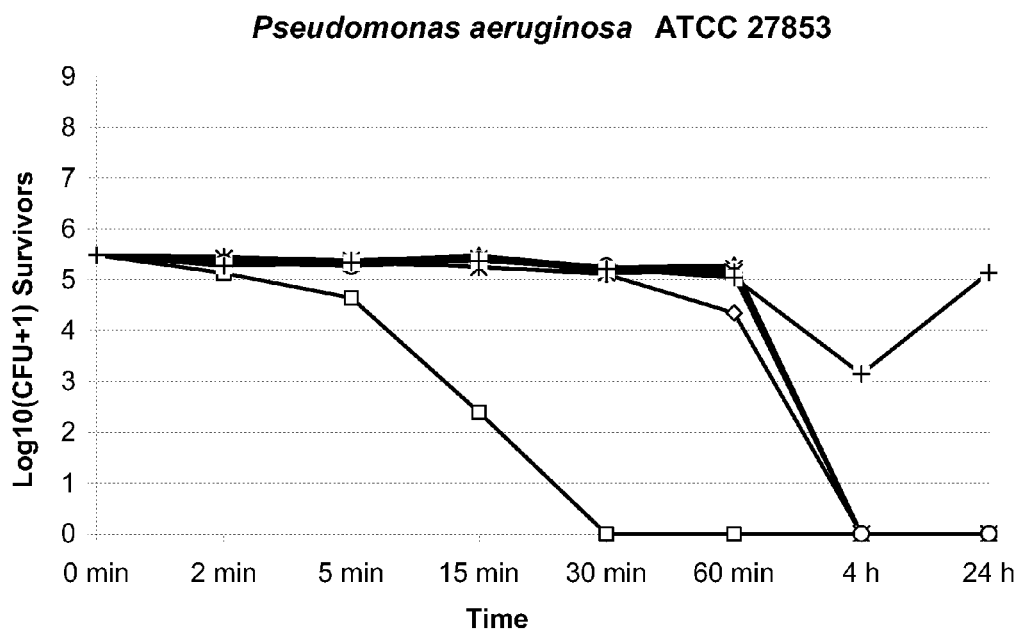

In order to assess the potential of interfering material on the activity of the Enhanced MPO Solution, time-kill studies were performed in the presence of whole human and rat blood, freshly collected in heparinized tubes on the day of the experiment, using the suspension-neutralization method previously described. The Enhanced MPO Solution at 50, 100, and 200 µg/ml was tested against ~$10^7$ CFU/ml inoculum of S. aureus ATCC 6538 and P. aeruginosa ATCC 27317 in the presence of 3% human blood and the bactericidal activity stopped at 5, 15, 30, and 60 minutes (see FIGS. 2A and 2B). The Enhanced MPO Solution at 400, 800, and 1,600 μg/ml was also tested against ~$10^7$ CFU/ml inoculum of S. aureus ATCC 6538 in the presence of 6, 12, and 24% rat blood and the microbicidal activity stopped at 2, 5, 15 minutes, as described above. Two or three replicates were obtained for each test condition.

Test organisms used for the time-kill studies by the modified CLSI method included S. aureus ATCC 29213, E. faecalis ATCC 29212, E. coli 25922, and P. aeruginosa ATCC 27853. Several colonies (four to six), grown on TSA with 5% sheep blood overnight, were suspended in 3 ml of deionized water and suspensions were adjusted to a 0.5 McFarland standard (~$1 \times 10^8$ CFU/ml). This suspension was then diluted 1:10 in pre-warmed CAMHB and incubated 1-4 hours in a shaker incubator at 37° C. When the culture reached its logarithmic growth phase and the turbidity approximated that of a 0.5 McFarland standard, 100 μl was removed and added to 10 ml of Diluent solution to attain a resultant concentration of ~$5 \times 10^6$ CFU/ml. This suspension constituted the inoculum for the time-kill studies. The time-kill reaction wells were prepared to contain 100 μl of Concentrate solution prepared in CAMHB and inoculum (50 μl of Concentrate solution and 50 μl of inoculum prepared in Diluent solution). The final concentrations of MPO in the Concentrate solution were four fold dilutions of the highest concentration: 0, 0.06, 0.25, 1, 4, 16, 64, and 256 μg/ml. An identical reaction well containing broth and inoculum but no Concentrate solution constituted the culture growth control. The final bacterial cell concentration was ~$5 \times 10^5$ CFU/ml. The microdilution trays were incubated at 35° C. in ambient air and 10 μl of a 1% catalase solution was added to each time-kill well at 0, 2, 5, 15, 30, and 60 minutes and 4 and 24 hours to stop the antimicrobial action of the Enhanced MPO Solution. Serial samples were obtained for quantitation. A 100 μl sample was removed from each well at each time point and serial dilutions prepared in sterile saline. A 100 μl volume of each dilution was applied to duplicate TSA with 5% sheep blood plates and spread over the surface with a sterile inoculating loop. The plates at time zero functioned as the purity plates. Following overnight incubation at 35° C., colonies were manually counted and viable counts calculated. Bactericidal activity was defined as a 99.9% or 3 $\log_{10}$ CFU/ml reduction in the colony count from the initial inoculum.

The results of time-kill studies by the suspension-neutralization method are presented in FIG. 1. The data are presented as $\log_{10}$ reduction in CFU relative to the initial inoculum at predetermined timepoints for escalated concentrations of the Enhanced MPO Solution tested. The Enhanced MPO Solution demonstrated very rapid bactericidal activity against both S. aureus and E. coli. The rate of kill was greater at the higher concentrations of the Enhanced MPO Solution and the extent of kill increased with longer exposure time. For S. aureus, the Enhanced MPO Solution was bactericidal yielding greater than 3 $\log_{10}$ reduction in initial inoculum (7.2 $\log_{10}$ CFU/ml) after 2 minutes of exposure to 6 and 9 μg/ml. No detectable growth was observed within 5 minutes exposure to 3, 6 and 9 μg/ml and at 1 μg/ml, greater than 3 $\log_{10}$ reduction was achieved within 5 minutes with no detectable growth at 15 minutes of exposure. No detectable growth was observed after 30 and 120 minutes of exposure to the Enhanced MPO Solution at 0.3, and 0.1 μg/ml, respectively. The Enhanced MPO Solution demonstrated a similar time-kill pattern for E. coli. No detectable growth was observed within 2 minutes exposure to the Enhanced MPO Solution concentrations greater or equal to 3 μg/ml. After 2 minutes of exposure to the Enhanced MPO Solution at 1 μg/ml, more than 3 $\log_{10}$ reduction in initial inoculum (6.8 $\log_{10}$ CFU/ml) was achieved. No detectable growth was observed at 1.0 μg/ml within 5 minutes of treatment. At the lower Enhanced MPO Solution concentrations, 0.3 and 0.1 μg/ml, no detectable growth was observed after 15 and 60 minutes exposure, respectively.

The time- and concentration-dependence of microbicidal activity of the Enhanced MPO Solution was still present in the presence of 3% whole human or rat blood. No significant differences were noted between either sources of blood. The Enhanced MPO Solution at 200 μg/ml, the highest MPO concentration tested in the presence of 3% human blood, yielded no detectable survivors of S. aureus and P. aeruginosa at an initial inoculum of 7.15 $\log_{10}$ CFU/ml in less than 5 minutes. The Enhanced MPO Solution at a concentration of 100 μg/ml, achieved greater than 4 $\log_{10}$ reduction and 5 $\log_{10}$ reduction within 5 minutes for P. aeruginosa and S. aureus, respectively. At 50 μg/ml, the lowest concentration of the Enhanced MPO Solution tested, bactericidal activity was observed at all time points for both organisms (FIG. 2).

The interference effect of blood on the antimicrobial activity of the Enhanced MPO Solution was overcome by increasing the MPO concentration. At Enhanced MPO Solution concentrations of 400 and 800 μg/ml, a reduction of 7.10 $\log_{10}$ CFU/ml S. aureus was achieved with no detectable growth within 2 minutes in the presence of 6 and 12% rat blood. In the presence of 24% rat blood, the Enhanced MPO Solution yielded greater than 4 $\log_{10}$ reduction at 400 and 800 μg/ml, and no detectable survivors at 1,600 μg/ml within 2 minutes.

The results of time-kill studies by the modified CLSI broth microdilution method are presented in FIGS. 3A-3D. The data are presented as $\log_{10}$ reduction in CFU/ml at designated time points. The Enhanced MPO Solution demonstrated bactericidal activity against S. aureus at all concentrations tested. Against E. coli, the Enhanced MPO Solution was bactericidal at all concentrations tested except 0.06 μg/ml, which is 4-fold below its MIC. Likewise for E. faecalis and P. aeruginosa, the Enhanced MPO Solution was bactericidal when tested at concentrations above the MIC. The MICs for E. faecalis and P. aeruginosa were 0.5 and 0.06 μg/ml, respectively. Comparable patterns of microbicidal activity were observed with all four organisms; the rate of kill was greater at higher concentrations of the Enhanced MPO Solution and the extent of kill increased with longer exposure time. At Enhanced MPO Solution concentrations of 256 and 16 μg/ml, no detectable growth was observed for all organisms within 30 minutes and 4 hours, respectively. After 4 hours of exposure to the Enhanced MPO Solution, greater than 3 $\log_{10}$ reduction was achieved at 16 μg/ml for E. faecalis, at 4.0 μg/ml for S. aureus, and at 1.0 μg/ml for E. coli and P. aeruginosa. The faster microbicidal activity observed using the suspension-neutralization method may be attributed to an effect of the media used in the CLSI broth microdilution method.

Time-kill studies as performed by the suspension-neutralization method demonstrated the rate and the extent of bactericidal activity of the Enhanced MPO Solution. Depending on concentration, killing activity was rapid resulting in the reduction of 6 to 7 log 10 CFU/ml of either S. aureus or E. coli within one minute. The rapid bactericidal activity in conjunction with chemiluminescence studies showing production of singlet oxygen (data not shown) supports the proposed mode of action in which singlet oxygen is the principal killing agent. The highly electrophilic nature of singlet oxygen enables it to oxidize regions of high electron density in target biological molecules resulting in destruction of membrane integrity and/or the oxidative inhibition of the enzymes required for metabolic function. Unlike traditional antibiotics, the Enhanced MPO Solution does not appear to depend on the cellular metabolism of the microorganism for inhibition of cell growth or cell death.

Since no standardized methodology for time-kill testing of the Enhanced MPO Solution existed, both the suspension-neutralization and CLSI broth microdilution methods were used to confirm that regardless of organism tested the microbicidal activity of the Enhanced MPO Solution is time- and concentration-dependent. Time-kill studies by the suspension-neutralization method against members or the genus *Candida, Aspergillus, Bacillus* and *Mycobacterium* with prototype formulations also demonstrated time- and concentration-dependent microbicidal activity, with no detectable survivors observed over time.

Antimicrobial Interactions.

Three multi-drug resistant clinical strains were used to test the Enhanced MPO Solution and antibiotic combinations by a checkerboard titration method using 96-well microdilution trays (Moody, J. 2004. Synergism testing: broth microdilution checkerboard and broth macrodilution methods. p. 5.12.1-5.12.23. In H. D. Isenberg, (ed.), Clinical Microbiology Procedures Handbook, $2^{nd}$ ed. ASM Press, Washington, D.C.). The test organisms included vancomycin-intermediate *S. aureus* Mu50 strain (NARSA isolate NRS1) (Hiramatsu, K. H., Hanaki, T. Ino, K. Yabuta, T. Oguri, and F. C. Tenover. 1997. Methicillin-resistant *Staphylococcus aureus* clinical strain with reduced vancomycin susceptibility. J. Antimicrob. Chemother. 40:135-136), *E. coli* (Eurofins 1075701), and *P. aeruginosa* (Eurofins 1445536). Concentrate solution and selected antibiotics were tested by the broth microdilution method with CAMHB and serially diluted (two-fold) alone and in combination. Each well in the checkerboard contained a unique combination of the two drug concentrations and two rows contained one drug alone. Drug concentration ranges for the Enhanced MPO Solution were 0.0005 to 0.5 µg/ml against *S. aureus*, 0.008 to 8 µg/ml against *E. coli*, and 0.001 to 1.0 µg/ml against *P. aeruginosa*. Concentration ranges of antibiotics were one-fourth or less to two times their respective MIC against the tested isolate. The inoculum was prepared in Diluent solution as described above, added to each well of the microdilution trays and incubated in ambient air at 35° C. The MIC of each antimicrobial agent alone and in combination was determined to be the lowest concentration(s) with no visibly detectable growth after 18 to 24 h. The fractionary inhibitory concentration indexes (FICI) were interpreted as follows: ≤0.5, synergy; >0.5 to 4.0, no interaction; and >4.0, antagonism (Odds, F. C. 2003. Synergy, antagonism, and what the chequerboard puts between them. J. Antimicrob. Chemother. 52:1).

In the resistance development studies by the broth microdilution method, the MIC results for *S. aureus, E. faecalis*, and *P. aeruginosa* remained unchanged after passage in sub-inhibitory concentrations of the Enhanced MPO Solution for 21 days. The MICs for three clinical strains of *E. coli* showed an increase of ≥4 doubling dilutions after only one passage from day 1 to day 2, and the MICs remained elevated for 21 days. The change in MICs over the study interval was 0.12 to 8 µg/ml, 0.25 to 8 µg/ml, and 0.5 to 8 µg/ml for each respective strain. After three passages of each of these strains on drug-free agar plates, the MICs upon retesting were not stable and decreased back to ≤2 doubling dilutions of the initial baseline MIC.

Resistance Development.

Multi-step mutational rates were determined by two in vitro methods. Strains passaged daily in sub-inhibitory concentrations of a prototype formulation were tested by the suspension-neutralization method (Millichap, J., T. A. Ristow, G. A. Noskin, and L. R. Peterson. 1996. Selection of *Enterococcus faecium* strains with stable and unstable resistance to the streptogramin RP 59500 using stepwise in vitro exposure. Diagn. Microbiol. Infect. Dis. 25:15-20; Tortorano, A. M., M. A. Viviani, E. Biraghi, A. L. Rigoni, A. Prigitano, R. Grillot, and the EBGA Network. 2005. In vitro testing of fungicidal activity of biocides against *Aspergillus fumigatus*. J. Med. Microbiol. 54:955-957) and the Enhanced MPO Solution was tested in broth microdilution panels (Silverman, J. A., N. Oliver, T. Andrew, and T. Li. 2001. Resistance studies with daptomycin. Antimicrob. Agents Chemother. 45:1799-1802). Three test strains used by the suspension-neutralization method included *S. aureus* ATCC 6538, *P. aeruginosa* ATCC 15442, and a clinical strain of *E. faecium*, vancomycin resistant. Organism suspensions were prepared as previously described to a final target concentration of $10^7$ CFU/ml. For the initial treatment, a 1.0 ml volume of the Enhanced MPO Solution, at 0.1 or 0.3 µg/ml, plus organism suspension were added to each treatment vial. The vials were incubated at 37° C. in a dry bath. After 60 minutes, 100 µl of catalase was then added to each vial to stop the reaction and the entire contents of each vial were cultured on isolation media. In an attempt to induce stable resistance, survivors from the highest Enhanced MPO Solution treated isolation plate after 48 hours of incubation were used to prepare the inoculum for the next passage. Each sequential experiment was performed at the highest previous Enhanced MPO Solution concentration supporting growth and at approximately two times that concentration. Passages were continued for 25 to 30 consecutive days using all three strains.

To determine whether repeated exposure of organisms to sub-inhibitory concentrations of the Enhanced MPO Solution resulted in the rapid development of resistance, a serial passage method was used in microdilution trays (Silverman, J. A., N. Oliver, T. Andrew, and T. Li. 2001. Resistance studies with daptomycin. Antimicrob. Agents Chemother. 45:1799-1802). Ten test strains included *S. aureus* (ATCC 29213, Eurofins 1288199), *E. faecalis* (ATCC 29212, ATCC 51299), *E. coli* (ATCC 25922, Eurofins 1075701, Eurofins 1337451, Eurofins 1337019), and *P. aeruginosa* (ATCC 27853, Eurofins 1077561). Baseline MICs for the Enhanced MPO Solution were determined as described above. Inocula for subsequent MIC tests were prepared from the well containing the highest concentration of the Enhanced MPO Solution that allowed growth. A fresh panel containing Concentrate solution serially diluted in CAMHB was reinoculated with the new suspension prepared in Diluent solution. Passages were continued for 21 consecutive days and the Enhanced MPO Solution MICs were determined following each serial passage. Subsequently, if the MICs showed an increase, stability studies were performed by three serial passages on drug-free agar (TSA) plates during which MICs were again determined.

In the resistance development studies by the broth microdilution method, the MIC results for *S. aureus, E. faecalis*, and *P. aeruginosa* remained unchanged after passage in sub-inhibitory concentrations of the Enhanced MPO Solution for 21 days. The MICs for three clinical strains of *E. coli* showed an increase of ≥4 doubling dilutions after only one passage from day 1 to day 2, and the MICs remained elevated for 21 days. The change in MICs over the study interval was 0.12 to 8 µg/ml, 0.25 to 8 µg/ml, and 0.5 to 8 µg/ml for each respective strain. After three passages of each of these strains on drug-free agar plates, the MICs upon retesting were not stable and decreased back to ≤2 doubling dilutions of the initial baseline MIC.

The resistance development studies showed that the Enhanced MPO Solution and a similar prototype formulation do not select for resistance in *S. aureus, Enterococcus species, P. aeruginosa* and *E. coli*. Although three clinical strains of *E. coli* demonstrated elevated MICs when exposed to the Enhanced MPO Solution, the increase in MICs were not stable and was lost upon subsequent passage on antibiotic free media. These findings, along with the rapid rate of kill and mode of action of the Enhanced MPO Solution, suggest that exposure to the drug product has a very low potential for development of resistance.

The drug interaction studies demonstrated no antagonism on the activity of the conventional antibiotics tested. This is important for applications in which the Enhanced MPO Solution may be used in conjunction with traditional antibiotic therapies. The Enhanced MPO Solution also exerts its potent microbicidal activity in the presence of whole blood, a required attribute in the treatment of surgical and traumatic wounds.

As shown above, the enhanced myeloperoxidase compositions of the invention provide potent, broad-spectrum and rapid bactericidal activity against clinical and reference organisms including drug-susceptible, drug-resistant and multi-drug resistant strains. Their low propensity to select for resistance and lack of drug-drug interaction makes the enhanced compositions of the invention ideal for local/topical anti-infective use for the treatment and prevention of infections in a wide variety of in vivo applications.

Example 12

In Vivo Testing of Enhanced MPO Formulations

In order to evaluate the Enhanced MPO Solution of Example 11 in an in vivo setting, three distinct wound models were employed. These models included a full-thickness excision wound, a partial thickness wound, and deep thigh incision wound.

Antibacterial Agent.

The Enhanced MPO Solution is comprised of two aqueous solutions designated as Concentrate solution and Diluent solution that are mixed prior to use. The Concentrate solution contains MPO, GO, sodium chloride, and specific antimicrobial activity enhancing agents in an aqueous formulation vehicle. The Diluent solution contains glucose (dextrose) in the same aqueous formulation vehicle as the Concentrate solution. The Concentrate and Diluent solutions are mixed together in varying proportions prior to use to produce the drug product Enhanced MPO Solution at a desired concentration. The Enhanced MPO Solution concentration is expressed as Guaiacol Units of MPO per milliliter (GU/ml) and is also expressed as micrograms of MPO per milliliter. The conversion of GU to µg of MPO is based on 0.375 GU/µg of MPO.

Bacterial Strains.

*Staphylococcus aureus* R 136, a clinical strain of MRSA, *S. aureus* ATCC 6538, *Escherichia coli* ATCC 25922 and *Pseudomonas aeruginosa* ATCC 27317 were obtained from Ricerca LLC, (Concord, Ohio) or the American Type Culture Collection.

Experimental Animal Wound Models.

Adult male Sprague-Dawley rats (approximately 250 grams) obtained from Charles River Laboratories, Portage, Mich. were used in each wound model. Animals were housed in individual cages and given food and water ad libitum throughout the study. For all wound models, two wound sites were prepared on each rat. Prior to wounding, the hair of the relevant site was shaved with electric clippers. The animals were anesthetized using isoflurane (1-5% in $O_2$ via face mask). Buprenorphine (0.05 to 0.25 mg/kg IP) was administered for postoperative pain every 12 hours when the animals were not kept under anesthesia for the duration of the study (more than 5 hours). All experimental animal procedures were performed in accordance with the guidelines of the Institutional Animal Care and Use Committees at Ricerca LLC.

(i) Full Thickness Excision Wound Model.

Experimental wounds were induced by a modification of the method reported by Saymen et al. (Saymen, G. D., P. Nathan, I. A. Holder, E. O. Holder, and B. G. Macmillan. 1972. Infected surface wound: an experimental model and a method for the quantitation of bacteria in infected tissues. *Applied microbiology* 23(3)509-514). Methicillin resistant *S. aureus* R 136, *S. aureus* ATCC 6538 or *E. coli* ATCC 25922 were used as challenge organisms. The organisms were prepared as a late log growth suspension grown in Trypticase Soy Broth. Cells were harvested from a shake flask, centrifuged and resuspended in buffered saline to yield a 9 log 10 CFU/ml suspension. This stock was subsequently diluted in buffer to give a working suspension of approximately 7.5 log 10 CFU/ml and used as the inoculum. Two skin wounds were created on each rat by lifting loose skin and excising an elliptical area of skin with scissors using sterile technique and exposing approximately 1 to 2 $cm^2$ of fascia. Three rats with two wounds each were used in all treatment groups. An open 2.5 cm diameter polystyrene cylinder was glued to the skin around each excised site with Quick Tite® (Loctite Corp.) cement similar to the procedure reported by Breuing, et. al. (Breuing K., S. Kaplan, P. Liu, A. B. Onderdonk, and E. Eriksson. 2003. Wound fluid bacterial levels exceed tissue bacterial counts in controlled porcine partial-thickness burn infections, *Plast. Reconstr. Surg.* 111:781-788). Each cylinder formed a liquid-tight test chamber, the base of which was the exposed fascia. The exposed wound was inoculated by depositing 200 µL containing $10^7$ CFU of the bacterial suspension directly on the fascia. This volume of inoculum was sufficient to completely cover the exposed fascia. After application, the inoculum was allowed to remain on the fascia for 15 minutes before treatment. A volume of 800 µL of the Enhanced MPO Solution was added to the site resulting in a total volume of 1 ml per test site. Control sites, where 800 µL of 0.9% sterile saline or buffer was added, had no Enhanced MPO Solution administered. Both wound sites on a single rat received the identical treatment. Following the 5, 15, 30, or 60-minute treatment time with the Enhanced MPO Solution, a large excess of catalase solution was added to each site to destroy any remaining enzyme and/or subsequently generated hydrogen peroxide, thereby inhibiting further microbicidal activity. The liquid in the cylinder was recovered and the underlying fascia aseptically was excised, weighed, and homogenized. Surviving bacterial counts in the recovered liquid sample and tissue homogenate for each site were separately assessed by quantitative culture using serial 10-fold dilutions plated on Trypticase Soy Agar (TSA) and incubated at 37° C. overnight. Treatment performance was calculated as the sum of counts from the recovered liquid and tissue homogenate for each wound and is reported as the average of all samples in each treatment group.

Figure 4:
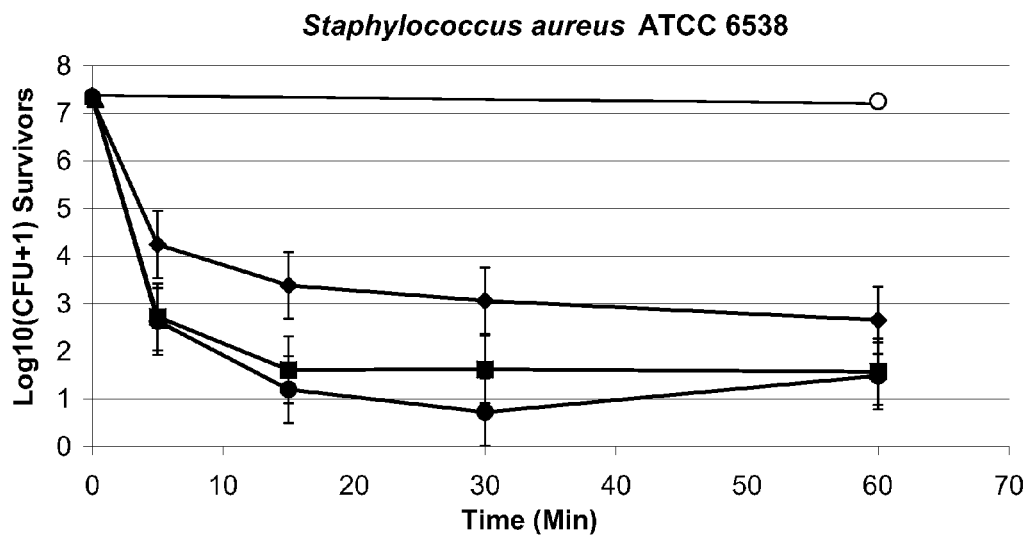
FIG. 4 is a time kill analysis of S. aureus ATCC 6538 in the full-thickness wound model in rats treated with the Enhanced MPO Solution containing 18.75 (♦), 75 GU/ml (■), and 150 (●) GU/ml as described in Example 12. Organism recovery from untreated wounds at 60 min (○). This graph presents the mean log 10 CFU survivors isolated from each treatment group at 5, 15, 30 and 60 minutes treatment time. The 95% confidence interval of each data point is shown for each treatment group.

For the full thickness wound model, mean log 10(CFU+1) survivors were calculated from the raw data. The 95% confidence intervals on the means were calculated from the standard error of the mean and the t-value reflecting the appropriate number of degrees of freedom. The activity of the Enhanced MPO Solution exhibited time- and concentration-dependence at three different p-MPO concentrations, 18.75, 75 and 150 GU MPO/ml, in a full thickness excision model. As shown in FIG. 4, the Enhanced MPO Solution containing 75 GU MPO/ml and 150 GU MPO/ml yielded nearly complete kill of a greater than 7 $\log_{10}$ inoculum of *S. aureus* ATCC 6538 within 15 minutes. Treatment with the Enhanced MPO Solution at both concentrations resulted in a greater than 4 $\log_{10}$ CFU reduction within 5 minutes. When the concentration was decreased to 18.75 GU MPO/ml, approximately 3 $\log_{10}$ CFU reduction was still achieved within 5 minutes. The log number of CFU per wound recovered from the Enhanced MPO Solution treated wounds was statistically different (p<0.05) from both the inoculum (7.3 $\log_{10}$) and untreated infection controls (7.25 $\log_{10}$) for all of the concentrations and time-points tested.

Figure 6:
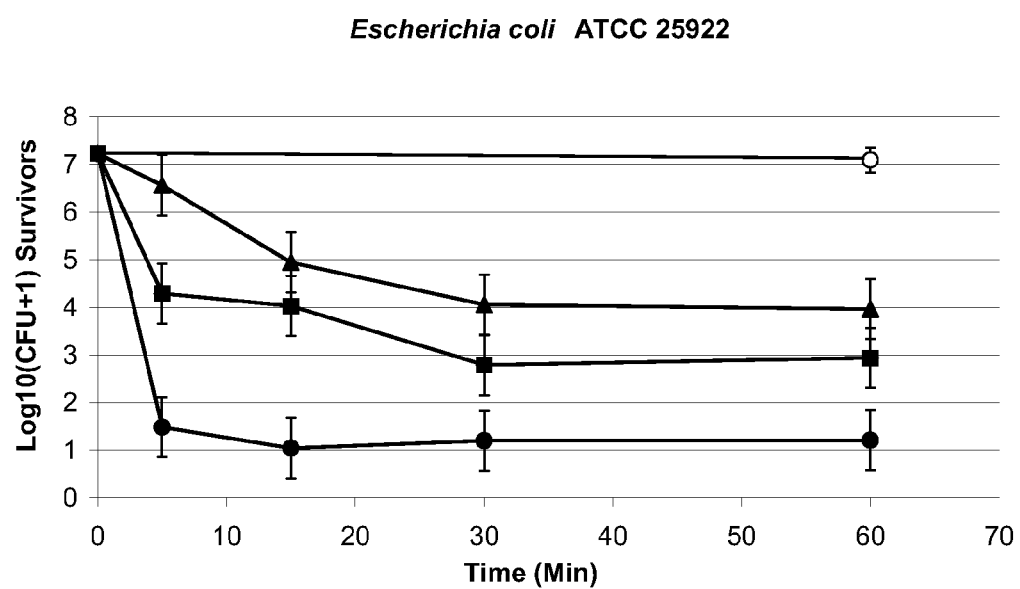
FIG. 6 is a time kill analysis of E. coli ATCC 25922 in the full-thickness wound model in rats treated with an Enhanced MPO Solution containing 18.75 (♦), 75 GU/ml (■), and 150 (●) GU/ml, as described in Example 12. Organism recovery from untreated wounds at 60 min (○). This graph presents the mean log 10 CFU survivors isolated from each treatment group at 5, 15, 30 and 60 minutes treatment time. The 95% confidence interval of each data point is shown for each treatment group.

The effect of the Enhanced MPO Solution on wounds inoculated with *E. coli* ATCC 25922 is shown in FIG. 6. As observed with *S. aureus*, bacterial counts decreased rapidly within 5 minutes after treatment with the Enhanced MPO Solution. Near complete kill of the applied inoculum (7.2 $\log_{10}$) was observed within 5 minutes in wounds treated with the Enhanced MPO Solution containing 150 GU MPO/ml.

These results confirmed the rapid and time- and concentration-dependent activity of the Enhanced MPO Solution against *S. aureus* and *E. coli* in an environment comprising tissue and wound exudates.

Figure 5:
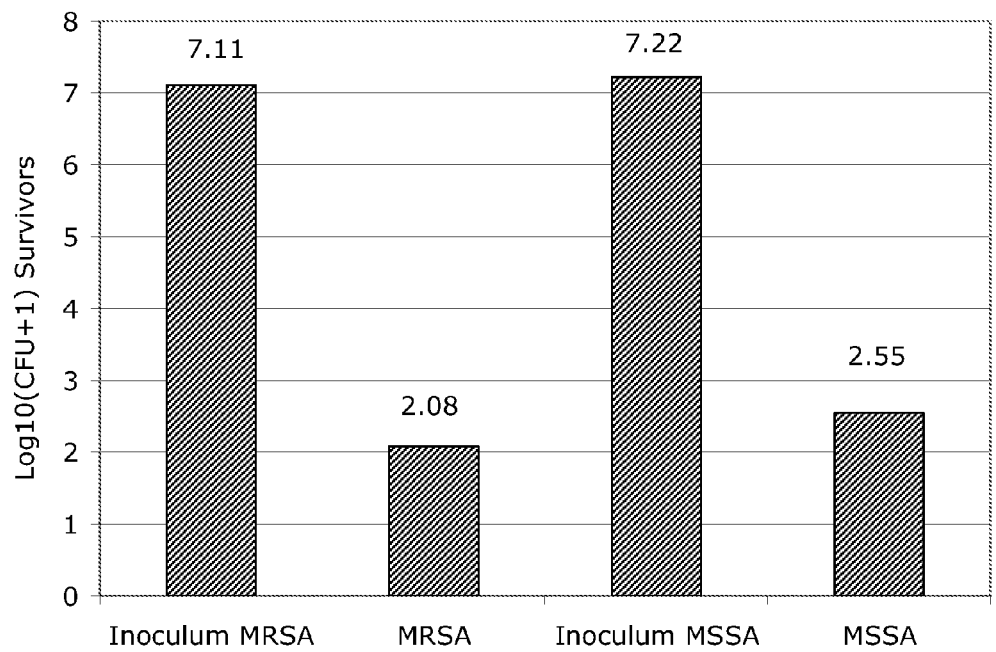
FIG. 5 is a comparison of microbicidal activity of an Enhanced MPO Solution against Methicillin Resistant S. aureus (MRSA) and Methicillin Sensitive S. aureus (MSSA) in the partial-thickness wound model in rats, as described in Example 12. This graph presents the mean log 10 CFU survivors isolated 15 minutes after treatment.

No significant difference was seen between the bactericidal activity of the Enhanced MPO Solution against MRSA and MSSA in wounds, 15 minutes after treatment (FIG. 5). In both cases, the recovery of viable organisms from the treatment groups indicated an approximate 5 $\log_{10}$ decrease in CFU from the inoculum control. The extent of kill after 15 minutes of exposure to the treatment was compared to the inoculum as previous results did not indicate any appreciable decrease or increase in bacterial viability for up to an hour following bacterial inoculation of the wound site (FIG. 5 and FIG. 6). These findings corroborate the in vitro activity of the Enhanced MPO Solution described in Example 11 against both methicillin resistant and susceptible organisms ($MIC_{90}$, 0.03 µg MPO/ml).

(ii) Partial Thickness Wound Model.

*Staphylococcus aureus* ATCC 6538 was used as the challenge organism. The inoculum was prepared as describe above for the full-thickness excision wound. Experimental wounds consisted of two 10 mm×7 mm sites midline on the back of each rat, one site being forward near the shoulders and one site being caudal. The wound was achieved by controlled abrasion of the skin. The skin was pinched using fingers to form a fold and rubbed with a grater using 10 strong passes. This produced a wound with a slight depression (i.e., about ⅓ to ½ the thickness of the skin) with some minor bleeding, which was blotted dry. Tests were organized into 4 to 5 treatments groups per experiment with each treatment administered to 3 rats. Each of the rats had two wounds giving 6 wound sites per experimental group. Twenty-five microliters of a $10^6$ CFU/ml inoculum was dispensed in the center of the exposed wound and rubbed for 10 seconds over the entire wound area using a sterile polypropylene spatula. Twenty minutes after application of the inoculum, 1 ml of either the Enhance MPO Solution or placebo was swabbed with a cotton swab for 30 seconds on the wound site. A saturated gauze containing 3 ml of the Enhanced MPO Solution or placebo was then applied to each wound and the wound covered with Tegaderm. All treated sites were harvested at 3 or 24 hr post-inoculation and cultured for viable organisms. The Tegaderm and gauze were removed and the entire wound was excised down to the fascia, placed in a tared sterile tube, weighed and 1 ml of sterile cold 0.9% saline added to each tube. The tissue was then homogenized and surviving bacterial counts in the recovered tissue homogenate for each site were assessed by quantitative culture using serial 10-fold dilutions, plated on TSA and incubated at 37° C. overnight. Treatment performances are reported as the average of the counts from the recovered tissue sample for each treatment group.

Mean log 10(CFU+1) survivors were calculated from the raw data. The 95% confidence intervals on the means were calculated from the standard error of the mean and the t-value reflecting the appropriate number of degrees of freedom. The extent of the activity of the Enhanced MPO Solution (E-MPO) at 75, 150 or 300 GU MPO/ml was assessed at 3 and 24 hours following treatment in the partial thickness wound model as shown in the following Table 35. This Table presents the mean log 10 CFU survivors isolated 3 and 24 hours the after various treatments. The 95% confidence interval of each is shown for each treatment group. Significant differences were observed between the placebo control and the Enhanced MPO Solution-treated groups with respect to the number of viable *S. aureus* CFU recovered from the tissue samples.

TABLE 35

Partial Thickness Excision Model -
In vivo Microbicidal Activity of Enhanced MPO
Solution against *S. aureus* ATCC 6538

| Treatment Group | Log10(CFU + 1) Survivors ± 95% Confidence Interval |
|---|---|
| 3 hours Following Single Treatment | |
| Infection Control - Untreated | 4.2 ± 0.068 |
| E-MPO Solution - 150 GU/ml | 0.8 ± 0.614* |
| 24 hours Following Single Treatment | |
| Placebo Treated | 5.9 ± 0.143 |
| E-MPO Solution - 150 GU/ml | 4.8 ± 0.807* |
| 24 hours Following Single Treatment | |
| Placebo Treated | 6.2 ± 0.697 |
| E-MPO Solution - 75 GU/ml | 5.3 ± 0.997 |
| E-MPO Solution - 300 GU/ml | 4.4 ± 0.637 |

*represents treatment groups that are statistically different from placebo or infection controls.

After a single application of the Enhanced MPO Solution at 150 GU/ml, the mean number of organisms isolated from the wounds was approximately 0.8 $\log_{10}$ CFU (~6 CFU) at 3 hours. This represented more than a 3 $\log_{10}$ reduction compared to the infection control.

Single applications of the Enhanced MPO Solution containing MPO at 75, 150, and 300 GU/ml were examined to determine a dose response and were compared to the placebo control at 24 hours. Treatment using the Enhanced MPO Solution at 75 GU/ml reduced the number of organisms recovered to 5.3 $\log_{10}$ CFU. However, this reduction was not statistically significant compared to the placebo treated group with a recovery of 6.2 $\log_{10}$ CFU (p=0.15). After a single application of the Enhanced MPO Solution at 150 GU/ml, the number of organisms recovered from the wounds was approximately 1.1 $\log_{10}$ CFU less than the placebo control (p<0.01). Wounds treated with the Enhanced MPO Solution at 300 GU/ml contained approximately 4.4 $\log_{10}$ CFU compared to 6.2 $\log_{10}$ CFU recovered from the placebo treated control group (p=0.01). These findings indicate that there is a dose response at 24 hours for the Enhanced MPO Solution against *S. aureus* and a sustained effect in the reduction of the level of contamination of the wounds after a single treatment.

(iii) Deep Thigh Incision Wound Model.

Methicillin resistant *S. aureus* R 136 or *Pseudomonas aeruginosa* were used as the challenge organisms and the inocula were prepared as described above. Wounds consisted of one incision in both thighs of each rat when MRSA is used and one incision in only one thigh for *P. aeruginosa*. For each leg, the spine, the greater trochanter and the knee were marked and a line from the knee through the greater trochanter, toward the spine traced. The skin was incised using scissors approximately 3 cm along the line centered on the greater trochanter and the skin undermined on the edges to approximately 1 cm. The deep incision was made down to the level of the femur inferiorly, and into the gluteal muscles superiorly. The wound depth was confirmed by touching the femur shaft using forceps. Tests with *S. aureus* were organized into 3 treatments groups per experiment; the Enhanced MPO Solution, saline treatment and untreated controls. Ten rats were used to compare the Enhanced MPO Solution to saline, with one leg receiving the Enhanced MPO Solution and the other leg being treated with saline. Additionally, five animals received the Enhanced MPO Solution in the left leg and 5 animals received it in the right leg. Two rats received inoculation and no treatment, resulting in 4 wounds for the untreated controls.

Tests with *P. aeruginosa* were also organized into 3 treatments groups per experiment with 4 rats used for the Enhanced MPO Solution, saline treatments, and untreated controls, respectively. Each of the rats had a single wound giving 4 wound sites per experimental group. A 100 µL inoculum of a $10^9$ CFU/ml organism suspension was dispensed in the depth of the wound using a sterile pipette. Sixty 60 minutes after inoculation with *S. aureus*, the wounds were treated either once with 2.5 ml of the Enhanced MPO Solution at 75 GU/ml or twice, 15 min apart, with 10 ml of the Enhanced MPO Solution at 300 GU/ml (see Table 36). Sixty 60 minutes after inoculation with *P. aeruginosa*, the wounds were treated twice, 15 min apart, with 5 ml of the Enhanced MPO Solution at 300 GU/ml (see Table 37). All of the Enhanced MPO Solution and saline treatments were applied using a syringe with a gavage needle. Treated wounds were closed using two skin clips immediately after the second treatment whereas the untreated control wounds were closed immediately after bacterial inoculation. Wound assessment was performed on day 4. An evaluation of each wound was performed and an infectivity score assigned. Two key metrics of infection were used to determine the infectivity score, specifically the area of induration and the presence or absence of purulence. The area of induration was measured in square mm using a caliper and the presence of purulence was determined by surgically opening each wound. The infectivity score was assigned the value of the area of induration and if purulence was present the infectivity score was increased by 25%. There was no reduction of the infectivity score if purulence was absent.

Mean infectivity scores were determined from data pooled from multiple experiments by PROC MIXED (SAS, SAS Institute, Cary, N.C.), using a model with wounds nested within rats, and rats nested within experiments. Both rats and experiments are considered as random variables in this model. Pairwise comparisons of mean values were made using the t-test. The effect of the Enhanced MPO Solution on the progression of infection by the methicillin resistant strain of *S. aureus* or *Pseudomonas aeruginosa* was determined at 4 days post-inoculation in the deep thigh incision wound model. As shown in the following Table 36, none of the groups treated with the Enhanced MPO Solution (E-MPO) were statistically different from each other. The * represents treatment groups that are statistically different from placebo and the # represents treatment groups that are statistically different infection controls.

The infectivity score for the Enhanced MPO Solution treated groups was compared to the infectivity rating of the saline and untreated groups at 4 days post-treatment, as shown in the following Tables 36 and 37.

TABLE 36

Deep Thigh Incision Wound Model - In vivo Microbicidal Activity of Enhanced MPO Solution against *S. aureus*

| Treatment$^a$ | N | Infectivity Rating |
|---|---|---|
| Untreated | 44 | 303* |
| Saline - 2 × 10 ml | 28 | 195# |
| Saline - 1 × 2.5 ml | 30 | 216# |
| E-MPO Solution (300 GU/ml - 2 × 10 ml) | 31 | 110*# |
| E-MPO Solution (75 GU/ml - 1 × 2.5 ml) | 10 | 84*# |

N is the number of legs per treatment group.
*represents treatment groups that are statistically different from placebo.
represents treatment groups that are statistically different infection controls.

TABLE 37

Deep Thigh Incision Wound Model - In vivo Microbicidal Activity of Enhanced MPO Solution against *P. aeruginosa*

| Treatment$^a$ | N | Infectivity Rating |
|---|---|---|
| Untreated | 4 | 1032* |
| Saline - 2 × 5 ml | 4 | 705# |
| Enhanced MPO Solution (300 GU/ml - 2 × 5 ml) | 4 | 86*# |

N is the number of legs per treatment group.
*represents treatment groups that are statistically different from placebo.
represents treatment groups that are statistically different infection controls.

Animals inoculated with MRSA were treated either twice with 10 ml of the Enhanced MPO Solution at 300 GU/ml or once with 2.5 ml of the Enhanced MPO Solution at 75 GU/ml. Examinations of the wounds 4 days post-treatment indicated a higher incidence of presence of purulence for all untreated wounds (59%) compared to the saline treated wounds (25%) and the Enhanced MPO Solution treatment groups (10% at both 300 GU/ml and 75 GU/mL).

The average infectivity score of 110, for animals treated twice with 10 mL of the Enhanced MPO Solution at 300 GU/ml, was statistically different (p-value<0.05) from that of the two saline treatments and the untreated groups having infectivity scores of 216, 195, and 303, respectively (Table 36). No statistical differences (p>0.05) could be discerned between the high concentration/high volume and low concentration/low volume of the Enhanced MPO Solution treatments.

As also shown in Table 36, the simultaneous decrease of the concentration and volume of the Enhanced MPO Solution, from 10 ml applied twice at 300 GU/ml to 2.5 ml applied once at 75 GU/ml, resulted in an infectivity score of 84 which is statistically different (p-value<0.05) from the infectivity scores of 216, 195, and 303 obtained for animals treated with 2.5 mL saline applied once, animals treated with 10 mL saline applied twice, and the untreated animals, respectively. No statistical differences (p>0.05) could be discerned between the high concentration/high volume and low concentration/ low volume Enhanced MPO Solution treatments.

The change in organism from *S. aureus* to *P. aeruginosa* led to an increase in the severity of the model and lethality when both legs were inoculated (data not shown) therefore a single leg per animal was used when animals were inoculated with *P. aeruginosa*. Additionally, since *P. aeruginosa* can become systemic after localized administration, using the two legs of animals for different treatments was unadvisable and likely to lead to unclear outcomes. As shown in Table 37, the average infectivity score of 86, for animals treated twice with 5 mL of the Enhanced MPO Solution at 300 GU/ml, was statistically different (p-value<0.05) from both the saline treated group (IS=705) and untreated group (1032). The observation at day 4 led to a higher incidence of purulence for all untreated wounds (50%) compared to the saline treated wounds (25%) and the Enhanced MPO Solution treatment groups (0%).

Specifically, these results demonstrate the dose- and time-dependent cidal activity of the Enhanced MPO Solution against *S. aureus* and *E. coli* in the full thickness wound infection model. The Enhanced MPO Solution was effective in reducing bacterial loads in the presence of wound exudates after a single application, and importantly, without the addition of conventionally used antibiotics. This cidal effect is rapid and translates into reduced bacterial recoveries compared to placebo or untreated controls, even 24 hours after treatment with the Enhanced MPO Solution.

In summary, these microbicidal results coupled with the broad-spectrum, rapid bactericidal activity, low propensity to select for resistance, and lack of drug-drug interaction seen in the in vitro studies, strongly support the use of the compositions of the invention for the treatment, prevention, and reduction of infections in vivo.

While illustrative embodiments have been illustrated and described, it will be appreciated that various changes can be made therein without departing from the spirit and scope of the invention.

The invention claimed is:

1. A composition for inhibiting the growth of susceptible microorganisms comprising myeloperoxidase, glucose oxidase, sodium chloride, polysorbate 80, phosphate buffer, and two amino acids, wherein one of the two amino acids is glycine, and the other of the two amino acids is selected from the group consisting of D-isoleucine; L-isoleucine; L-tyrosine; and L-valine; and wherein the two amino acids work in combination to enhance the microbicidal activity of the myeloperoxidase.

2. The composition of claim 1, wherein glucose oxidase is present in an amount effective to generate from 100 pmol to 50 µmol peroxide per ml per minute when in the presence of a substrate for the oxidase.

3. The composition of claim 1 which comprises from 1 to 50,000 µg/ml of myeloperoxidase.

4. The composition of claim 1 which comprises from 0.1 to about 500 mM of each of the two amino acids.

5. A composition for killing or inhibiting the growth of susceptible microorganisms, wherein the composition consists of myeloperoxidase, glycine, L-alanine, L-proline, glucose oxidase, sodium chloride, polysorbate-80, sodium phosphate buffer, and water, wherein the glycine, L-alanine, and L-proline in the composition work in combination to enhance the microbicidal activity of the myeloperoxidase.

6. A method of treating a microbial infection in a human or animal subject, comprising administering to a site of infection in the subject a composition of claim 1.

7. The method of claim 6 wherein the composition comprises glucose oxidase in an amount effective to generate from 100 pmol to 50 µmol peroxide per ml per minute when in the presence of a substrate for the oxidase.

8. The method of claim 6 wherein the composition comprises from 1 to 50,000 µg/ml of myeloperoxidase.

9. The method of claim 6 wherein the composition comprises from 0.1 to about 500 mM of each of the two amino acids.

10. The method of claim 6 wherein the human or animal subject is suffering from a microbial infection of the gums, eyes, ears, skin, soft tissue, wounds, vaginal areas, groin areas, bed sores or burn areas.

11. The method of claim 10 wherein the infection is a polymicrobial infection.

12. A method for killing or inhibiting the growth of susceptible microorganisms comprising contacting the microorganisms with the composition of claim 1.

13. A binary combination, comprising:
   (a) a first composition comprising myeloperoxidase, glucose oxidase, sodium chloride, polysorbate-80, phosphate buffer, water and two amino acids, wherein one of the two amino acids is glycine, and the other of the two amino acids is selected from the group consisting of D-isoleucine; L-isoleucine; L-tyrosine; and L-valine; and wherein the two amino acids work in combination to enhance the microbicidal activity of the myeloperoxidase; and
   (b) a second composition comprising glucose and water.

14. A binary combination for killing or inhibiting the growth of susceptible microorganisms, consisting of:
   (a) a first composition consisting of myeloperoxidase, glycine, L-alanine, L-proline, glucose oxidase, sodium chloride, polysorbate-80, sodium phosphate buffer, and water, wherein the glycine, L-alanine, and L-proline in the composition work in combination to enhance the microbicidal activity of the myeloperoxidase; and
   (b) a second composition comprising glucose and water.

15. A method of treating a microbial infection in a human or animal subject, comprising administering to a site of infection in the subject a composition of claim 5.

16. A method for killing or inhibiting the growth of susceptible microorganisms comprising contacting the microorganisms with the composition of claim 5.

17. The method of claim 15 wherein the human or animal subject is suffering from a microbial infection of the gums, eyes, ears, skin, soft tissue, wounds, vaginal areas, groin areas, bed sores or burn areas.

18. The method of claim 17 wherein the infection is a polymicrobial infection.

19. The composition of claim 5, wherein the myeloperoxidase is present in a concentration front bout 10 µg/ml to about 5,000 µg/ml.

20. The composition of claim 5, wherein each of the glycine, L-alanine, and L-proline is present in a concentration from about 0.3 mM to about 50 mM.

21. The composition of claim 5, wherein the glucose oxidase is present in a concentration from about 1 U/ml to about 500 U/ml.

* * * * *

UNITED STATES PATENT AND TRADEMARK OFFICE
CERTIFICATE OF CORRECTION

PATENT NO. : 8,945,540 B2  
APPLICATION NO. : 12/118586  
DATED : February 3, 2015  
INVENTOR(S) : Becquerelle et al.

Page 1 of 1

It is certified that error appears in the above-identified patent and that said Letters Patent is hereby corrected as shown below:

In the Specification

Column 11, line 14, "Acintobacter" to read as --Acinetobacter--.

Column 11, line 15, "hydrophilia," to read as --hydrophila,--.

Column 11, line 19, "Aspergillis" to read as --Aspergillus--.

Column 25-26, under TABLE 11, line 2, "ofthe" to read as --of the--.

Column 27-28, under TABLE 11, line 2, "ofthe" to read as --of the--.

Column 45, line 56 approx., "mircrodilution" to read as --microdilution--.

Column 47, under TABLE 33, line 32 approx., "Acintobacter" to read as --Acinetobacter--.

Column 47, under TABLE 33, line 36 approx., "hydrophilia(5)" to read as --hydrophila(5)--.

In the Claims

Column 61, line 61, Claim 6, "a" to read as --the--.

Column 62, line 54, Claim 19, "front bout" to read as --from about--.

Signed and Sealed this  
Eighth Day of September, 2015

Michelle K. Lee  
*Director of the United States Patent and Trademark Office*